(12) United States Patent
Lipton et al.

(10) Patent No.: US 8,466,311 B2
(45) Date of Patent: Jun. 18, 2013

(54) NEUROPROTECTIVE COMPOSITIONS AND METHODS

(75) Inventors: Stuart A. Lipton, La Jolla, CA (US); Takumi Satoh, La Jolla, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 13/236,579

(22) Filed: Sep. 19, 2011

(65) Prior Publication Data

US 2012/0296112 A1 Nov. 22, 2012

Related U.S. Application Data

(63) Continuation of application No. 11/974,114, filed on Oct. 10, 2007, now Pat. No. 8,022,246.

(60) Provisional application No. 60/850,860, filed on Oct. 10, 2006, provisional application No. 60/850,918, filed on Oct. 10, 2006.

(51) Int. Cl.
   *C07C 61/29* (2006.01)
(52) U.S. Cl.
   USPC ......................... 562/403; 562/404
(58) Field of Classification Search
   None
   See application file for complete search history.

(56) References Cited

PUBLICATIONS

Braga et al., Chem. Commun. (2005), 29, p. 3635-3545.*
Banker et al. eds., Modern Pharm. 3$^{rd}$ ed. (1996), p. 596.*
Wolff el., Burger's Medicinal Chemistry and Drug Discovery 5$^{th}$ ed., vol. 1, (1995), p. 975-977.*
Database CAPLUS on STN, Acc. No. 1996:676200, Torii et al., JP 08239306 A (Sep. 17, 1996) (abstract).*
Database CAPLUS on STN, Acc. No. 1987:30032, Castro et al., Ingenieria y Ciencia Quimica (1986), 10(12), p. 5-6 (abstact).*
Database CAPLUS on STN, Acc. No. 1998:361334, Kuo et al., Journal of Natural Products (1998), 61(6), p. 829-831 (abstract).*
Database CAPLUS on STN, Acc. No. 1982:199922, Matsumoto et al., Bulletin of the Chemical Society of Japan (1982), 55(2), p. 527-533 (abstract).*

* cited by examiner

*Primary Examiner* — Brian J Davis
(74) *Attorney, Agent, or Firm* — Sam K. Tahmassebi; TechLaw LLP

(57) ABSTRACT

Neurite outgrowth-promoting prostaglandins (NEPPs) and other electrophilic compounds bind to Keap1, a negative regulator of the transcription factor Nrf2, and prevent Keap1-mediated inactivation of Nrf2 and, thus, enhance Nrf2 translocation into the nucleus of neuronal cells. Therefore, neuroprotective compositions and related methods are provided that employ such neuroprotective compounds, and prodrugs of such compounds, to cause dissociation of Nrf2 from a Keap1/Nrf2 complex.

3 Claims, 11 Drawing Sheets a *Catechol-type* electrophilic compounds

Non electrophilic
(catechol-type) → (Oxidation) → Electrophilic (quinone-type)

CA b *Enone-type* electrophilic compounds

Enone — Curcumin

Dienone — NEPP11 (Neurons)

Itself electrophilic

FIGURE 3 (con't)
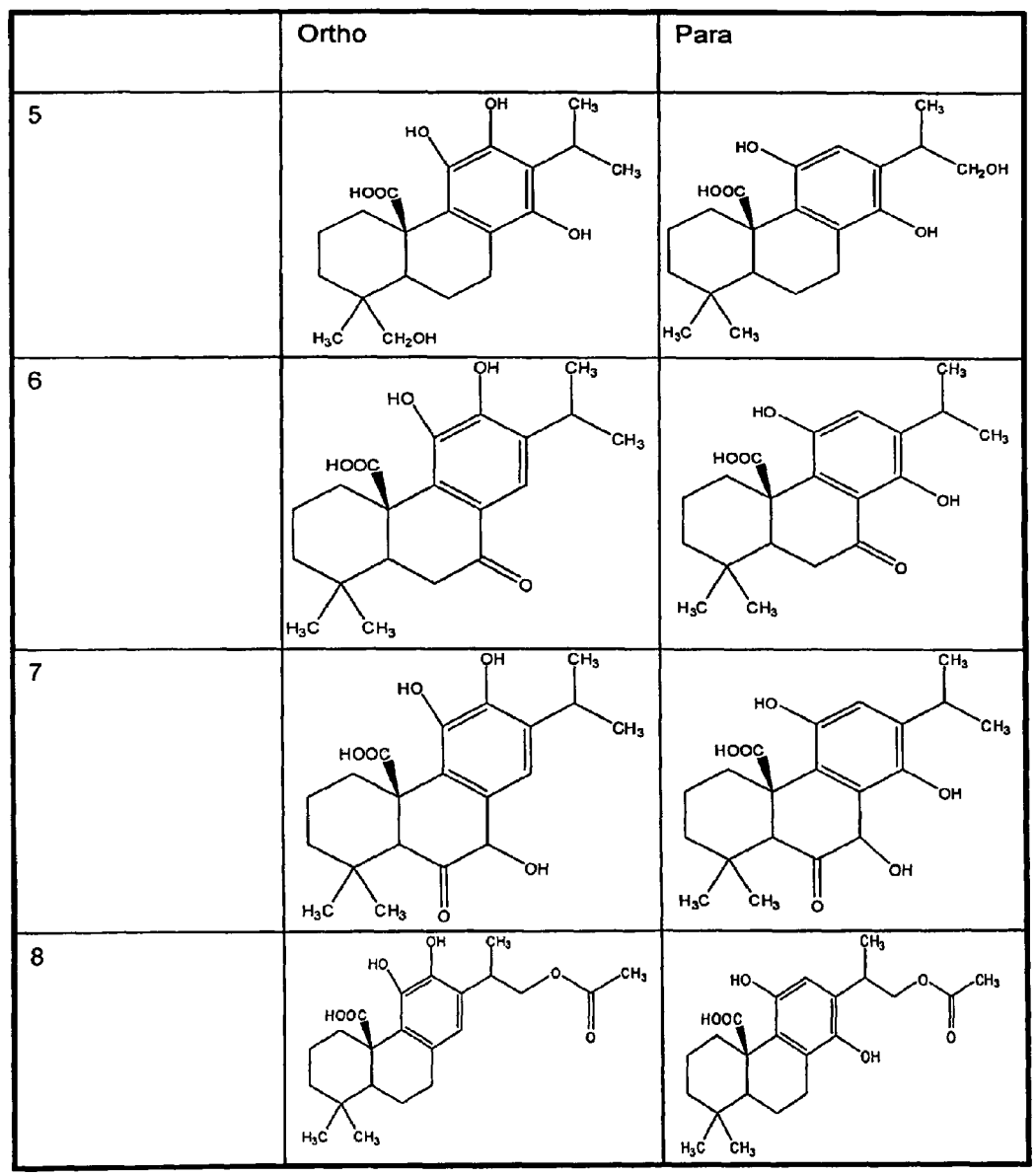

SEQUENCE LISTING

```
<160> NUMBER OF SEQ ID NOS: 27

<210> SEQ ID NO 1
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 1
ctcagccttc caaatcgcag tcacagtgac tcagcagaat c                          41

<210> SEQ ID NO 2
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 2
```
ctcagccttc caaatcgcag tcacagtgac tcaatagaat c                          41

<210> SEQ ID NO 3
<211> LENGTH: 27
<212> TYPE: DNA
<213> ORGANISM: Artificial Sequence
<220> FEATURE:
<223> OTHER INFORMATION: Synthetic primer

<400> SEQUENCE: 3
cgtggtggac ttctctgcta cgtggtg                                          27

<210> SEQ ID NO 4
<211> LENGTH: 27
<212> TYPE: DNA
<213> ORGANISM: Artificial Sequence
<220> FEATURE:
<223> OTHER INFORMATION: Synthetic primer

<400> SEQUENCE: 4
ggtcggcatg catttgactt cacagtc                                          27

<210> SEQ ID NO 5
<211> LENGTH: 27
<212> TYPE: DNA
<213> ORGANISM: Artificial Sequence
<220> FEATURE:
<223> OTHER INFORMATION: Synthetic primer

<400> SEQUENCE: 5
gctagagaag atggtcgcca agcagca                                          27

<210> SEQ ID NO 6
<211> LENGTH: 27
<212> TYPE: DNA
<213> ORGANISM: Artificial Sequence
<220> FEATURE:
<223> OTHER INFORMATION: Synthetic primer

<400> SEQUENCE: 6
tcctcgtcct tgatccccac aaacttg                                          27

<210> SEQ ID NO 7
<211> LENGTH: 29
<212> TYPE: DNA
<213> ORGANISM: Artificial Sequence
<220> FEATURE:
<223> OTHER INFORMATION: Synthetic primer

<400> SEQUENCE: 7
tgcagaaaga cccaagaaat cctcagtca                                        29

<210> SEQ ID NO 8
<211> LENGTH: 29
<212> TYPE: DNA
<213> ORGANISM: Artificial Sequence
<220> FEATURE:
<223> OTHER INFORMATION: Synthetic primer

<400> SEQUENCE: 8
tggagattag atcactgcat ccgcctatg                                        29

<210> SEQ ID NO 9
<211> LENGTH: 28
<212> TYPE: DNA
<213> ORGANISM: Artificial Sequence
<220> FEATURE:

<223> OTHER INFORMATION: Synthetic primer

<400> SEQUENCE: 9
catcctgctc ttactgttcc atggccaa    28

<210> SEQ ID NO 10
<211> LENGTH: 29
<212> TYPE: DNA
<213> ORGANISM: Artificial Sequence
<220> FEATURE:
<223> OTHER INFORMATION: Synthetic primer

<400> SEQUENCE: 10
tcatcttgtg aagcgcatct tgaaactgg    29

<210> SEQ ID NO 11
<211> LENGTH: 47
<212> TYPE: DNA
<213> ORGANISM: Artificial Sequence
<220> FEATURE:
<223> OTHER INFORMATION: Synthetic primer

<400> SEQUENCE: 11
cgcgttagct tggaaatgac attgctaatg gtgacaaagc aacttta    47

<210> SEQ ID NO 12
<211> LENGTH: 47
<212> TYPE: DNA
<213> ORGANISM: Artificial Sequence
<220> FEATURE:
<223> OTHER INFORMATION: Synthetic oigonucleotide

<400> SEQUENCE: 12
gatctaaagt tgctttgtca ccattagcaa tgtcatttcc aagctaa    47

<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 13
gccatgatgg acttggagtt gccaccgcca    30

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 14
gccatgggtg aatcccaatg tgaaaataca    30

<210> SEQ ID NO 15
<211> LENGTH: 30
<212> TYPE: DNA
<213> ORGANISM: Artificial Sequence
<220> FEATURE:

<223> OTHER INFORMATION: Synthetic oligonucleotide

<400> SEQUENCE: 15
gtttttcttt gtatctggct tcttgctttt                              30

<210> SEQ ID NO 16
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 16
ccaccatgca gcccgaaccc aagcttagc                               29

<210> SEQ ID NO 17
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 17
aagcaaattg atcaacaaaa ctgtacctgc                              30

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
acaggtcctg gcatcttgtc                                         20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
agccactcag tcttggcagt                                         20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
cagtcgcctc cagagtttcc                                         20

<210> SEQ ID NO 21
<211> LENGTH: 21
<212> TYPE: DNA
<213> ORGANISM: Artificial Sequence
<220> FEATURE:
<223> OTHER INFORMATION: Synthetic primer

<400> SEQUENCE: 21
tacaaggagg ccatcaccag c                                       21

<210> SEQ ID NO 22

```
<211> LENGTH: 22
<212> TYPE: DNA
<213> ORGANISM: Artificial Sequence
<220> FEATURE:
<223> OTHER INFORMATION: Synthetic primer

<400> SEQUENCE: 22
ctgctaaact gttcattgta gg                                              22

<210> SEQ ID NO 23
<211> LENGTH: 19
<212> TYPE: DNA
<213> ORGANISM: Artificial Sequence
<220> FEATURE:
<223> OTHER INFORMATION: Synthetic primer

<400> SEQUENCE: 23
ctattgggtt ttacctgtg                                                  19

<210> SEQ ID NO 24
<211> LENGTH: 23
<212> TYPE: DNA
<213> ORGANISM: Artificial Sequence
<220> FEATURE:
<223> OTHER INFORMATION: Synthetic primer

<400> SEQUENCE: 24
gtcttcaggt gaacattcca agc                                             23

<210> SEQ ID NO 25
<211> LENGTH: 21
<212> TYPE: DNA
<213> ORGANISM: Artificial Sequence
<220> FEATURE:
<223> OTHER INFORMATION: Synthetic primer

<400> SEQUENCE: 25
tgttcttcag gggctccagt c                                               21

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
gtgtacagca ttggccacac                                                 20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
aaatgatggc ccacagaaag                                                 20
```

NEUROPROTECTIVE COMPOSITIONS AND METHODS

RELATED APPLICATIONS

This application claims the benefit and is a continuation of U.S. application Ser. No. 11/974,114, now U.S. Pat. 8,022, 246, filed on Oct. 10, 2007, which claims priority, under 35 U.S.C. §119(e), of: U.S. Provisional Application No. 60/850, 860, which was filed on Oct. 10, 2006, and U.S. Provisional Application No. 60/850,918, which was filed on Oct. 10, 2006, each of which are of same title and named Stuart A. Lipton and Takumi Satoh, as inventors. The entirety of the afore referenced applications and documents are expressly incorporated by reference herein.

STATEMENT OF GOVERNMENT RIGHTS

The invention was supported, at least in part, by a grant from the Government of the United States of America (grants no. P01 HD29587, R01 NS43242, and R01 EY05477 from the National Institutes of Health). The Government may have certain rights to the invention.

SEQUENCE LISTING

The instant application contains a Sequence Listing which has been submitted in ASCII format via EFS-Web and is hereby incorporated by reference in its entirety. Said ASCII copy, created on Apr. 17, 2012, is named BRN2040CT.txt and is 6 kilobytes in size.

FIELD OF THE INVENTION

The present inventions relates to the field of neuroprotection and treatment of conditions related to oxidative stress leading to neuronal injury and death.

BACKGROUND

Cellular antioxidants are crucial for reducing oxidative stress and preventing neuronal death. A recently elucidated pathway to induce antioxidant enzymes involves transcriptional activation through the antioxidant-responsive element (ARE) (Itoh et al., Mol. Cell. Biol. 24:36-45, 2004; Gong et al., Antioxid. Redox Signal. 4:249-257, 2002). In this case, electrophilic agents induce a set of genes encoding "phase 2" enzymes, including hemeoxygenase-1 (HO-1), NADPH quinine oxidoreductase 1, and γ-glutamyl cysteine ligase (γ-GCL, also known as γ-glutamate cysteine ligase or γ-glutamyl cysteine ligase [γ-GCS]). These enzymes provide efficient cytoprotection, in part, by regulating the intracellular redox state (Itoh et al., Mol. Cell. Biol. 24:36-45, 2004; Gong et al., Antioxid. Redox Signal. 4:249-257, 2002).

The ARE is a cis-acting element essential for transcriptional activation of phase 2 genes by electrophiles (Itoh et al., Mol. Cell. Biol. 24:36-45, 2004; Gong et al., Antioxid. Redox Signal. 4:249-257, 2002). The transcription factor Nfr2 complexes with Maf family proteins to transactivate the ARE. Under basal conditions, the cytosolic regulatory protein Keap1 binds tightly to Nrf2, retaining it in the cytoplasm (Itoh et al., Mol. Cell. Biol. 24:36-45, 2004; Gong et al., Antioxid. Redox Signal. 4:249-257, 2002). In this regard, the action of Keap1 is analogous to that of IκB, preventing activation and translocation of the transcription factor NF-κB (Itoh et al., Mol. Cell. Biol. 24:36-45, 2004; Gong et al., Antioxid. Redox Signal. 4:249-257, 2002). In the case of Keap1, electrophiles make a Michael adduct with critical cysteine residues in this regulatory protein, causing the liberation of Nrf2 and allowing it to translocate into the nucleus (Itoh et al., Mol. Cell. Biol. 24:36-45, 2004; Gong et al., Antioxid. Redox Signal. 4:249-257, 2002).

Among the phase 2 enzymes, HO-1 has attracted special attention because of its therapeutic effects against neurodegenerative diseases (Maines and Panahian, in *Hypoxia: From Genes to the Bedside*, eds. Roach et al. (New York: Kluwer), 2001, pp. 249-272; Stocker et al., Science 235:1043-1046, 1987).

HO-1 oxidatively cleaves heme to biliverdin, forms CO, and releases the chelated $Fe^{2+}$ (Maines and Panahian, in *Hypoxia: From Genes to the Bedside*, eds. Roach et al. (New York: Kluwer), 2001, pp. 249-272). Bilirubin (a reduction product of biliverdin) serves as a potent radical scavenger (Stocker et al., Science 235:1043-1046, 1987) and protects neuronal ells against oxidative stress at nanomolar concentrations (Dore et al., Proc. Natl. Acad. Sci. USA 96:2445-2450, 1999). Studies using gene-knockout and transgenic mice have confirmed the biological significance of HO-1 as a cellular antioxidant (Poss and Tanegawa, Proc. Natl. Acad. Sci. USA 94:10925-10930, 1997). HO-1 has been proposed to play an obligatory role in endogenous defense against oxidative stress, because cells from $HO-1^{-/-}$ mice are highly susceptible to oxidative insults (Poss and Tanegawa, Proc. Natl. Acad. Sci. USA 94:10925-10930, 1997). The significance of HO-1 in terms of drug development against neurodegenerative diseases is based on two facts: (i) HO produces several antioxidative compounds, including biliverdin and bilirubin (Dore et al., Proc. Natl. Acad. Sci. USA 96:2445-2450, 1999), and (ii) the induction of HO-1 can be regulated by various compounds (Satoh et al., Eur. J. Neurosci. 17:2249-2255, 2003). Thus, it has been proposed that an inducer of HO-1 in neurons could represent an efficient neuroprotective compound (Maines and Panahian, in *Hypoxia: From Genes to the Bedside*, eds. Roach et al. (New York: Kluwer), 2001, pp. 249-272; Dore et al., Proc. Natl. Acad. Sci. USA 96:2445-2450, 1999; Satoh et al., Eur. J. Neurosci. 17:2249-2255, 2003).

SUMMARY OF THE INVENTION

We have discovered neuroprotective electrophilic compounds, and prodrug forms of such compounds, that modulate the Keap1-Nrf2 pathway, leading to activation of the HO-1 promoter by Nrf2. Induction of HO-1 protein is known to play an important neuroprotective role against excitotoxicity and brain ischemia.

According to one embodiment of the invention, compositions are provided that comprise a neuroprotective amount of an electrophilic compound, or a pharmaceutically acceptable prodrug, salt or solvate thereof, wherein the electrophilic compound causes dissociation of Nrf2 from a Keap1/Nrf2 complex in a cell of a mammal, such as, for example, an neuron. According to another embodiment, the electrophilic compound binds to Keap1, causing dissociation of Nrf2 from the Keap1/Nrf2 complex. According to another embodiment, the electrophilic compound increases expression of a phase 2 enzyme in the cell, including but not limited to HO-1. According to another embodiment, the electrophilic compound accumulates in nerve cells, such as neurons or astrocytes or both. According to another embodiment, the electrophilic compound is lipophilic. According to another embodiment, the electrophilic compound is actively transported into the cell. According to another embodiment the composition further comprises a pharmaceutically acceptable carrier.

According to another embodiment of such compositions, the electrophilic compound causes dissociation of Nrf2 from the Keap1/Nrf2 complex without substantially reducing GSH levels in the cell.

According to another embodiment of such compositions, the electrophilic compound is an enone, including but not limited to curcumin, or a dienone compound, including but not limited to an NEPP such as, for example, NEPP6 or NEPP11.

According to another embodiment, said electrophilic compound, or pharmaceutically acceptable prodrug, salt or solvate thereof, is a compound of Formula I, which has a core benzene ring:

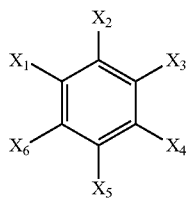

Formula I wherein:

$X_1$, $X_2$, $X_3$, $X_4$, $X_5$ and $X_6$ are each independently H, OH, alkyl or Y, provided that at least two of $X_1$-$X_6$ are OH and at least one of $X_1$-$X_6$ is Y;

Y is B—C-D or C—B-D or C—B—C-D, any of which may be attached to the core benzene ring to form a fused ring;

B is selected from the group consisting of null, carbonyl, carboxy, ether, sulfanyl, amino, —NHC(O)— and —C(O)NH—, any of which is optionally substituted;

C is selected from the group consisting of null, alkyl, cycloalkyl, alkenyl, cycloalkenyl, aryl, arylalkyl, and arylalkenyl, any of which is optionally substituted, and which may be attached to the core benzene ring so as to form a fused ring; and D is selected from the group consisting of null, carboxy, benzoic acid, hydroxybenzoic acid, $SO_3H$, $PO_3$, $NO_3$, $NO_2$, NO, amino, hydroxyl, and ether and ester derivatives thereof; and ether and ester derivatives thereof.

According to another embodiment, said electrophilic compound, or pharmaceutically acceptable prodrug, salt or solvate thereof, is a compound of Formula I as described above and $X_1$, $X_2$, $X_3$, $X_4$, $X_5$ and $X_6$ are each independently H, hydroxy, alkyl or Y, provided that two of $X_1$-$X_6$ are hydroxy (para and ortho configurations of the hydroxy groups are preferred, and the para configuration is more preferred) and one of $X_1$-$X_6$ is Y.

According to another embodiment, said electrophilic compound, or pharmaceutically acceptable prodrug, salt or solvate thereof, is a compound of Formula I as described above and $X_1$, $X_2$, $X_3$, $X_4$, $X_5$ and $X_6$ are each independently H, OH, alkyl or Y, provided that two of $X_1$-$X_6$ are hydroxy in a para or ortho configuration and one of $X_1$-$X_6$ is Y (that is, the compounds include a p- or o-dihydroxybenzene ring structure monosubstituted with side chain Y).

According to another embodiment, said electrophilic compound, or pharmaceutically acceptable prodrug, salt or solvate thereof, is such a compound of Formula I wherein: $X_1$, $X_2$, $X_3$, $X_4$, $X_5$ and $X_6$ are each independently H, OH, alkyl or Y, provided that two of $X_1$-$X_6$ are hydroxy in a para configuration and one of $X_1$-$X_6$ is Y (that is, the compounds include a p-dihydroxybenzene ring structure monosubstituted with side chain Y) and D is selected from the group consisting of carboxy, benzoic acid, hydroxybenzoic acid, $SO_3H$, $PO_3$, $NO_3$, $NO_2$, NO, amino, hydroxy, and ether and ester derivatives thereof. Preferably: Y is B—C-D; D is carboxy or an ester derivative thereof; and B is null or carbonyl.

According to another embodiment, said electrophilic compound, or pharmaceutically acceptable prodrug, salt or solvate thereof, is a compound of Formula II or Formula III:

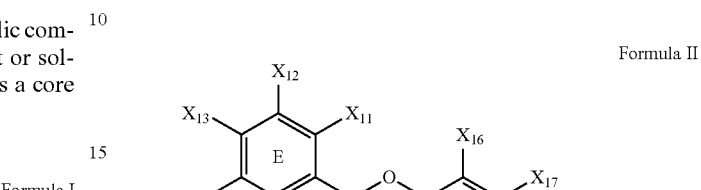

Formula II

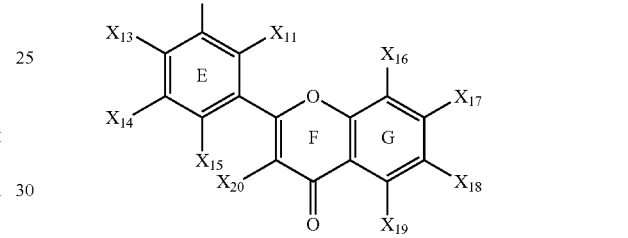

Formula III

Wherein $X_{11}$, $X_{12}$, $X_{13}$, $X_{14}$, $X_{15}$, $X_{16}$, $X_{17}$, $X_{18}$, $X_{19}$, and $X_{20}$, are each independently H, OH, or Y, provided that at least two of $X_{11}$-$X_{20}$ are OH; Y is B—C-D or C—B-D or C—B—C-D, any of which may be attached to a ring carbon to form a fused ring; B is selected from the group consisting of null, carbonyl, carboxy, ether, sulfanyl, amino, —NHC(O)— and —C(O)NH—, any of which is optionally substituted; C is selected from the group consisting of null, alkyl, cycloalkyl, alkenyl, cycloalkenyl, aryl, arylalkyl, and arylalkenyl, any of which is optionally substituted, and which may be attached to a ring carbon so as to form a fused ring; and D is selected from the group consisting of null, carboxy, benzoic acid, hydroxybenzoic acid, $SO_3H$, $PO_3$, $NO_3$, $NO_2$, NO, amino, hydroxyl; and ether and ester derivatives thereof. According to another embodiment, said electrophilic compound, or pharmaceutically acceptable prodrug, salt or solvate thereof, is such a compound of Formula II or Formula III, wherein $X_{11}$, $X_{12}$, $X_{13}$, $X_{14}$, $X_{15}$, $X_{16}$, $X_{17}$, $X_{18}$, $X_{19}$, and $X_{20}$, are each independently H, OH, or Y, provided that two of $X_{11}$-$X_{15}$ are OH, or two of $X_{16}$-$X_{19}$ are OH, or two of $X_{11}$-$X_{15}$ are OH and two of $X_{16}$-$X_{19}$ are OH. Preferably, at least one of $X_{11}$-$X_{20}$ is Y. Preferably Y is hydrophilic or null, and more preferably hydrophilic. Preferably said compound of Formula II or Formula III comprises an E ring comprising two OH groups in para or ortho configuration, and more preferably in para configuration. Preferably said compound of Formula II or Formula III comprises a G ring comprising two OH groups in para or ortho configuration, and more preferably in para configuration.

According to another embodiment, said electrophilic compound, or pharmaceutically acceptable prodrug, salt or solvate thereof, is a compound of Formula IV, Formula V or Formula VI:

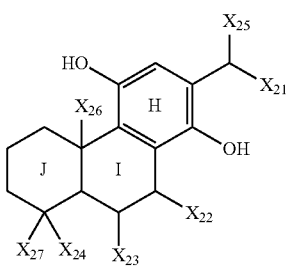

Formula IV

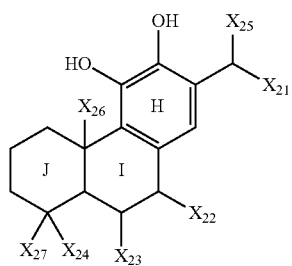

Formula V

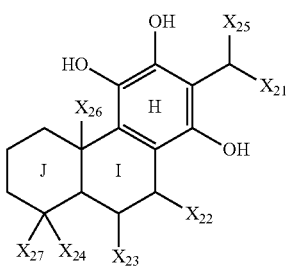

Formula VI wherein: $X_{21}$, $X_{22}$, $X_{23}$, $X_{24}$, $X_{25}$, $X_{26}$ and $X_{27}$ are each independently H, OH, oxo, or Y; Y is B—C-D or C—B-D or C—B—C-D, any of which may be attached to a ring carbon to form a fused ring; B is selected from the group consisting of null, carbonyl, carboxy, ether, sulfanyl, amino, —NHC(O)— and —C(O)NH—, any of which is optionally substituted; C is selected from the group consisting of null, alkyl, cycloalkyl, alkenyl, cycloalkenyl, aryl, arylalkyl, and arylalkenyl, any of which is optionally substituted, and which may be attached to a ring carbon so as to form a fused ring; and D is selected from the group consisting of null, carboxy, benzoic acid, hydroxybenzoic acid, $SO_3H$, $PO_3$, $NO_3$, $NO_2$, NO, amino, hydroxyl; and ether and ester derivatives thereof. Preferably B is null. Preferably said electrophilic compound, or pharmaceutically acceptable prodrug, salt or solvate thereof, is a compound of Formula IV or Formula V, more preferably a compound of Formula IV. Preferably $X_{21}$ and $X_{24}$ are each independently methyl, carboxy, —C(O)OCH$_3$, CH$_2$OH, or CH$_2$OC(O)CH$_3$. Preferably $X_{22}$ and $X_{23}$ are each independently H, OH, oxo, or —OCH$_3$, and more preferably at least one of $X_{22}$ and $X_{23}$ is OH or oxo. Preferably $X_{25}$ or $X_{27}$ or both are methyl. Preferably at least one of $X_{21}$, $X_{26}$ or $X_{27}$ is carboxy, and more preferably, one of $X_{21}$ or $X_{24}$ is CH$_3$ and the other is selected from the group consisting of carboxy, —C(O)OCH$_3$, —CH$_2$OH, and —CH$_2$OC(O)CH$_3$. The R enantiomer of $X_{26}$ is preferred.

According to another embodiment of such compositions, said electrophilic compound, or pharmaceutically acceptable prodrug, salt or solvate thereof, is selected from the group consisting of TBHQ; an NEPP; para L-dopa; Benzeneacetic acid, 2,5-dihydroxy-α-octylidene-, (Z)-(9CI); Benzenedecanoic acid, 2,5-dihydroxy-t-oxo-(9CI); Benzeneundecanoic acid, 2,5-dihydroxy-(9CI); Benzenebutanoic acid, 2,5-dihydroxy-γ-oxo-β-phenyl-(9CI); Benzenebutanoic acid, 2,5-dihydroxy-β-(4-methylphenyl)-γ-oxo-(9CI); Benzoic acid, 2-[2-(2,5-dihydroxyphenyl)ethyl]-6-hydroxy-(9CI); Benzoic acid, 5-[2-(2,5-dihydroxyphenyl)ethyl]-2-hydroxy-(9CI); Benzoic acid, 4-[2-(2,5-dihydroxyphenyl)-2-oxoethyl]-(9CI); Benzoic acid, 3-[[(2,5-dihydroxyphenyl)methyl]amino]-(9CI); [1,1'-Biphenyl]-4-carboxylic acid, 2',5'-dihydroxy-(9CI); Pentanoic acid, 5-(2,5-dihydroxyphenoxy)-2,2-dimethyl-(9CI); Octanoic acid, 8-[(2,5-dihydroxybenzoyl)amino]-(9CI); Benzenebutanoic acid, 2,5-dihydroxy-γ-phenyl-(9CI); 5,9-Undecadienoic acid, 2-[2-(2,5-dihydroxyphenyl)ethylidene]-11-hydroxy-6,10-dimethyl-, (2Z,5E,9E)-(9CI); 5,9-Undecadienoic acid, 2-[2-(2,5-dihydroxyphenyl)ethylidene]-6,10-dimethyl (2Z, 5E)-(9CI); Benzenebutanoic acid, α-[(3E)-4,8-dimethyl-3,7-nonadienyl]-2,5-dihydroxy-γ-oxo-, (+)-(9CI); 2,6-Octadienoic acid, 8-(2,5-dihydroxyphenyl)-2,6-dimethyl-8-oxo-, (2E,6E)-(9CI); an ester of 3-(3,4)-dihydroxyphenyl]-2-propenoic acid (caffeic acid); and an ester of 3-(2,5)-dihydroxyphenyl]-2-propenoic acid.

According to another embodiment of such compositions, the composition comprises said prodrug of said electrophilic compound. According to one embodiment, the prodrug is a terpenoid or flavonoid compound such as, for example, carnosic acid, para carnosic acid, or a carnosic acid derivative. According to another embodiment the cell is under oxidative stress and said prodrug is oxidized in the cell to produce the electrophilic compound.

According to another embodiment of such compositions, the composition comprises an amount of said electrophilic compound, prodrug, salt or solvate thereof that is effective for treating a member of the group consisting of a neurological disorder, an ophthalmological disorder, and a combination thereof in a mammal, including, without limitation, a human. According to another embodiment the neurological disorder, an ophthalmological disorder, or a combination thereof results from at least one member of the group consisting of trauma, ischemia, and hypoxia. According to another embodiment the neurological disorder, ophthalmological disorder, or combination thereof is selected from the group consisting of painful neuropathy, neuropathic pain, diabetic neuropathy, drug dependence, drug addition, drug withdrawal, nicotine withdrawal, opiate tolerance, opiate withdrawal, depression, anxiety, a movement disorder, tardive dyskinesia, a cerebral infection that disrupts the blood-brain barrier, meningitis, meningoencephalitis, stroke, hypoglycemia, cardiac arrest, spinal cord trauma, head trauma, perinatal hypoxia, cardiac arrest, hypoglycemic neuronal damage, glaucoma, retinal ischemia, ischemic optic neuropathy, macular degeneration, multiple sclerosis, sequalae of hyperhomocystinemia, convulsion, pain, schizophrenia, muscle spasm, migraine headache, urinary incontinence, emesis, brain edema, tardive dyskinesia, AIDS-induced dementia, ocular damage, retinopathy, a cognitive disorder, and a neuronal injury associated with HIV infection. According to another embodiment the neurological disorder, ophthalmological disorder, or combination thereof is selected from the group consisting of epilepsy, Alzheimer's disease, vascular (multi-infarct) dementia, Huntington's disease, Parkinsonism, multiple sclerosis, amyotrophic lateral sclerosis, and minimal cognitive impairment (MCI).

According to another embodiment of such compositions, the composition comprises an amount of such an electrophilic compound, prodrug, salt or solvate thereof that is effective for reducing or slowing aging or a symptom thereof in a mammal.

According to another embodiment of such compositions, the composition comprises a neuroprotective amount of an electrophilic compound, or a pharmaceutically acceptable prodrug, salt or solvate thereof, wherein the electrophilic compound binds to Keap1 in a cell of a mammal, causing dissociation of Nrf2 from the Keap1/Nrf2 complex and increasing expression of a phase 2 enzyme in the cell without substantially reducing GSH levels in the cell.

According to another embodiment of the invention, methods are provided for preventing or delaying injury, damage or death of a cell of a mammal (due to processes including but not limited to apoptosis, necrosis or autophagy) comprising administering to the cell any of the compositions described above. According to one such embodiment, the method comprises administering the composition to the cell in vitro. According to one such embodiment, the method comprises administering the composition to the cell in vivo, i.e., administering the composition to the mammal.

According to another embodiment of the invention, methods are provided for treating a neurological disorder, an ophthalmological disorder, or a combination thereof in a mammal in need of such treatment, such methods comprising administering to the mammal any of the compositions described above.

According to another embodiment of the invention, compounds are provided, or pharmaceutically acceptable prodrugs, salts or solvates thereof, of Formula IV:

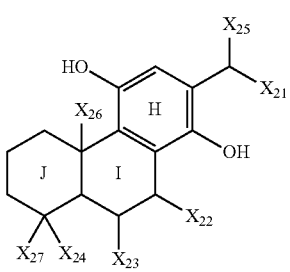

Formula IV wherein: $X_{21}$, $X_{22}$, $X_{23}$, $X_{24}$, $X_{25}$, $X_{26}$ and $X_{27}$ are each independently H, OH, oxo, or Y; Y is B—C-D or C—B-D or C—B—C-D, any of which may be attached to a ring carbon to form a fused ring; B is selected from the group consisting of null, carbonyl, carboxy, ether, sulfanyl, amino, —NHC(O)— and —C(O)NH—, any of which is optionally substituted; C is selected from the group consisting of null, alkyl, cycloalkyl, alkenyl, cycloalkenyl, aryl, arylalkyl, and arylalkenyl, any of which is optionally substituted, and which may be attached to a ring carbon so as to form a fused ring; and D is selected from the group consisting of null, carboxy, benzoic acid, hydroxybenzoic acid, $SO_3H$, $PO_3$, $NO_3$, $NO_2$, NO, amino, hydroxyl; and ether and ester derivatives thereof. Preferably B is null. Preferably $X_{21}$ and $X_{24}$ are each independently methyl, carboxy, —C(O)OCH$_3$, CH$_2$OH, or CH$_2$OC(O)CH$_3$. Preferably $X_{22}$ and $X_{23}$ are each independently H, OH, oxo, or —OCH$_3$, and more preferably at least one of $X_{22}$ and $X_{23}$ is OH or oxo. Preferably $X_{25}$ or $X_{27}$ or both are methyl. Preferably at least one of $X_{21}$, $X_{26}$ or $X_{27}$ is carboxy, and more preferably, one of $X_{21}$ or $X_{24}$ is CH$_3$ and the other is selected from the group consisting of carboxy, —C(O)OCH$_3$, —CH$_2$OH, and —CH$_2$OC(O)CH$_3$. The R enantiomer of $X_{26}$ is preferred.

According to another embodiment of the invention, pharmaceutical compositions are provided comprising: (a) a neuroprotective amount of a compound selected from member of the group consisting a compound of Formula IV as described above, para carnosic acid, para L-dopa, para caffeic acid or a pharmaceutically acceptable prodrug, salt or solvate thereof; and (b) a pharmaceutically acceptable carrier.

According to another embodiment of the invention, methods are provided for identifying a neuroprotective electrophilic compound, or a pharmaceutically acceptable prodrug, salt or solvate thereof, such methods comprising administering to a cell (in vitro or in vivo) a composition comprising said electrophilic compound, prodrug, salt or solvate thereof and determining whether administration of the composition causes dissociation of Nrf2 from the Keap1/Nrf2 complex in the cell. According to one embodiment, such methods comprise determining whether the electrophilic compound binds to Keap1. According to another embodiment, such methods comprise determining whether administration of the composition causes transcriptional activation by Nrf2 in the cell. According to another embodiment, such methods comprise determining whether administration of the composition causes an increase in expression of a phase 2 enzyme, including but not limited to HO-1, in the cell. According to another embodiment, such methods comprise determining whether administration of the composition decreases or delays stress-induced death of the cell (due, for example, to apoptosis, necrosis or autophagy). According to another embodiment, such methods comprise determining whether administration of the composition protects a test animal comprising the cell against cerebral ischemia/reperfusion injury in a suitable in vivo assay. According to another embodiment, such methods comprise determining whether the electrophilic compound accumulates in nerve cells such as, for example, neurons or astrocytes or both. According to another embodiment, such methods comprise determining whether administration of the composition causes dissociation of Nrf2 from the Keap1/Nrf2 complex without substantially reducing GSH levels in the cell.

According to another embodiment of the invention, an electrophilic compound that causes dissociation of Nrf2 from a Keap1/Nrf2 complex in a cell of a patient, or a pharmaceutically acceptable prodrug, salt or solvate thereof, is used to prepare a medicament to treat a neurological disorder, an ophthalmological disorder, or a combination thereof.

The foregoing and other aspects of the invention will become more apparent from the following detailed description, accompanying drawings, and the claims.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below.

DETAILED DESCRIPTION OF THE INVENTION

Definitions

As described in greater detail below, compositions and related methods are provided that comprise neuroprotective electrophiles that activate an "electrophile counterattack" by neurons that eliminates not only the electrophiles themselves but also free radicals such as reactive oxygen species (ROS), thus preventing neurodegeneration. Neuroprotection by such electrophilic substances entails a transcription-based mechanism involving the Keap1/Nrf2 signaling pathway and the induction of phase 2 genes, which encode enzymes that represent a coordinated response to electrophiles that includes increasing intracellular levels of neuroprotective substances such as γ-GCL and HO-1. Such compounds also prevent, reduce or delay damage due to free radical-mediated events in the cell. According to another embodiment, such methods comprise determining whether administration of the composition decreases or delays stress-induced cell damage, injury, or death (e.g., from apoptosis, necrosis or autophagy) of the cell. Also provided are compositions and related methods of use that comprise prodrug forms of such neuroprotective electrophiles (or "pro-electrophiles") that are metabolized within the body of a patient to produce such electrophilic compounds.

Figure 1:
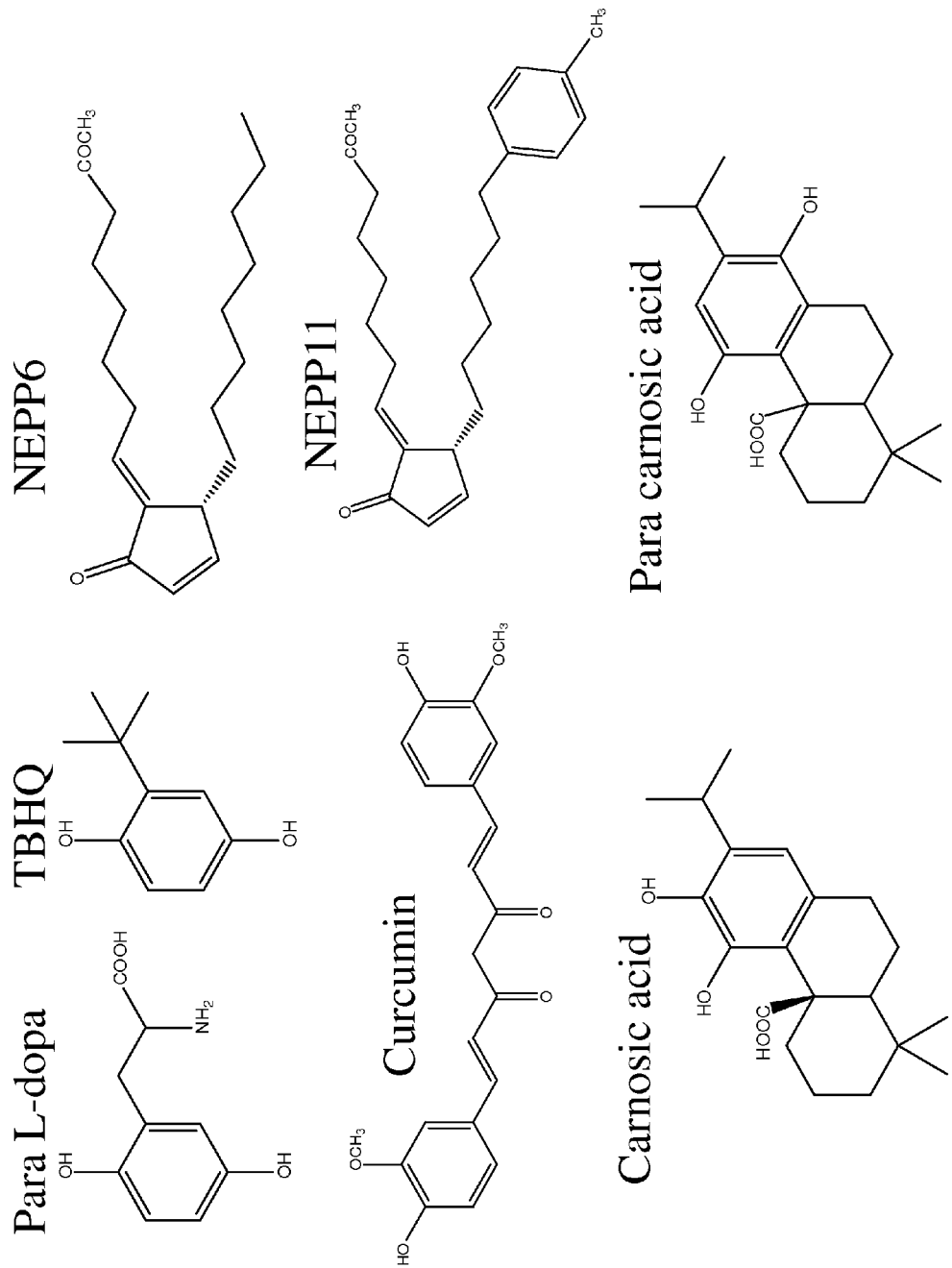
FIG. 1 shows various selected neuroprotective electrophilic or proelectrophilic compounds: para L-dopa, TBHQ, NEPP 6, NEPP11, curcumin, carnosic acid and para carnosic acid.

FIG. 1 shows examples of neuroprotective electrophilic compounds (para L-dopa, TBHQ, NEPP6, NEPP11, and curcumin) and proelectrophilic compounds (carnosic acid (CA), para carnosic acid, and carnosic acid derivatives).

According to one embodiment of the invention, neuroprotective electrophilic compounds according to the invention are enone-type electrophilic compounds, which include but are not limited to enones and dienones (FIG. 2B). An example of an enone is curcumin. Examples of dienones include cross-conjugated dienones such as neurite outgrowth-promoting prostaglandins (NEPPs), including, but not limited to, NEPP 6 and NEPP11. Dienones are preferred.

According to another embodiment of the invention, neuroprotective electrophilic compounds according to the invention are catechol-type electrophilic compounds (FIG. 2A). Examples of other catechol-type neuroprotective electrophiles according to the invention include but are not limited to: tert-butyl hydroquinone (TBHQ); para L-dopa; and esters of 3-(3,4)-dihydroxyphenyl]-2-propenoic acid (caffeic acid) or 3-(2,5)-dihydroxyphenyl]-2-propenoic acid that permit the compound to pass through cell membranes, including, but not limited to, methyl and ethyl esters.

According to one embodiment of the invention, catechol-type neuroprotective electrophilic compounds, or pharmaceutically acceptable prodrugs, salts or solvates thereof, according to the invention have structural formulae I:

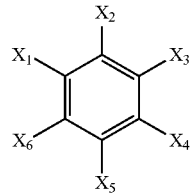

Formula I wherein:

$X_1$, $X_2$, $X_3$, $X_4$, $X_5$ and $X_6$ are each independently H, OH, alkyl or Y, provided that at least two of $X_1$-$X_6$ are OH and at least one of $X_1$-$X_6$ is Y;

Y is B—C-D or C—B-D or C—B—C-D, any of which may be attached to the core benzene ring to form a fused ring;

B is selected from the group consisting of null, carbonyl, carboxy, ether, sulfanyl, amino, —NHC(O)— and —C(O)NH—, any of which is optionally substituted;

C is selected from the group consisting of null, alkyl, cycloalkyl, alkenyl, cycloalkenyl, aryl, arylalkyl, and arylalkenyl, any of which is optionally substituted, and which may be attached to the core benzene ring so as to form a fused ring; and D is selected from the group consisting of null, carboxy, benzoic acid, hydroxybenzoic acid, $SO_3H$, $PO_3$, $NO_3$, $NO_2$, NO, amino, hydroxyl, and ether and ester derivatives thereof.

In another embodiment, such compounds have structural formulae I, wherein: $X_1$, $X_2$, $X_3$, $X_4$, $X_5$ and $X_6$ are each independently H, OH, alkyl or Y, provided that two of $X_1$-$X_6$ are OH and one of $X_1$-$X_6$ is Y (that is, the compounds have a para, ortho or meta dihydroxybenzene ring structure monosubstituted with side chain Y); Y is B—C-D or C—B-D or C—B—C-D any of which may be attached to the core benzene ring to form a fused ring; B is selected from the group consisting of null, carbonyl, carboxy, ether, sulfanyl, amino, —NHC(O)— and —C(O)NH—, any of which is optionally substituted; C is selected from the group consisting of null, alkyl, cycloalkyl, alkenyl, cycloalkenyl, aryl, arylalkyl, and arylalkenyl, any of which is optionally substituted, and which may be attached to the dihydroxybenzene ring so as to form a fused ring; and D is selected from the group consisting of null, carboxy, benzoic acid, hydroxybenzoic acid, $SO_3H$, $PO_3$, $NO_3$, $NO_2$, NO, amino, hydroxyl, and ether and ester derivatives thereof.

In another embodiment, such compounds have structural formulae I, wherein: $X_1$, $X_2$, $X_3$, $X_4$, $X_5$ and $X_6$ are each independently H, OH, alkyl or Y, provided that two of $X_1$-$X_6$ are OH in a para configuration and one of $X_1$-$X_6$ is Y (that is, the compounds include a p-dihydroxybenzene ring structure monosubstituted with side chain Y); Y is B—C-D or C—B-D or C—B—C-D, any of which may be attached to the core benzene ring to form a fused ring; B is selected from the group consisting of null, carbonyl, carboxy, ether, sulfanyl, amino, —NHC(O)— and —C(O)NH—, any of which is optionally substituted; C is selected from the group consisting of null, alkyl, cycloalkyl, alkenyl, cycloalkenyl, aryl, arylalkyl, and arylalkenyl, any of which is optionally substituted, and which may be attached to the core benzene ring so as to form a fused ring; and D is selected from the group consisting of null, carboxy, benzoic acid, hydroxybenzoic acid, $SO_3H$, $PO_3$, $NO_3$, $NO_2$, NO, amino, hydroxyl, and ether and ester derivatives thereof.

In another embodiment, such compounds have structural formulae I, wherein: $X_1$, $X_2$, $X_3$, $X_4$, $X_5$ and $X_6$ are each independently H, OH, alkyl or Y, provided that two of $X_1$-$X_6$ are OH in a para configuration and one of $X_1$-$X_6$ is Y (that is, the compounds include a p-dihydroxybenzene ring structure monosubstituted with side chain Y); Y is B—C-D or C—B-D or C—B—C-D any of which may be attached to the core benzene ring to form a fused ring; B is selected from the group consisting of null, carbonyl, carboxy, ether, sulfanyl, amino, —NHC(O)— and —C(O)NH—, any of which is optionally substituted; C is selected from the group consisting of null, alkyl, cycloalkyl, heteroalkyl, alkenyl, cycloalkenyl, aryl, arylalkyl, and arylalkenyl, any of which is optionally substituted, and which may be attached to the dihydroxybenzene ring so as to form a fused ring; and D is selected from the group consisting of carboxy, benzoic acid, hydroxybenzoic acid, $SO_3H$, $PO_3$, $NO_3$, $NO_2$, NO, amino, hydroxyl, and ether and ester derivatives thereof.

Preferably Y is B—C-D.

Preferably B is null or carbonyl.

Preferably D is carboxy or an ester derivative thereof.

According to another embodiment of the invention, catechol-type neuroprotective electrophilic compounds, or pharmaceutically acceptable prodrugs, salts or solvates thereof, according to the invention have a core flavonoid structure according to structural Formulae II or Formula III:

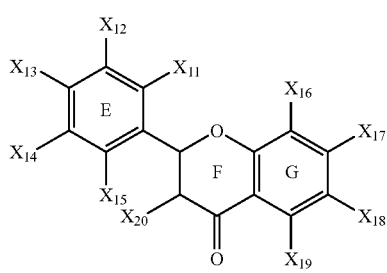

Formula II

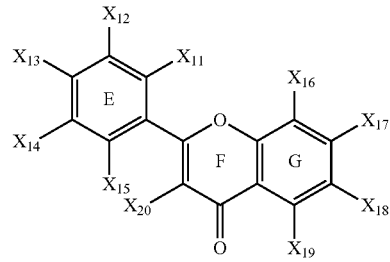

Formula III wherein:
$X_{11}$, $X_{12}$, $X_{13}$, $X_{14}$, $X_{15}$, $X_{16}$, $X_{17}$, $X_{18}$, $X_{19}$, and $X_{20}$, are each independently H, OH, or Y, provided that at least two of $X_{11}$-$X_{20}$ are OH;

Y is B—C-D or C—B-D or C—B—C-D, any of which may be attached to a ring carbon to form a fused ring;

B is selected from the group consisting of null, carbonyl, carboxy, ether, sulfanyl, amino, —NHC(O)— and —C(O)NH—, any of which is optionally substituted;

C is selected from the group consisting of null, alkyl, cycloalkyl, alkenyl, cycloalkenyl, aryl, arylalkyl, and arylalkenyl, any of which is optionally substituted, and which may be attached to a ring carbon so as to form a fused ring; and D is selected from the group consisting of null, carboxy, benzoic acid, hydroxybenzoic acid, $SO_3H$, $PO_3$, $NO_3$, $NO_2$, NO, amino, hydroxyl;

and ether and ester derivatives thereof.

In another embodiment, such compounds have structural formulae II or III, wherein $X_{11}$, $X_{12}$, $X_{13}$, $X_{14}$, $X_{15}$, $X_{16}$, $X_{17}$, $X_{18}$, $X_{19}$, and $X_{20}$, are each independently H, OH, or Y, provided that two of $X_{11}$-$X_{15}$ are OH (that is, ring E has two OH groups in para, ortho, or meta configuration), or two of $X_{16}$-$X_{19}$ are OH (that is, ring G has two OH groups in para, ortho, or meta configuration) or two of $X_{11}$-$X_{15}$ are OH and two of $X_{16}$-$X_{19}$ are OH.

Preferably at least one of $X_{11}$-$X_{20}$ is Y. It is preferable that Y is hydrophilic or null, most preferably hydrophilic.

Preferably, for compounds having two OH groups on ring E, the OH groups are in para or ortho configuration, more preferably in para configuration. Similarly, it is preferable for compounds having two OH groups on ring G that the OH groups are in para or ortho configuration, more preferably in para configuration. Most preferable are compounds having two OH groups in para configuration on ring E.

One example of a flavonoid compound according to the invention is the compound below.

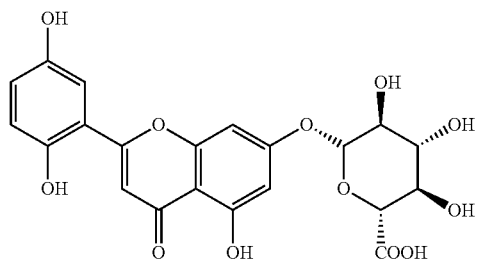

Other examples include, without limitation (CA Index Names): β-D-glucopyranosiduronic acid, (2S)-2-(2,5-dihydroxyphenyl)-3,4-dihydro-5-hydroxy-4-oxo-2H-1-benzopyran-7-yl; and β-D-glucopyranosiduronic acid, 2-(2,5-dihydroxyphenyl)-5-hydroxy-4-oxo-4H-1-benzopyran-7-yl.

According to another embodiment of the invention, neuroprotective pro-electrophilic compounds, or pharmaceutically acceptable salts or solvates thereof, according to the invention are carnosic acid (CA) derivatives having structural Formula IV, Formula V, or Formula VI:

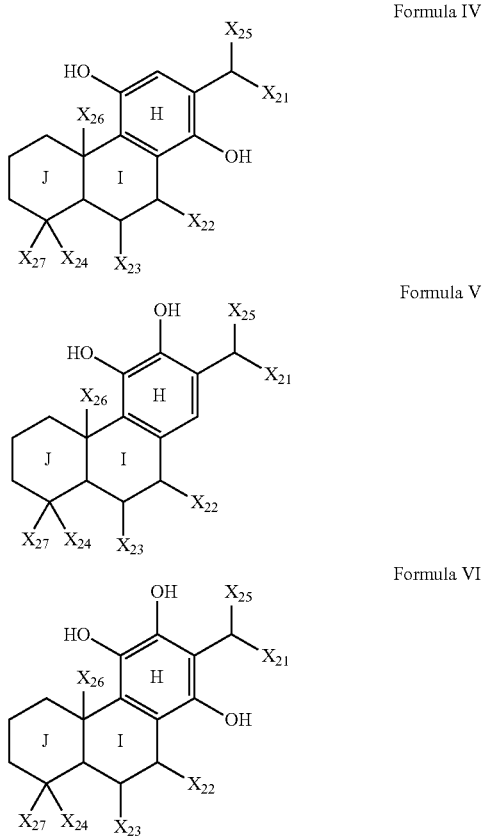

Formula IV

Formula V

Formula VI wherein:

$X_{21}$, $X_{22}$, $X_{23}$, $X_{24}$, $X_{25}$, $X_{26}$ and $X_{27}$ are each independently H, OH, oxo (=O), or Y;

Y is B—C-D or C—B-D or C—B—C-D, any of which may be attached to a ring carbon to form a fused ring;

B is selected from the group consisting of null, carbonyl, carboxy, ether, sulfanyl, amino, —NHC(O)— and —C(O)NH—, any of which is optionally substituted;

C is selected from the group consisting of null, alkyl, cycloalkyl, alkenyl, cycloalkenyl, aryl, arylalkyl, and arylalkenyl, any of which is optionally substituted, and which may be attached to a ring carbon so as to form a fused ring; and D is selected from the group consisting of null, carboxy, benzoic acid, hydroxybenzoic acid, $SO_3H$, $PO_3$, $NO_3$, $NO_2$, NO, amino, hydroxyl; and ether and ester derivatives thereof.

Preferably, B is null. Compounds of Formula IV (two OH groups as shown on ring H are in para configuration) and Formula V (two OH groups as shown on ring H are in ortho configuration), are preferred, and compounds of Formula IV are more preferred. Preferably $X_{21}$ and $X_{24}$ are each independently methyl, carboxy, —C(O)OCH$_3$, CH$_2$OH, or CH$_2$OC(O)CH$_3$. Preferably $X_{22}$ and $X_{23}$ are each independently H, OH, oxo (=O), or —OCH$_3$. $X_{25}$ and $X_{27}$ are preferably methyl. Preferably, at least one of $X_{21}$, $X_{26}$ or $X_{27}$ is carboxy, and more preferably one of $X_{21}$ and $X_{24}$ is CH$_3$ and the other is carboxy, —C(O)OCH$_3$, —CH$_2$OH, or —CH$_2$OC(O)CH$_3$, and at least one of $X_{22}$ and $X_{23}$ is hydroxy or oxo. The R enantiomer of $X_{26}$ is preferred to the S enantiomer. The compounds of Formulae IV, V and VI should be understood to include, for example, carnosol and carnosol derivatives (i.e., $X_{26}$ is Y, wherein B and C are null and D is carboxy, and the carboxy group is attached to the same ring carbon as $X_{22}$) having similar substituents to those described above.

Figure 3:
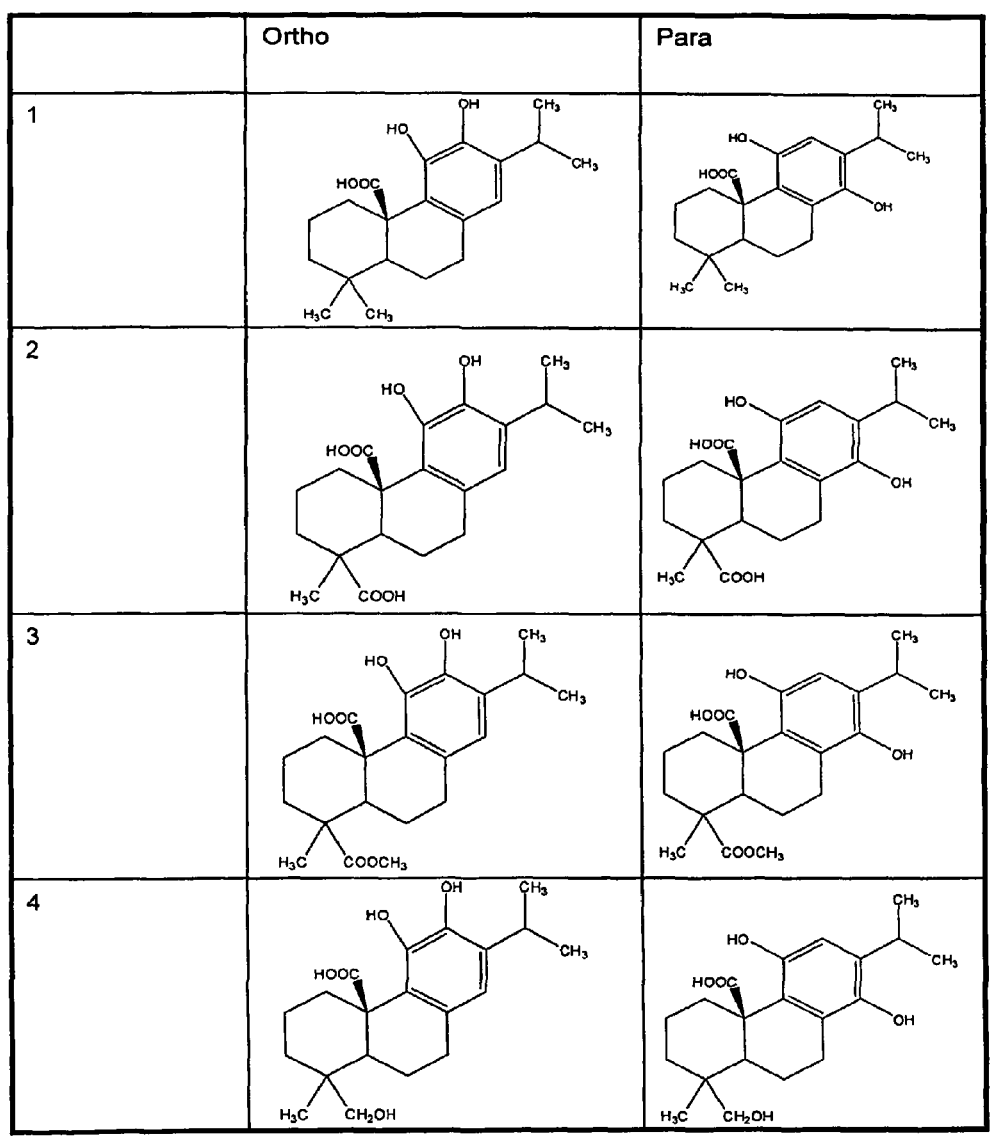
FIG. 3 shows the structure of carnosic acid and various neuroprotective carnosic acid derivatives.

FIG. 3 shows the structure of carnosic acid and various neuroprotective carnosic acid derivatives, showing the following changes from carnosic acid (compound 1), with reference to Formula IV or V as appropriate: compound 2, $X_{24}$ is carboxy; compound 3, $X_{24}$ is COOCH$_3$; compound 4, $X_{24}$ is CH$_2$OH; compound 5, (ortho, Formula VI) $X_{24}$ is COOCH$_3$, (para, Formula IV) $X_{21}$ is CH$_2$OH; compound 6, $X_{22}$ is oxo (=O); compound 7, $X_{22}$ is OH and $X_{23}$ is oxo (=O); and compound 8, $X_{21}$ is —CH$_2$OAc.

As used herein, the terms below have the meanings indicated.

The term "acyl," as used herein (which may be abbreviated Ac), alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20, preferably 2 to 6, carbon atoms. Alkenylene refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like.

The term "alkylene," as used herein, alone or in combination, refers to a saturated aliphatic group derived from a straight or branched chain saturated hydrocarbon attached at two or more positions, such as methylene (—CH$_2$—).

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R-S-) radical wherein the term alkyl is as defined above and wherein the sulfur may be singly or doubly oxidized. Examples of suitable alkyl thioether radicals include methylthio, ethylthio, n-propylthio, iso-propylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydronapthalene, octahydronapthalene as well as the multicyclic (multi-centered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer to the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X₃CO— group where X is a halogen.

The term "trisubstituted silyl," as used herein, alone or in combination, refers to a silicone group substituted at its three free valences with groups as listed herein under the definition of substituted amino. Examples include trimethylsilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Thus, for example, contemplated herein is a composition comprising the S enantiomer substantially free of the R enantiomer, or a composition comprising the R enantiomer substantially free of the S enantiomer. By "substantially free" it is meant that the composition comprises less than 10%, or less than 8%, or less than 5%, or less than 3%, or less than 1% of the minor enantiomer. If the particular compound comprises more than one chiral center, the scope of the present disclosure also includes compositions comprising a mixture of the various diastereomers, as well as compositions comprising each diastereomer substantially free of the other diastereomers. The recitation of a compound, without reference to any of its particular diastereomers, includes compositions comprising all four diastereomers, compositions comprising the racemic mixture of R,R and S,S isomers, compositions comprising the racemic mixture of R,S and S,R isomers, compositions comprising the R,R enantiomer substantially free of the other diastereomers, compositions comprising the S,S enantiomer substantially free of the other diastereomers, compositions comprising the R,S enantiomer substantially free of the other diastereomers, and compositions comprising the S,R enantiomer substantially free of the other diastereomers.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

Additional examples of catechol-type neuroprotective electrophiles are shown in Table 1.

TABLE 1

Various catechol-type neuroprotective electrophilic compounds having a core benzene ring with two OH groups in para configuration

| Compound (CA Index Name) | Structure |
|---|---|
| *Synthetic Compounds* | |
| Benzeneacetic acid, 2,5-dihydroxy-α-octylidene-, (Z)-(9CI) | 2,5-dihydroxyphenyl with $-C(CO_2H)=CH-(CH_2)_6-Me$ (Z configuration) |
| Benzenedecanoic acid, 2,5-dihydroxy-ι-oxo-(9CI) [Other names: 11-(2,5-dihydroxyphenyl) undecanoic acid; 2,5-dihydroxybenzene undecanoic acid] | 2,5-dihydroxyphenyl-$C(=O)-(CH_2)_8-CO_2H$ |
| Benzeneundecanoic acid, 2,5-dihydroxy-(9CI) | 2,5-dihydroxyphenyl-$CH_2-(CH_2)_9-CO_2H$ |
| Benzenebutanoic acid, 2,5-dihydroxy-γ-oxo-β-phenyl-(9CI) | 2,5-dihydroxyphenyl-$C(=O)-CH(Ph)-CH_2-CO_2H$ |
| Benzenebutanoic acid, 2,5-dihydroxy-β-(4-methylphenyl)-γ-oxo-(9CI) | 4-methylphenyl-$CH(CH_2-CO_2H)-C(=O)-$2,5-dihydroxyphenyl |
| Benzoic acid, 2-[2-(2,5-dihydroxyphenyl) ethyl]-6-hydroxy-(9CI) | 2-hydroxy-6-($CH_2-CH_2-$2,5-dihydroxyphenyl)benzoic acid |
| Benzoic acid, 5-[2-(2,5-dihydroxyphenyl) ethyl]-2-hydroxy-(9CI) [Other name: NSC 655255] | 2-hydroxy-5-($CH_2-CH_2-$2,5-dihydroxyphenyl)benzoic acid |

TABLE 1-continued

Various catechol-type neuroprotective electrophilic compounds having a core benzene ring with two OH groups in para configuration

| Compound (CA Index Name) | Structure |
| --- | --- |
| Benzoic acid, 4-[2-(2,5-dihydroxyphenyl)-2-oxoethyl]-(9CI) | 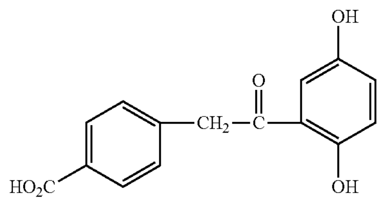 [SMILES: O=C(O)c1ccc(CC(=O)c2cc(O)ccc2O)cc1] |
| Benzoic acid, 3-[[(2,5-dihydroxyphenyl)methyl]amino]-(9CI) [Other name: AG 814] | 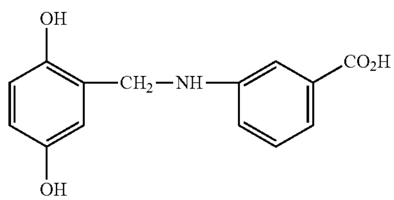 [SMILES: O=C(O)c1cccc(NCc2cc(O)ccc2O)c1] |
| [1,1'-Biphenyl]-4-carboxylic acid, 2',5'-dihydroxy-(9CI) | 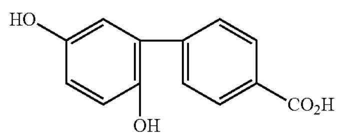 [SMILES: O=C(O)c1ccc(-c2cc(O)ccc2O)cc1] |
| Pentanoic acid, 5-(2,5-dihydroxyphenoxy)-2,2-dimethyl-(9CI) | 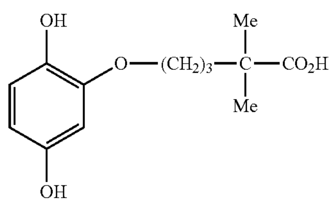 |
| Octanoic acid, 8-[(2,5-dihydroxybenzoyl)amino]-(9CI) | 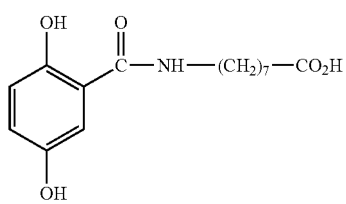 |
| Benzenebutanoic acid, 2,5-dihydroxy-γ-phenyl-(9CI) | 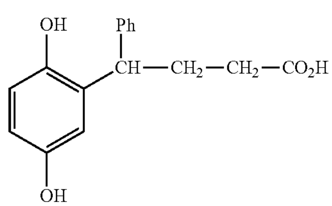 [SMILES: O=C(O)CCC(c1ccccc1)c1cc(O)ccc1O] |
| Naturally Occurring Compounds | |
| 5,9-Undecadienoic acid, 2-[2-(2,5-dihydroxyphenyl)ethylidene]-11-hydroxy-6,10-dimethyl-, (2Z,5E,9E)-(9CI) [Other name: Ganomycin A] | 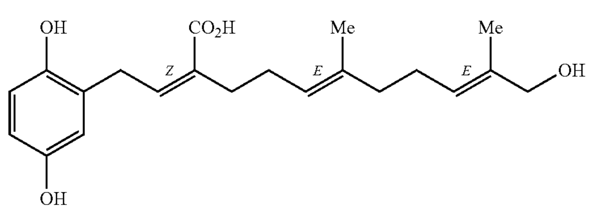 [SMILES: C/C(=C\CC/C(C)=C/CC/C(=C/Cc1cc(O)ccc1O)C(=O)O)CO] |

TABLE 1-continued

Various catechol-type neuroprotective electrophilic compounds having a core benzene ring with two OH groups in para configuration

| Compound (CA Index Name) | Structure |
|---|---|
| 5,9-Undecadienoic acid, 2-[2-(2,5-dihydroxyphenyl)ethylidene]-6,10-dimethyl-, (2Z,5E)-(9CI) [Other name: Ganomycin B] | 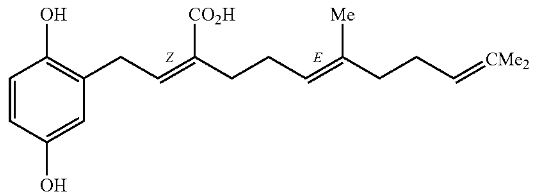 |
| Benzenebutanoic acid, α-[(3E)-4,8-dimethyl-3,7-nonadienyl]-2,5-dihydroxy-γ-oxo-, (+)-(9CI) [Other name: Fornicin C] | 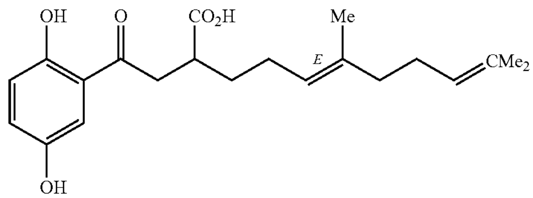 |
| 2,6-Octadienoic acid, 8-(2,5-dihydroxyphenyl)-2,6-dimethyl-8-oxo-, (2E,6E)-(9CI) [Other Name: Orirubenone D] | 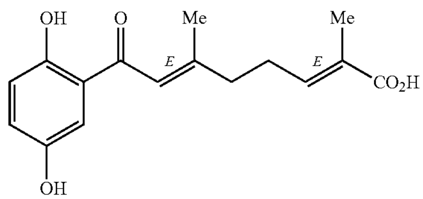 [SMILES: C/C(=C\C(=O)c1cc(O)ccc1O)CC/C=C(\C)C(=O)O] |

Also included in the neuroprotective electrophilic compounds of the invention are ester and ether derivatives of, for example, hydroxyl and carboxy groups in the neuroprotective electrophilic compounds described above, which may increase drug delivery and chemical stability, for example.

Examples of proelectrophiles (also referred to herein as prodrugs of such neuroprotective electrophiles) according to the invention include but are not limited to: carnosic acid and its derivatives (see FIGS. 1 and 3), including, for example, para carnosic acid, carnosol, etc. Derivatives of carnosic acid are well known in the art; see, for example, U.S. Pat. No. 6,479,549 and U.S. Patent Application No. 20040014808.

Other naturally occurring and synthetic terpenoid and flavonoid compounds are also neuroprotective.

Without intending to exclude compounds having other features, such proelectrophiles are preferably lipophilic to enable them to pass through the blood-brain barrier and are hydrophilic in order to be water soluble.

Included among such proelectrophiles are compounds that can be "pathologically activated," that is, activated by the very oxidative stress that they are meant to treat. Thus, in a target tissue under oxidative stress (such as, for example, in the brain), they are converted to a neuroprotective electrophilic compound. The use of such pathologically activated proelectrophiles reduces side effects since they are activated only, or primarily, in the injured tissue. Also included among such proelectrophiles are, for example, para analogues of neuroprotective electrophilic compounds according to the present invention. Such para analogues optionally may be pathologically activated).

As used herein, "neuroprotective substance" is any substance that protects neurons from stress, including, but not limited to, neuronal stress caused by hypoxia, ischemia, abnormal misfolded proteins, excitotoxins, free radicals, endoplasmic reticulum stressors, mitochondrial stressors (including but not limited to inhibitors of the electron transport chain), and Golgi apparatus antagonists. Similarly, as used herein, the term "neuroprotective" refers to any detectable protection of neurons from stress. The neuroprotective compositions and methods of the present invention prevent or delaying cellular injury, damage or death of a cell, as is demonstrated in the Examples. Neuroprotection may be determined directly by, for example, measuring the delay or prevention of neuronal death, such as, for example, by a reduction in the number of apoptotic neurons in cerebrocortical cultures following a stress. Neuroprotection may also be determined directly by, for example, measuring the severity or extent of damage to, or functional loss by, a tissue or organ of the nervous system following such a stress, such as, for example, by measuring a decrease in the size of brain infarcts after MCAO/reperfusion injury. Neuroprotection may be determined indirectly by detecting the activation of one or more biological mechanisms for protecting neurons, including, but not limited to, detecting activation of the Keap1/Nrf2 pathway and/or induction of one or more phase 2 enzymes, including but not limited to hemeoxygenase-1 (HO-1). Methods of detecting and measuring neuronal protection are provided in the Examples below, and other such methods are known in the art.

As used herein, "NEPP" refers to any neurite outgrowth-promoting prostaglandin ($\Delta^7$-prostaglandin $A_1$ analogues) and any derivatives and pharmaceutically acceptable salts thereof.

As used herein, "agent" refers to any substance that has a desired biological activity. For example, a "neuroprotective agent" has detectable biological activity in protecting neurons from an oxidative stress. In addition, neuroprotective agents have detectable biological activity, for example, in treating conditions caused by oxidative stress and symptoms thereof, in a host, including, but not limited to, cerebral ischemia/reperfusion injury (stroke) and various neurodegenerative disorders.

As used herein, a "neurological agent" is a substance, such as a chemical compound, that has an effect on the nervous system, e.g., compounds capable of treating, inhibiting or preventing disorders affecting the nervous system or compounds capable of eliciting a neurological and/or an ophthalmological disorder or symptoms thereof.

As used herein, "effective amount" refers to an amount of a composition that causes a detectable difference in an observable biological effect, including, but not limited to, a statistically significant difference in such an effect. The detectable difference may result from a single substance in the composition, from a combination of substances in the composition, or from the combined effects of administration of more than one composition. For example, an "effective amount" of a neuroprotective composition according to the invention, refers to an amount of the composition that, in a suitable in vitro or in vivo assay; detectably measures or otherwise indicates a delay, prevention, or reduction in neuronal death or a reduction in the severity or extent of damage to, or functional loss by, a tissue or organ of the nervous system following a stress. Also, an "effective amount" of a neuroprotective composition according to the invention refers to an amount of the composition that, in a suitable assay, detectably activates one or more biological mechanisms for protecting neurons, including, but not limited to, detecting activation of the Keap1/Nrf2 pathway and/or induction of one or more phase 2 enzymes, including but not limited to hemeoxygenase-1 (HO-1).

A combination of a neuroprotective substance of the present invention and another active ingredient in a given composition or treatment may be a synergistic combination. The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "synergy," as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

Neuroprotective substances according to the present invention can optionally be co-administered with another neuroprotectant drug or other active ingredient, including, but not limited to, one or more of the following: an anti-glaucoma agent, beta adrenergic blocking agent, carbonic anhydrase inhibitor, miotic agent, sympathomimetic agent, acetylcholine blocking agent, antihistamine, anti-viral agent, quinolone, anti-inflammatory agent, steroidal or non-steroidal anti-inflammatory agent, antidepressant (e.g., serotonin reuptake inhibitor, SSRIs, etc.), psychotherapeutic agent, anti-anxiety agent, analgesic, antiseizure agent, anti-convulsant, gabapentine, anti-hypertensive agent, benzoporphyrin photosensitiser, immunosuppressive antimetabolite, anticonvulsant, barbiturate, benzodiazepine, GABA inhibitor, hydantoin, anti-psychotic, neurolaptic, antidysknetic, andrenergic agent, tricyclic antidepressant, anti-hypoglycemic, glucose solution, polypeptide hormone, antibiotic, thrombolytic agent, blood thinner, antiarrhythmic agent, corticosteroid, seizure disorder agent, anticholinesterase, dopamine blocker, antiparkinsonian agent, muscle relaxant, anxiolytic muscle relaxant, CAN stimulant, antiemetic, beta adrenergic blocking agents, ergot derivative, isomeptene, antiserotonin agent, analgesic, selective serotonin reuptake inhibitors (SSRIs), monosamine oxidase inhibitor, AIDS adjunct agents, anti-infective agent, systemic AIDS adjunct anti-infective, AIDS chemotherapeutic agent, nucleoside reverse transcriptase, and a protease inhibitor.

As used herein, to "treat" includes (i) preventing a pathologic condition from occurring (e.g. prophylaxis); (ii) inhibiting the pathologic condition or arresting its development; and (iii) relieving the pathologic condition; and/or preventing or reducing the severity one or more symptoms associated with such a pathologic condition.

As used herein, the term "patient" refers to organisms to be treated by the compositions and methods of the present invention. Such organisms include, but are not limited to, mammals, including, but not limited to, humans, monkeys, dogs, cats, horses, rats, mice, etc. Such organisms also include other organisms, and cells, tissues and organs of such organisms that are useful in screening for neuroprotective substances according to the present invention. In the context of the invention, the term "subject" generally refers to an individual who will receive or who has received treatment (e.g., administration of a composition comprising a neuroprotective substance according to the present invention).

As used herein, "pharmaceutically acceptable salts" refer to derivatives of a neuroprotective substance according to the present invention wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of a neuroprotective substance useful in the compositions and methods of the present invention can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., p. 1418 (1985), which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The neuroprotective substance according to the present invention can be administered as the parent compound, a pro-drug of the parent compound, or a pharmaceutically acceptable salt, solvate, or active metabolite of the parent compound.

"Pro-drugs" are intended to include any covalently bonded substances which release the active parent drug or other formulas or compounds of the present invention in vivo when such pro-drug is administered to a mammalian subject. Pro-drugs of a compound of the present invention are prepared by modifying functional groups present in the compound in such a way that the modifications are cleaved, either in routine manipulation in vivo, to the parent compound. Examples of pro-drugs include, but are not limited to, pro-electrophilic terpenoid or flavonoid compounds (diterpene or triterpene; for example, carnosic acid) that are metabolized within a patient to form electrophilic compounds that are neuroprotective. As one example, such a pro-electrophilic compound could be activated (metabolized to an electrophilic metabolite) by oxidation in cells and tissues of the nervous system that are under oxidative stress (such as is observed in Parkinson's disease). Thus, the pro-drug would be activated to form neuroprotective electrophilic metabolites via pathological activity, providing neuroprotection at a target site where it is needed.

"Metabolite" refers to any substance resulting from biochemical processes by which living cells interact with the active parent drug or other formulas or compounds of the present invention in vivo, when such active parent drug or other formulas or compounds of the present are administered to a mammalian subject. Metabolites include products or intermediates from any metabolic pathway.

As used herein, "metabolic pathway" refers to a sequence of enzyme-mediated reactions that transform one compound to another and provide intermediates and energy for cellular functions. The metabolic pathway can be linear or cyclic.

As used herein, "neurological disorder" refers to any disorder of the nervous system and/or visual system. "Neurological disorders" include disorders that involve the central nervous system (brain, brainstem and cerebellum), the peripheral nervous system (including cranial nerves), and the autonomic nervous system (parts of which are located in both central and peripheral nervous system). Major groups of neurological disorders include, but are not limited to, headache, stupor and coma, dementia, seizure, sleep disorders, trauma, infections, neoplasms, neuroophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological disorder. The following is a list of several neurological disorders, symptoms, signs and syndromes that can be treated using compositions and methods according to the present invention: acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy-Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease—neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

As used herein, "ophthalmologic disease" or "ophthalmologic disorder" refers to disease or disorder involving the anatomy and/or function of the visual system, including but not limited to, glaucoma, retinal artery occlusion, ischemic optic neuropathy and macular degeneration (wet or dry).

The neurological disorder can be an affective disorder (e.g., depression or anxiety). As used herein, "affective disorder" or "mood disorder" refers to a variety of conditions characterized by a disturbance in mood as the main feature. If mild and occasional, the feelings may be normal. If more severe, they may be a sign of a major depressive disorder or dysthymic reaction or be symptomatic of bipolar disorder. Other mood disorders may be caused by a general medical condition. See, e.g., Mosby's Medical, Nursing & Allied Health Dictionary, 5$^{th}$ edition (1998).

As used herein, "depression" refers to an abnormal mood disturbance characterized by feelings of sadness, despair, and discouragement. Depression refers to an abnormal emotional state characterized by exaggerated feelings of sadness, melancholy, dejection, worthlessness, emptiness, and hopelessness, that are inappropriate and out of proportion to reality. See, Mosby's Medical, Nursing & Allied Health Dictionary, 5$^{th}$ edition (1998). Depression includes, but is not limited to: a major depressive disorder (single episode, recurrent, mild, severe without psychotic features, severe with psychotic features, chronic, with catatonic features, with melancholic features, with atypical features, with postpartum onset, in partial remission, in full remission), dysthymic disorder, adjustment disorder with depressed mood, adjustment disorder with mixed anxiety and depressed mood, premenstrual dysphoric disorder, minor depressive disorder, recurrent brief depressive disorder, post-psychotic depressive disorder of schizophrenia, a major depressive disorder associated with Parkinson's disease, and a major depressive disorder associated with dementia.

The neurological disorder can be pain-associated depression (PAD). As used herein, "pain-associated depression" or "PAD" is intended to refer to a depressive disorder characterized by the co-morbidity of pain and atypical depression. Specifically, the pain can be chronic pain, neuropathic pain, or a combination thereof. Specifically, the PAD can include atypical depression and chronic pain wherein the chronic pain precedes the atypical depression, or vice versa.

"Chronic pain" refers to pain that continues or recurs over a prolonged period of time (i.e., greater than three months), caused by various diseases or abnormal conditions, such a rheumatoid arthritis, for example. Chronic pain may be less intense than acute pain. A person with chronic pain does not usually display increased pulse and rapid perspiration because the automatic reactions to pain cannot be sustained for long periods of time. Others with chronic pain may withdraw from the environment and concentrate solely on their affliction, totally ignoring their family and friends and external stimuli. See, e.g., Mosby's Medical, Nursing & Allied Health Dictionary, 5$^{th}$ edition (1998).

Chronic pain includes but is not limited to: lower back pain, atypical chest pain, headache, pelvic pain, myofascial face pain, abdominal pain, and neck pain or chronic pain caused by disease or a condition such as, for example, arthritis, temporal mandibular joint dysfunction syndrome, traumatic spinal cord injury, multiple sclerosis, irritable bowel syndrome, chronic fatigue syndrome, premenstrual syndrome, multiple chemical sensitivity, closed head injury, fibromyalgia, rheumatoid arthritis, diabetes, cancer, HIV, interstitial cystitis, migraine headache, tension headache, post-herpetic neuralgia, peripheral nerve injury, causalgia, post-stroke syndrome, phantom limb syndrome e, and chronic pelvic pain.

"Atypical depression" refers to a depressed affect, with the ability to feel better temporarily in response to positive life effect (mood reactivity), plus two or more neurovegetative symptoms, including, but not limited to: hypersomnia, increased appetite or weight gain, leaden paralysis, and a long-standing pattern of extreme sensitivity to perceived interpersonal rejection; wherein the neurovegetative symptoms are present for more than about two weeks. Such neurovegetative symptoms can be reversed compared to those found in other depressive disorders (e.g., melancholic depression).

"Acute neurological disorder" refers to a neurological disorder having a rapid onset followed by a short but severe course, including, but not limited to, febrile seizures, Guillain-Barré syndrome, stroke, and intracerebral hemorrhaging.

"Chronic neurological disorder" refers to a neurological disorder lasting for a long period of time (e.g., more than about two weeks; specifically, the chronic neurological disorder can continue or recur for more than about four weeks, more than about eight weeks, or more than about twelve weeks) or is marked by frequent recurrence, including, but not limited to, narcolepsy, chronic inflammatory demyelinating polyneuropathy, cerebral palsy, epilepsy, multiple sclerosis, dyslexia, Alzheimer's disease, and Parkinson's disease.

"Trauma" refers to any injury or shock to the body, as from violence or an accident, or to any emotional wound or shock, such as a wound or shock that causes substantial, lasting damage to the psychological development of a person.

"Ischemic condition" is any condition that results in a decrease in the blood supply to a bodily organ, tissue or part caused by constriction or obstruction of the blood vessels, often resulting in a reduction of oxygen to the organ, tissue or part.

"Hypoxic conditions" are conditions in which the amount or concentration of oxygen in the air, blood or tissue is low (subnormal).

"Painful neuropathy" or "neuropathy" is chronic pain that results from damage to or pathological changes of the peripheral or central nervous system. Peripheral neuropathic pain is also referred to as painful neuropathy, nerve pain, sensory peripheral neuropathy, or peripheral neuritis. With neuropathy, the pain is not a symptom of injury but rather is itself the disease process. Neuropathy is not associated with the healing process. Rather than communicating that there is an injury somewhere, the nerves themselves malfunction and become the cause of pain.

"Neuropathic pain" refers to pain associated with inflammation or degeneration of the peripheral nerves, cranial nerves, spinal nerves, or a combination thereof. The pain is typically sharp, stinging, or stabbing. The underlying disorder can result in the destruction of peripheral nerve tissue and can be accompanied by changes in skin color, temperature and edema. See, e.g., Mosby's Medical, Nursing & Allied Health Dictionary, 5$^{th}$ edition (1998); and Stedman's Medical Dictionary, 25$^{th}$ edition (1990).

"Diabetic neuropathy" refers to a peripheral nerve disorder/nerve damage caused by diabetes, including peripheral, autonomic, and cranial nerve disorders/damage associated with diabetes. Diabetic neuropathy is a common complication of diabetes mellitus in which nerves are damaged as a result of hyperglycemia (high blood sugar levels).

"Drug dependence" refers to habituation to, abuse of, and/or addiction to a chemical substance. Largely because of psychological craving, the life of the drug-dependent person revolves around the need for the specific effect of one or more chemical agents on mood or state of consciousness. The term thus includes not only the addiction (which emphasizes the physiological dependence) but also drug abuse (in which the pathological craving for drugs seem unrelated to physical dependence). Examples include, but are not limited to, dependence on alcohol, opiates, synthetic analgesics with morphine-like effects, barbiturates, hypnotics, sedatives, some antianxiety agents, cocaine, psychostimulants, marijuana, nicotine and psychotomimetic drugs.

"Drug withdrawal" refers to the termination of drug taking. Drug withdrawal also refers to the clinical syndrome of psychological and, sometimes, physical factors that result from the sustained use of a particular drug when the drug is abruptly withdrawn. Symptoms are variable but may include anxiety, nervousness, irritability, sweating, nausea, vomiting, rapid heart rate, rapid breathing, and seizures.

"Drug addiction" or dependence is defined as having one or more of the following signs: a tolerance for the drug (needing increased amounts to achieve the same effect), withdrawal symptoms, taking the drug in larger amounts than was intended or over a longer period of time than was intended, having a persistent desire to decrease or the inability to decrease the amount of the drug consumed, spending a great deal of time attempting to acquire the drug, or continuing to use the drug even though the person knows there are recurring physical or psychological problems caused by the drug.

"Depression" refers to a mental state of depressed mood characterized by feelings of sadness, despair and discouragement. Depression ranges from normal feelings of the blues through dysthymia to major depression.

"Anxiety disorders" refers to an excessive or inappropriate aroused state characterized by feelings of apprehension, uncertainty, or fear. Anxiety disorders have been classified according to the severity and duration of their symptoms and specific behavioral characteristics. Categories include: generalized anxiety disorder, which is long-lasting and low-grade; panic disorder, which has more dramatic symptoms; phobias; obsessive-compulsive disorder; post-traumatic stress disorder; and separation anxiety disorder.

"Tardive dyskinesia" (e.g., Tourette's syndrome) refers to a serious, irreversible neurological disorder that can appear at any age. Tardive dyskinesia can be a side effect of long-term use of antipsychotic/neuroleptic drugs. Symptoms can be hardly noticeable or profound. Symptoms involve uncontrollable movement of various body parts, including the body, trunk, legs, arms, fingers, mouth, lips, or tongue.

"Movement disorder" refers to a group of neurological disorders that involve the motor and movement systems, including, but not limited to, ataxia, Parkinson's disease, blepharospasm, Angelman syndrome, ataxia telangiectasia, dysphonia, dystonic disorders, gait disorders, torticollis, writer's cramp, progressive supranuclear palsy, Huntington's chorea, Wilson's disease, myoclonus, spasticitiy, tardive dyskinesia, tics, Tourette syndrome, and tremors.

"Cerebral infections that disrupt the blood-brain barrier" refers to infections of the brain or cerebrum that result in an alteration in the effectiveness of the blood-brain barrier, either increasing or decreasing its ability to prevent substances and/or organisms from passing out of the bloodstream and into the central nervous system.

"Blood-brain barrier" refers to a semi-permeable layer of endothelial cells within capillaries of the central nervous system that prevents large molecules, immune cells, many potentially damaging substances, and foreign organisms (e.g., viruses) from passing out of the bloodstream and into the central nervous system (e.g., brain and spinal cord). A dysfunction in the blood-brain barrier may underlie in part the disease process in multiple sclerosis.

"Meningitis" refers to inflammation of the meninges of the brain and spinal cord, most often caused by a bacterial or viral infection and characterized by fever, vomiting, intense headache, and stiff neck.

"Meningoencephalitis" refers to inflammation of one or both of the brain and meninges.

"Stroke," also called cerebral accident or cerebrovascular accident, refers to a sudden loss of brain function caused by a blockage or rupture of a blood vessel to the brain (resulting in a lack of oxygen to the brain), characterized by loss of muscular control, diminution or loss of sensation or consciousness, dizziness, slurred speech, or other symptoms that vary with the extent and severity of the damage to the brain.

"Hypoglycemia" refers to an abnormally low level of glucose in the blood.

"Cerebral ischemia" (stroke) refers to a deficiency in blood supply to the brain, often resulting in a lack of oxygen to the brain.

"Cardiac arrest" refers to a sudden cessation of heartbeat and cardiac function, resulting in a temporary or permanent loss of effective circulation.

"Spinal cord trauma," also called spinal cord injury or compression, refers to damage to the spinal cord that results from direct injury to the spinal cord itself or indirectly by damage to the bones and soft tissues and vessels surrounding the spinal cord.

"Head trauma" refers to a head injury of the scalp, skull, or brain. These injuries can range from a minor bump on the skull to a devastating brain injury. Head trauma can be classified as either closed or penetrating. In a closed head injury, the head sustains a blunt force by striking against an object. A concussion is a closed head injury that involves the brain. In a penetrating head injury, an object (usually moving at high speed, such as a windshield or other part of a motor vehicle) breaks through the skull and enters the brain.

"Perinatal hybpxia" refers to a lack of oxygen during the perinatal period (i.e., the period of time occurring shortly before and after birth, variously defined as beginning with completion of the twentieth to twenty-eighth week of gestation and ending 7 to 28 days after birth.

"Hypoglycemic neuronal damage" refers to neuronal damage, for example, nerve damage, resulting from a hypoglycemic condition (i.e., abnormally low blood glucose levels).

"Neurodegenerative disorder" refers to a type of neurological disease marked by the loss of nerve cells, including, but not limited to, Alzheimer's disease, Parkinson's disease, amyotrophic lateral sclerosis, tauopathies (including frontotemporal dementia), and Huntington's disease.

"Epilepsy" refers to any of various neurological disorders characterized by sudden recurring attacks of motor, sensory, or psychic malfunction with or without loss of consciousness or convulsive seizures.

"Alzheimer's disease" refers to a disease marked by the loss of cognitive ability, generally over a period of 10 to 15 years, and associated with the development of abnormal tissues and protein deposits (plaques or tangles) in the cerebral cortex.

"Huntington's disease" refers to a hereditary disease that develops in adulthood and ends in dementia. It results from genetically programmed neuronal degeneration in certain areas of the brain that causes uncontrolled movements, loss of intellectual faculties, and emotional disturbance.

"Parkinsonism" refers to a disorder similar to Parkinson's disease, but which is caused by the effects of a medication, a different neurodegenerative disorder, or another illness. The term "parkinsonism" also refers to any condition that causes any combination of the types of movement abnormalities seen in Parkinson's disease by damaging or destroying dopamine neurons in a certain area of the brain.

"Amyotrophic lateral sclerosis" (ALS), also called Lou Gehrig's disease, refers to a progressive, fatal neurological disease. ALS belongs to a class of disorders known as motor neuron disease. ALS occurs when specific nerve cells in the brain and spinal cord that control voluntary movement gradually degenerate (usually the "upper" (i.e., in the cerebrocortex) and "lower" (in the spinal cord) motor neurons. The loss of these motor neurons causes the muscles under their control to weaken and waste away, leading to paralysis. ALS manifests itself in different ways, depending on which muscles weaken first. Symptoms may include tripping and falling, loss of motor control in hands and arms, difficulty speaking, swallowing and/or breathing, persistent fatigue, and twitching and cramping, sometimes quite severely. Upper motor neuron variants (e.g., primary lateral sclerosis) are also included.

"Glaucoma" refers to any of a group of eye diseases characterized by abnormally high intraocular fluid pressure, damaged optic disk, hardening of the eyeball, and partial to complete loss of vision. The retinal ganglion cells are lost in glaucoma. Some variants of glaucoma (low tension glaucoma) have normal intraocular pressure.

"Retinal ischemia" refers to a decrease in the blood supply to the retina.

"Ischemic optic neuropathy" refers to a condition that usually presents with a sudden onset of unilaterally reduced vision. The condition is the result of decreased blood flow to the optic nerve (ischemia). There are two basic types: arteritic and non-arteritic ischemic optic neuropathy. Non-arteritic ischemic optic neuropathy is generally the result of cardiovascular disease. Patients at greatest risk have a history of high blood pressure, elevated cholesterol, smoking, diabetes, or combinations of these. Arteritic ischemic optic neuropathy is caused by the inflammation of vessels supplying blood to the optic nerves, known as temporal arteritis. This condition usually presents with sudden and severe vision loss in one eye, pain in the jaw with chewing, tenderness in the temple area, loss of appetite, and a generalized felling of fatigue or illness.

"Macular degeneration" refers to the physical disturbance of the center of the retina called the macula, leading to a loss of central vision, although color vision and peripheral vision may remain clear. Vision loss usually occurs gradually and typically affects both eyes at different rates.

A "demyelinating disorder" is a condition resulting from damage to the myelin sheath, which surrounds nerves and is responsible for efficient transmission of nerve impulses to the brain. A demyelinating disorder may result in muscle weakness, poor coordination and possible paralysis. Examples of demyelinating disorders include, but are not limited to: multiple sclerosis, optic neuritis, transverse neuritis and Guillain-Barré syndrome. When treating a demyelinating disorder, a composition according to the present invention may include an N-methyl-D-aspartate-type glutamate receptor (NMDAR) antagonist (e.g., memantine) or beta interferon isoforms, copaxone or Antegren (natalizumab). Since neuronal damage may occur in demyelanting conditions such as multiple sclerosis, useful drug compositions may also protect the neuron instead of or in addition to the myelin.

"Multiple sclerosis" refers to a chronic disease of the central nervous system, which predominantly affects young adults and is characterized by areas of demyelination and T-cell predominant perivascular inflammation in the white matter of the brain. Some axons may be spared from these pathological processes. The disease begins most commonly with acute or subacute onset of neurologic abnormalities. Initial and subsequent symptoms may dramatically vary in their expression and severity over the course of the disease, which usually lasts for many years. Early symptoms may include numbness and/or paresthesia, mono- or paraparesis, double vision, optic neuritis, ataxia and bladder control problems. Subsequent symptoms also include more prominent upper motor neuron signs, i.e., increased spasticity, increasing para- or quadriparesis. Vertigo, incoordination and other cerebellar problems, depression, emotional lability, abnormalities in gait, dysarthria, fatigue and pain are also commonly seen.

"Sequelae of hyperhomocystinemia" refers to a condition following as a consequence hyperhomocystinemia, i.e., elevated levels of homocysteine.

"Convulsion" refers to a violent involuntary contraction or series of contractions of the muscles.

"Pain" refers to an unpleasant sensation associated with actual or potential tissue damage that is mediated by specific nerve fibers to the brain where its conscious appreciation may be modified by various factors. See, e.g., Mosby's Medical, Nursing & Allied Health Dictionary, $5^{th}$ edition (1998); and Stedman's Medical Dictionary, $25^{th}$ edition (1990).

"Anxiety" refers to a state of apprehension, uncertainty, and/or fear resulting from the anticipation of a realistic or fantasized threatening event or situation, often impairing physical and psychological functioning.

"Schizophrenia" refers to any of a group of psychotic disorders usually characterized by withdrawal from reality, illogical patterns of thinking, delusions, and hallucinations, and accompanied in varying degrees by other emotional, behavioral, or intellectual disturbances. Schizophrenia is associated with dopamine imbalances in the brain and defects of the frontal lobe.

"Muscle spasm" refers to an often painful involuntary muscular contraction.

"Migraine headache" refers to a severe, debilitating headache often associated with photophobia and blurred vision.

"Urinary incontinence" refers to the inability to control the flow of urine and involuntary urination.

"Nicotine withdrawal" refers to the withdrawal from nicotine, an addictive compound found in tobacco, which is characterized by symptoms that include headache, anxiety, nausea and a craving for more tobacco. Nicotine creates a chemical dependency, so that the body develops a need for a certain level of nicotine at all times. Unless that level is maintained, the body will begin to go through withdrawal.

"Opiate tolerance" refers to a homeostatic response that reduces the sensitivity of the system to compensate for continued exposure to high levels of an opiate, e.g., heroine or morphine. When the drug is stopped, the system is no longer as sensitive to the soothing effects of the enkephalin neurons and the pain of withdrawal is produced.

"Opiate withdrawal" refers to an acute state caused by cessation or dramatic reduction of use of opiate drugs that has been heavy and prolonged (several weeks or longer). Opiates include heroin, morphine, codeine, Oxycontin, Dilaudid, methadone and others. Opiate withdrawal often includes sweating, shaking, headache, drug craving, nausea, vomiting, abdominal cramping, diarrhea, inability to sleep, confusion, agitation, depression, anxiety, and other behavioral changes.

"Emesis" refers to the act of vomiting.

"Brain edema" refers to an excessive accumulation of fluid in, on, around and/or in relation to the brain.

"AIDS- (or HIV-)induced (or associated) dementia" refers to dementia (a deterioration of intellectual faculties, such as memory, concentration, and judgment, resulting from an organic disease or disorder of the brain) induced by human immunodeficiency virus (HIV), which causes acquired immunodeficiency syndrome (AIDS).

"HIV-related neuropathy" refers to a neuropathy in a mammal infected with HIV where the neuropathy is caused by infections such as with CMV or other viruses of the herpes family. Neuropathy is the name given to a group of disorders whose symptoms may range from a tingling sensation or numbness in the toes and fingers to pain to paralysis.

"Ocular damage" refers to any damage to the eyes or in relation to the eyes.

"Retinopathy" refers to any pathological disorder of the retina.

"Cognitive disorder" refers to any cognitive dysfunction, for example, disturbance of memory (e.g., amnesia) or learning.

In another embodiment of the invention, neuroprotective compounds of the present invention are also used to treat aging due to free radical-induced damage, for example, to slow the process of normal aging of the nervous system of an organism and its symptoms (Finkel, Nat. Rev. Mol. Cell Biol. 6:971-976, 2005; Finkel et al., Nature 408:239-247, 2000). Accordingly, compositions are provided that comprise an amount of a compound according to the present invention that is effective to slow the process of aging of the nervous symptom or a symptom thereof in an individual.

Neurotoxic and Neuroprotective Electrophiles

Reaction of some electrophiles (referred to herein as "neurotoxic" electrophiles) with reduced cysteine residues, e.g., those of glutathione (GSH), can induce neurotoxicity by decreasing the reductive capacity of the cell (Suzuki. et al., J. Am. Chem. Soc. 119:2376-2385, 1997; Spencer et al., FEBS Lett. 24:246-250, 1994). Thus, earlier studies focused on the neurotoxic effects of endogenous electrophiles such as 15d-$PGJ_2$ (Shibata et al., J. Biol. Chem. 281:1196-1204, 2005), catecholamine metabolites (including dopamine) (Spencer et al., FEBS Lett. 24:246-250, 1994), and anti-tumor agents (including doxorubicin) (Wetzel et al., Eur. J. Neurosci. 18:1050-1060, 2003). In this regard, electrophiles can contribute to neuronal death by several mechanisms: (1) GSH depletion, (2) reactive oxygen species (ROS) production, (3) DNA damage, (4) p53 activation, (5) Fas/Fas ligand induction, and (6) mitochondrial dysfunction (Suzuki. et al., J. Am. Chem. Soc. 119:2376-2385, 1997; Spencer et al., FEBS Lett. 24:246-250, 1994; Shibata et al., J. Biol. Chem. 281:1196-1204, 2005; Wetzel et al., Eur. J. Neurosci. 18:1050-1060, 2003). Alkylation of GSH cysteines by electrophiles (Suzuki. et al., J. Am. Chem. Soc. 119:2376-2385, 1997) depletes the reducing capability of the cell (Suzuki. et al., J. Am. Chem. Soc. 119:2376-2385, 1997; Shibata et al., J. Biol. Chem. 281:1196-1204, 2005; Wetzel et al., Eur. J. Neurosci. 18:1050-1060, 2003), and simultaneously the alkylated complex is extruded through the cell membrane via the multidrug resistance-associated protein-1 (MRP-1) (Sekine et al., Am. J. Physiol. Renal Physiol. 290:F251-F261, 2006). Accumulation of reactive oxygen species (ROS) precipitated by GSH depletion contributes to mitochondrial dysfunction, which activates apoptotic machinery, resulting in cytochrome c release, Bax translocation to the inner mitochondrial membrane, and caspase activation (Shibata et al., J. Biol. Chem. 281:1196-1204, 2005; Wetzel et al., Eur. J. Neurosci. 18:1050-1060, 2003). In addition, alkylation of guanine residues inhibits the transcription and replication of DNA, and activates the p53-dependent apoptotic pathway (Spencer et al., FEBS Lett. 24:246-250, 1994; Shibata et al., J. Biol. Chem. 281:1196-1204, 2005).

On the other hand, in response to electrophiles some cells mount an "electrophile counterattack," a system that detoxifies electrophiles and removes them immediately (Eggler et al., Proc. Natl. Acad. Sci. USA 102:10070-10075, 2005; Dinkova-Kostova et al., Chem. Res. Toxicol. 18:1779-1791, 2005; Talalay, Biofactors 12:5-11, 2000; Hong et al., Chem. Res. Toxicol. 18:1917-1926, 2005; Padmanabhan et al., Mol. Cell 21:689-700, 2006). The electrophilic counterattack usually lies relatively dormant but becomes activated by electrophiles themselves (Dinkova-Kostova et al., Chem. Res. Toxicol. 18:1779-1791, 2005; Talalay, Biofactors 12:5-11, 2000; Hong et al., Chem. Res. Toxicol. 18:1917-1926, 2005; Padmanabhan et al., Mol. Cell 21:689-700, 2006). Since this electrophile counterattack eliminates not only the electrophiles but also ROS, it can thus prevent neurodegeneration and tumor growth (Dinkova-Kostova et al., Chem. Res. Toxicol. 18:1779-1791, 2005; Talalay, Biofactors 12:5-11, 2000; Hong et al., Chem. Res. Toxicol. 18:1917-1926, 2005; Padmanabhan et al., Mol. Cell 21:689-700, 2006). Thus, electrophiles could possibly be used as both anti-tumor (Dinkova-Kostova et al., Chem. Res. Toxicol. 18:1779-1791, 2005; Talalay, Biofactors 12:5-11, 2000; Hong et al., Chem. Res. Toxicol. 18:1917-1926, 2005; Padmanabhan et al., Mol. Cell 21:689-700, 2006) and neuroprotective agents (Satoh et al., Proc. Natl. Acad. Sci. USA 103:768-773, 2006; Shih et al., J. Neurosci. 25:10321-10335, 2005; Kraft et al., J. Neurosci. 24:1101-1112, 2004; Shih et al., J. Neurosci. 23:3394-3406, 2003). Talalay (Biofactors 12:5-11, 2000) was the first to introduce this concept and termed the phenomenon "chemoprevention" in view of its cancer-combating properties. Many chemopreventive agents are electrophilic and increase cellular resistance to oxidative stress (Dinkova-Kostova et al., Chem. Res. Toxicol. 18:1779-1791, 2005; Talalay, Biofactors 12:5-11, 2000; Hong et al., Chem. Res. Toxicol. 18:1917-1926, 2005; Padmanabhan et al., Mol. Cell 21:689-700, 2006). This form of chemoprevention often entails a transcription-based mechanism involving a specific signaling pathway (the Keap1/Nrf2 pathway) and the induction of phase 2 genes, which encode enzymes representing a coordinated response to electrophiles, including the genes encoding the following enzymes: heme oxygenase 1 (HO-1), which generates antioxidants (bilirubin); NADPH-quinone oxidoreductase (NQO1), which reduces quinones to hydroquinones; multidrug resistance-associated protein (MRP-1), which transports GSH-conjugated compounds out of the cell; γ-glutamylcysteine synthetase (γ-GCS), which is involved in synthesis of GSH; and cysteine/glutamate antiporter (xCT), which is involved in uptake of cystine, a precursor of cysteine. Other phase 2 enzymes include: glutathione S-transferase, which conjugates electrophiles to GSH; catalase, which detoxifies hydrogen peroxide; manganese superoxide dismutase, which detoxifies superoxide; and metallothionein-1 and -2, which detoxify heavy metals. Most phase 2 enzymes are involved in drug detoxification and redox regulation and are induced by electrophilic compounds (Dinkova-Kostova et al., Chem. Res. Toxicol. 18:1779-1791, 2005; Talalay, Biofactors 12:5-11, 2000; Hong et al., Chem. Res. Toxicol. 18:1917-1926, 2005; Padmanabhan et al., Mol. Cell 21:689-700, 2006).

In neurons, electrophiles also manifest two disparate actions: a neurotoxic effect, mediated by a decrease in total cellular reductive capacity, but also an electrophile counterattack via the induction of phase 2 genes. If the neurotoxic effects predominate, then a particular electrophile will kill a neuron [e.g., doxorubicin (Wetzel et al., Eur. J. Neurosci. 18:1050-1060, 2003] and menadione [Nguyen et al., Antioxid. Redox Signal. 5:629-634, 2003)]. In contrast, if the electrophile counterattack predominates, which occurs especially in response to weak electrophiles, then the electrophilic response will rescue neurons from free radical-related insults [e.g., as observed with tert-butyl hydroquinone (TBHQ) (Shih et al., J. Neurosci. 25:10321-10335, 2005; Kraft et al., J. Neurosci. 24:1101-1112, 2004; Shih et al., J. Neurosci. 23:3394-3406, 2003) and neurite outgrowth-promoting prostaglandin (NEPP) compounds. Thus, preferential activation of the electrophile counterattack, while minimizing the neurotoxic effects of electrophiles that deplete total cellular redox state, has been touted as a new therapeutic strategy against neurodegeneration (Satoh et al., Proc. Natl. Acad. Sci. USA 103:768-773, 2006; Shih et al., J. Neurosci. 25:10321-10335, 2005; Kraft et al., J. Neurosci. 24:1101-1112, 2004; Shih et al., J. Neurosci. 23:3394-3406, 2003). Murphy et al. (J. Neurochem. 56:990-995, 1991) first demonstrated that exogenous electrophiles can be neuroprotective. For example, TBHQ and dimethyl fumarate protected neurons against oxidative stress. This protective effect was associated with the induction of NADPH-quinone oxidoreductase-1 (NQO1), a phase 2 enzyme (Murphy et al., J. Neurochem. 56:990-995, 1991; Shih et al., J. Biol. Chem. 280:22925-22936, 2005). Electrophilic neuroprotection displays the following parameters: (1) the protection is transcription dependent and thus requires pretreatment; (2) the protective compounds themselves may be electrophiles or may generate electrophiles; (3) the compounds spare essential cellular redox factors such as GSH; and (4) the compounds induce expression of phase 2 enzymes, such as NQO1 and heme oxygenase-1 (HO-1), often via the Keap1/Nrf2 transcription factor pathway (Satoh et al., Proc. Natl. Acad. Sci. USA 103:768-773, 2006; Shih et al., J. Neurosci. 25:10321-10335, 2005; Kraft et al., J. Neurosci. 24:1101-1112, 2004; Shih et al., J. Neurosci. 23:3394-3406, 2003). Interestingly, Murphy, Johnson and colleagues showed that the neuroprotective effect of TBHQ against stroke is mediated via activation of the Keap1/Nrf2 pathway in astrocytes and a resulting paracrine effect on neurons when it is used at proper concentrations (Shih et al., J. Neurosci. 25:10321-10335, 2005; Kraft et al., J. Neurosci. 24:1101-1112, 2004; Shih et al., J. Neurosci. 23:3394-3406, 2003; Shih et al., J. Biol. Chem. 280:22925-22936, 2005). In contrast, doxorubicin and menadione are neurotoxic quinine-based electrophilic compounds; they deplete intracellular GSH and kill neurons by precipitating oxidative stress at virtually any concentration (Wetzel et al., Eur. J. Neurosci. 18:1050-1060, 2003; Nguyen et al., Antioxid. Redox Signal. 5:629-634, 2003). Thus, electrophiles can be divided into two groups: neurotoxic electrophiles and neuroprotective electrophiles. At low concentration the NEPP family of electrophiles, particularly NEPP11, protects neurons against oxidative stress (Example 1; see also Satoh et al., J. Neurochem. 77:50-62, 2001). NEPP compounds that were generated on the basis of the chemical structure of cyclopentenone prostaglandins protect neurons from oxidative stress in an HO-1-dependent manner (Satoh et al., J. Neurochem. 77:50-62, 2001; Satoh et al., J. Neurochem. 75:1092-1102, 2000; Satoh et al., Eur. J. Neurosci. 17:2249-2255, 2003). We reasoned that since NEPPs were electrophilic compounds, the key to an understanding of their neuroprotective action was identification of the protein thiols with which they reacted. Along these lines, it was found that a number of electrophiles exerted neuroprotective effects that were closely linked with the Keap1/Nrf2 transcriptional pathway (Example 1; see also Shih et al., J. Neurosci. 25:10321-10335, 2005; Kraft et al., J. Neurosci. 24:1101-1112, 2004; Shih et al., J. Neurosci. 23:3394-3406, 2003). A second important point, however, is that this class of molecules is preferentially concentrated in neurons and thus works directly on neurons in a targeted fashion.

Concerning the chemical reactions and signal transduction pathways triggered by NEPPs, electrophile binding to cysteine residue(s) can initiate neuroprotection, based on the following lines of evidence: (1) NEPP and related compounds bind to cysteine in a cell-free system (Suzuki. et al., J. Am. Chem. Soc. 119:2376-2385, 1997); (2) N-ethylmaleimide, a sulfhydryl alkylating agent, abolishes the binding of NEPP compounds to the cysteine residues of bovine serum albumin (Example 1); (3) cross-conjugated dienone, the electrophilic moiety of NEPPs, is required for neuroprotection and HO-1 induction (Satoh et al., J. Neurochem. 77:50-62, 2001; Satoh et al., J. Neurochem. 75:1092-1102, 2000); (4) Keap1 mutants (cysteine at position 151 replaced by serine) abolishe HO-1 induction by NEPP11 and its neuroprotective effect (Example 1). Thus, alkylation/redox signaling of Keap1 by NEPP11 might initiate neuroprotective events through induction of phase 2 genes (Example 1; Satoh et al., Eur. J. Neurosci. 17:2249-2255, 2003).

A number of studies have provided evidence that electrophiles can protect neurons via activation of the Keap1/Nrf2 pathway with the consequent induction of HO-1 and other phase 2 enzymes. These enzymes engender neuroprotection via modulation of the intracellular redox state (Example 1; Shih et al., J. Neurosci. 25:10321-10335, 2005; Kraft et al., J. Neurosci. 24:1101-1112, 2004; Shih et al., J. Neurosci. 23:3394-3406, 2003). The antioxidant response element (ARE) is a transcriptional element that is located in the 5' upstream promoter region of genes that encode phase 2 enzymes. Transcription factors binding to AREs thus mediate the induction of phase 2 enzymes (Dinkova-Kostova et al., Chem. Res. Toxicol. 18:1779-1791, 2005; Talalay, Biofactors 12:5-11, 2000; Hong et al., Chem. Res. Toxicol. 18:1917-1926, 2005; Padmanabhan et al., Mol. Cell 21:689-700, 2006). Yamamoto's group were the first to demonstrate that the Keap1/Nrf2 pathway activates AREs (Padmanabhan et al., Mol. Cell 21:689-700, 2006). Keap1 is an adapter protein for ubiquitination of Nrf2 and thus drives the continuous degradation of this transcription factor (Eggler et al., Proc. Natl. Acad. Sci. USA 102:10070-10075, 2005; Dinkova-Kostova et al., Chem. Res. Toxicol. 18:1779-1791, 2005; Talalay, Biofactors 12:5-11, 2000; Hong et al., Chem. Res. Toxicol. 18:1917-1926, 2005; Padmanabhan et al., Mol. Cell 21:689-700, 2006). When electrophiles react with critical cysteine residues on Keap1 to form an adduct, they perturb this system and stabilize Nrf2, causing the liberation of Nrf2 and allowing it to be translocated into the nucleus, where it binds to AREs and stimulates the expression of phase 2 genes (Eggler et al., Proc. Natl. Acad. Sci. USA 102:10070-10075, 2005; Dinkova-Kostova et al., Chem. Res. Toxicol. 18:1779-1791, 2005; Talalay, Biofactors 12:5-11, 2000; Hong et al., Chem. Res. Toxicol. 18:1917-1926, 2005; Padmanabhan et al., Mol. Cell 21:689-700, 2006). In fact, Nrf2 is a primary transcription factor responsible for the electrophile counterattack response in the brain (Satoh et al., Proc. Natl. Acad. Sci. USA 103:768-773, 2006; Shih et al., J. Neurosci. 25:10321-10335, 2005; Kraft et al., J. Neurosci. 24:1101-1112, 2004; Shih et al., J. Neurosci. 23:3394-3406, 2003; Johnson et al., J. Neurochem. 81:1233-1241, 2002, Lee et al., J. Biol. Chem. 278:37948-37956, 2003). Experiments using ARE reporter mice have demonstrated that TBHQ activates AREs in astroglial cells, resulting in activation of the Keap1/Nrf2 pathway and subsequent protection of neurons from oxidative insult; thus, TBHQ protects neurons by activating the Keap1/Nrf2 pathway in astrocytes (Shih et al., J. Neurosci. 25:10321-10335, 2005; Kraft et al., J. Neurosci. 24:1101-1112, 2004; Shih et al., J. Neurosci. 23:3394-3406, 2003; Johnson et al., J. Neurochem. 81:1233-1241, 2002; Lee et al., J. Biol. Chem. 278:37948-37956, 2003). Experiments using cerebral cortical cultures from Nrf2 knockout mice confirmed the importance of Nrf2 protein for induction of phase 2 genes by TBHQ in astrocytes and the consequent neuroprotective effects (Johnson et al., J. Neurochem. 81:1233-1241, 2002; Lee et al., J. Biol. Chem. 278:37948-37956, 2003).

Our research suggests a pathway for electrophile-induced neuroprotection. An electrophile binds to the cytosolic regulator protein Keap1, which in turn liberates the transcription factor Nrf2. Nrf2 then translocates into the nucleus, where it activates ARE sites on the HO-1 promoter. Transcription of HO-1 is thus activated, and the resulting increase in HO-1 protein leads to degradation of heme molecules, producing biliverdin and ultimately bilirubin. The accumulation of bilirubin, a potent antioxidant molecule, mediates at least in part the neuroprotective effect of HO-1. After exposure to the electrophile THBQ, this pathway is triggered in astrocytes, but after exposure to NEPP compounds, the pathway is activated in neurons.

Electrophilic NEPP compounds accumulate in neurons rather than astrocytes to activate the Keap1/Nrf2 pathway and induce phase 2 genes such as HO-1 directly in neurons (Satoh et al., Proc. Natl. Acad. Sci. USA 103:768-773, 2006). The apparent difference in the cell type manifesting activated Keap1/Nrf2 after TBHQ versus NEPP exposure may possibly be attributed to the disparate chemical structures of these compounds, which can differentially affect their cellular uptake (Satoh et al., Proc. Natl. Acad. Sci. USA 103:768-773, 2006). (Catechol-type electrophilic compounds, such as those listed in Table 1, typically enter into both neurons and astrocytes.)

Since plants produce a vast variety of electrophiles, some foods may contain chemopreventive compounds (Talalay, Biofactors 12:5-11, 2000). For example, curcumin, the powdered rhizome of *Curcuma longa* Linn, represents one of many potential electrophiles of plant origin that act as neuroprotective agents (Talalay, Biofactors 12:5-11, 2000). Curcumin activates the Keap1/Nrf2/HO-1 pathway and exerts protective effects against brain ischemia (Balogun et al., Biochem. J. 371:887-895, 2003). Curcumin also protects neurons against chronic neurodegeneration in a murine model of Alzheimer's disease (Lim et al., J. Neurosci. 21:8370-8377, 2001). Additionally, curcumin displays anti-tumor (pro-apoptotic) effects (Talalay, Biofactors 12:5-11, 2000). Based on this background information, Dinkova-Kostova et al. (Proc. Natl. Acad. Sci. USA 98:3404-3409, 2001) screened analogues of curcumin for induction of NQO1 activity and found that bis(4-hydroxybenzylidene)acetone (4-HBA) had the most potent anti-carcinogenic activity (Dinkova-Kostova et al., Proc. Natl. Acad. Sci. USA 98:3404-3409, 2001). Interestingly, our group (Satoh et al., J. Neurochem. 77:50-62, 2001) independently reached a similar conclusion regarding this class of chemical structures, i.e., cross-conjugated dienones, because of the activity of NEPP11 in promoting neuronal survival. Thus, one structural class of neuroprotective electrophiles contains a cross-conjugated dienone.

One phase 2 gene product induced by electrophilic activation of the Keap1/Nrf2 pathway is HO-1. This enzyme oxidatively cleaves heme to biliverdin, forming carbon monoxide (CO) and releasing chelated $Fe^{2+}$ (Maines and Gibbs, Biochem. Biophys. Res. Commun. 338:568-577, 2005). Bilirubin, the product of reduction of biliverdin, serves as a potent free radical scavenger (Stocker, Antioxid. Redox Signal. 6:841-849, 2004). HO-1 plays an obligatory role in resistance to oxidative stress as revealed by reports that fibroblasts from $HO-1^{-/-}$ mice are sensitive to oxidative stress (Poss and Tonegawa, Proc. Natl. Acad. Sci. USA 94:10925-10930, 1997) while cerebellar granule neurons from HO-1 transgenic mice are resistant to oxidative stress (Chen et al., J. Neurochem. 75:304-313, 2000). Among phase 2 enzymes, HO-1 has attracted special attention because of its therapeutic effects, for instance, against inflammation (Lee et al., Nat. Med. 8:240-246, 2002). Baranano and Snyder (Proc. Natl. Acad. Sci. USA 98:10996-1002, 2001), Maines and Gibbs (Biochem. Biophys. Res. Commun. 338:568-577, 2005), and our group (Example 1) have all proposed that HO-1 inducers are neuroprotective. For example, as demonstrated in Example 1, the HO-1 protein plays a central role in the neuroprotective effect of NEPP11, as evident from following facts: (1) HO-1 is dramatically increased by NEPP11 (Example 1; Satoh et al., J. Neurochem. 75:1092-1102, 2000); (2) HO-1 inhibitors abrogate the neuroprotective effect of NEPP11 (Example 1); (3) transfection with HO-1 cDNA is neuroprotective (Satoh et al., J. Neurochem. 75:1092-1102, 2000); and bilirubin, which is downstream from HO-1 enzymatic activity, is also neuroprotective (Satoh et al., J. Neurochem. 75:1092-1102, 2000).

Furthermore, as stated above, NEPP compounds accumulate in neurons, and HO-1 is induced in cortical neurons after intraperitoneal injection of mice with NEPP11. Thus, induction of HO-1 by treatment with NEPP11 or similar agents represents a novel method of targeted neuronal therapy for neurodegenerative disorders (Example 1). HO exists as 2 isozymes: HO-1, an inducible form, and HO-2, a constitutive form (Maines and Gibbs, Biochem. Biophys. Res. Commun. 338:568-577, 2005). HO-2 activity is also essential for protecting neurons against oxidative stress, as evidenced by studies on HO-2 knockout mice (Dore. et al., Proc. Natl. Acad. Sci. USA 96:2445-3450, 1999). We have proposed that HO-1 and HO-2 play central roles in protecting neurons against oxidative stress but via differential regulation: HO-2 is activated first by phosphorylation, and HO-1 is activated subsequently via transcriptional mechanisms (Satoh et al., Eur. J. Neurosci. 17:2249-2255, 2003).

Neuroprotective electrophiles often increase basal levels of GSH (Sun et al., Biochem. Biophys. Res. Commun. 14:371-377, 2005). Since GSH is a major reducing substance protecting against cellular oxidative stress, an increase in its level could in part account for the neuroprotective effects of electrophiles (Sun et al., Biochem. Biophys. Res. Commun. 14:371-377, 2005). The increase in GSH is due to an increase in both cystine (a precursor of cysteine) uptake and GSH synthesis. The ARE regulates expression of both the cystine/glutamate antiporter (xCT) and γ-glutamylcysteine synthetase (γ-GCS), which represent the rate-limiting steps for cystine uptake and GSH synthesis, respectively (Talalay, Biofactors 12:5-11, 2000). Thus, electrophilic induction of xCT and γ-GCS via the ARE may contribute to neuroprotection by increasing GSH.

Additionally, NQO1 is a phase 2 gene product induced by electrophiles. NQO1 catalyzes the two-electron reduction of several quinones to the corresponding hydroquinone (Talalay, Biofactors 12:5-11, 2000; Dinkova-Kostova et al., Proc. Natl. Acad. Sci. USA 98:3404-3409, 2001). Although reduced quinones could potentially function as effective antioxidants, other evidence suggests that it is unlikely that NQO1 activity is involved in the neuroprotective effect of electrophiles for the following reasons: (1) transfection of neuronal cells with the NQO1 gene does not offer protection (Murphy et al., J. Neurochem. 56:990-995, 1991), and (2) NQO1 may paradoxically enhance neuronal cell death by an unknown mechanism (Kapinya et al., J. Neurochem. 84:1028-1039, 2003).

TBHQ and NEPP11 preferentially activate the electrophilic counterattack while minimizing neurotoxic effects due to the binding of TBHQ and NEPP11 to cysteines specific for neuroprotection. One such cysteine residue appears to be Cys 151 of Keap1 (Eggler et al., Proc. Natl. Acad. Sci. USA 102:10070-10075, 2005; Hong et al., Chem. Res. Toxicol. 18:1917-1926, 2005); such cysteine thiols are potential drug targets for the development of novel neuroprotective agents against neurodegenerative diseases.

It is possible that, when systemically administered, electrophiles such as NEPP11 and 4-HBA and thiols may react before the electrophiles reach their intended targets in the brain. Thus, a compound that acts as a pro-drug and converts to an electrophile by oxidation upon reaching the intended target may be desirable. For example, terpenoids that possess catechol rings represent pro-electrophilic compounds that can be converted to quinone-type electrophiles by oxidation (Dinkova-Kostova et al., Proc. Natl. Acad. Sci. USA 102: 4584-4589, 2005). In Parkinson's disease, oxidative stress plays a critical role in disease progression (Jener, Ann. Neurol. 53:S36-S38, 2003) but could be used to activate pro-electrophilic compounds via their oxidation at the target site to provide neuroprotection where it is needed. This approach represents a novel strategy against neurodegenerative disorders that could activate electrophilic drugs via pathological activity.

Carnosic acid (CA) is a polyphenolic antioxidant derived from the plants rosemary (*Rosmarinus officinalis*) and sage (*Salvia officinalis* L.), for example. We have found that carnosic acid (CA) is a terpenoid that can be converted to a neuroprotective quinone by oxidation. It activates the Keap1/Nrf2 pathway similar in a manner similar to NEPPs. CA has certain advantages as well. CA is brain permeable. It is also activated by oxidation and hence may be activated, i.e., converted to its neuroprotective quinone metabolite, at the site of the insult. Furthermore, it will remain for longer periods in the injured tissue. In vitro, approximately 0.1 µM to 10 µM CA is neuroprotective. In vivo, a dosage range of between 1 mg/kg to 100 mg/kg is expected to be optimal, although other dosages may be used as well. The precise dosage that is useful in the practice of the present invention may be determined without undue experimentation. Methods for obtaining carnosic acid from rosemary and sage are taught, for example, in U.S. Pat. Nos. 5,256,700; 5,859,293; and 6,335,373, and the purified compound is available commercially.

Carnosic acid derivatives may also be used in the practice of the present invention. See, for example, U.S. Pat. No. 6,479,549 for some examples of carnosic acid derivatives and their chemical synthesis. Other CA derivatives are known in the art or may be produced by the skilled artisan without undue experimentation. Examples include the following compounds and derivatives thereof in which the benzene ring has two hydroxyl groups in para orientation rather than ortho configuration (by CA Index Name): 1,4a(2H)-Phenanthrenedicarboxylic acid, 1,3,4,9,10,10a-hexahydro-5,6-dihydroxy-1-methyl-7-(1-methylethyl)-, (1R,4aR,10aS)-; 1,4a(2H)-Phenanthrenedicarboxylic acid, 1,3,4,9,10,10a-hexahydro-5,6-dihydroxy-1-methyl-7-(1-methylethyl)-, 1-methyl ester, (1R,4aR,10aS)-; 4a(2H)-Phenanthrenecarboxylic acid, 1,3,4,9,10,10a-hexahydro-5,6-dihydroxy-1-(hydroxymethyl)-1-methyl-7-(1-methylethyl)-, (1R,4aR,10aS)-; 4a(2H)-Phenanthrenecarboxylic acid, 1,3,4,9,10,10a-hexahydro-5,6-dihydroxy-7-(2-hydroxy-1-methylethyl)-1,1-dimethyl-, [4aR-[4aα,7(R*),10aβ]]-(9CI) (also called 16-hydroxycarnosic acid); 5ξ,10ξ-Podocarpa-8,11,13-trien-17-oic acid, 7,11,12-trihydroxy-13-isopropyl (7CI); 4a(2H)-Phenanthrenecarboxylic acid, 1,3,4,9,10,10a-hexahydro-5,6-dihydroxy-1,1-dimethyl-7-(1-methylethyl)-9-oxo-, (4aR-trans)-(9CI); 4a(2H)-Phenanthrenecarboxylic acid, 1,3,4,9,10,10a-hexahydro-5,6,9-trihydroxy-1,1-dimethyl-7-(1-methylethyl)-10-oxo-, [4aR-(4aα,9β,10aβ)]-(9CI); 4a(2H)-Phenanthrenecarboxylic acid, 1,3,4,9,10,10a-hexahydro-5,6,9-trihydroxy-1,1-dimethyl-7-(1-methylethyl)-, (4aR,9S,10aS)- (also called Carnosolic acid); and 4a(2H)-Phenanthrenecarboxylic acid, 7-[2-(acetyloxy)-1-methylethyl]-1,3,4,9,10, 10a-hexahydro-5,6-dihydroxy-1,1-dimethyl-(9CI).

Screening Methods

A number of NEPPs and other electrophilic and pro-electrophilic compounds are known in the literature.

Methods are provided for screening for other substances that are effective for neuroprotection, as described in detail in the Examples. In addition to the methods taught herein, methods for screening for neuroprotective substances are known in the art.

Pharmaceutical Compositions and Methods.

The compositions of the invention can be formulated as pharmaceutical compositions and administered to a mammalian host, such as a human patient, in a variety of forms adapted to the chosen route of administration, i.e., orally or parenterally, by intravenous, intramuscular, topical or subcutaneous routes.

Such compositions may be systemically administered in vivo by a variety of routes. For example, they may be administered orally, in combination with a pharmaceutically acceptable excipients such as an inert diluent or an assimilable edible carrier. They may be enclosed in hard or soft shell gelatin capsules, may be compressed into tablets, or may be incorporated directly with the food of the patient's diet. For oral administration, the active ingredient or ingredients may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active ingredient in such useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compositions may also be administered intravenously or intraperitoneally by infusion or injection. Solutions of a neuroprotective compound according to the present invention, their salts or solvates, and other active ingredients can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating a neuroprotective compound according to the present invention or other active ingredients in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, a neuroprotective compound according to the present invention and other active ingredients may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of a neuroprotective compound according to the present invention or other active ingredients can be determined by comparing their in vitro activity and in vivo activity in animal models. Methods for the extrapolation of effective dosages in mice, and other animals, to humans are known to the art; for example, see U.S. Pat. No. 4,938,949.

Generally, the concentration of a neuroprotective compound according to the present invention or other active ingredients of the invention in a liquid composition will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use alone or with other agents will vary not only with the particular salt selected but also with the route of administration, the nature of the condition being treated and the age and condition of the patient and will be ultimately at the discretion of the attendant physician or clinician.

In general, however, a suitable dose may be in the range of from about 0.5 to about 100 mg/kg, e.g., from about 1 to about 75 mg/kg of body weight per day, or 1.5 to about 50 mg per kilogram body weight of the recipient per day, or about 2 to about 30 mg/kg/day, or about 2.5 to about 15 mg/kg/day.

The compound may be conveniently administered in unit dosage form; for example, containing 5 to 1000 mg, conveniently 10 to 750 mg, most conveniently, 50 to 500 mg of active ingredient per unit dosage form.

The active ingredient may be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Pharmaceutical compositions according to the invention may comprise one or more than one neuroprotective substance according to the invention. Pharmaceutical compositions comprising a neuroprotective compound according to the present invention may also include other active ingredients.

Numerous modifications and variations of the present invention are possible in light of the above teachings. It is therefore to be understood that within the scope of the appended claims, the invention may be practiced otherwise than as specifically described herein.

The present invention will be further described by the following nonlimiting examples.

EXAMPLE 1

A recent study showed that activation of the Keap1/Nrf2/ARE pathway mediates HO-1 induction by electrophiles (Itoh et al., Mol. Cell. Biol. 24:36-45, 2004; Gong et al., Antioxid. Redox Signal. 4:249-257, 2002). Thus we focused on this pathway as a possible mechanism by which neurite outgrowth-promoting prostaglandins (NEPPs) promote HO-1 induction and neuroprotection. We have found that NEPPs protect cortical neurons both in vitro and in vivo against neuronal degeneration by acting as electrophiles to activate the Keap1/Nrf2 pathway.

Materials and Methods

Cell cultures, transfection, and glutathione (GSH) measurement. HT22 cells (Satoh et al., Eur. J. Neurosci. 17:2249-2255, 2003; Satoh et al., J. Neurochem. 77:50-62, 2001; Sagara et al., J. Biol. Chem. 277:36204-36215, 2002) and primary cortical neurons (Bonfoco et al., Proc. Natl. Acad. Sci. USA 92:7162-7166, 1995) were cultured as described.

Transfection was performed with Lipofectamine 2000 (Invitrogen). In the reporter gene assays, firefly luciferase activity in cell lysates was measured with a luminometer (Promega). Total GSH (reduced and oxidized) was determined as described (Lee et al., Biochem. Biophys. Res. Commun. 280: 286-292, 2001).

Immunoprecipitation, western blots, and immunofluorescence. These assays were performed as described (Gu et al., Science 297:1186-1190, 2002) by using the following antibodies: anti-HO-1 (SPA895, 1:1000, Santa Cruz Biotechnology), anti-Keap1 (1:100, Santa Cruz Biotechnology), or anti-actin (1:5,000, Oncogene Research Products, San Diego).

Electrophoretic mobility shift assays (EMSAs). Double-stranded antioxidant-responsive elements (AREs) were labeled by using a biotin 3'-end DNA labeling kit (Pierce). Nuclear lysates were incubated with the labeled probe for 20 min at room temperature, resolved on an 8% native polyacrylamide gel, and transferred to Hybond-N+ (Amersham Pharmacia). Signals were visualized with peroxidase-conjugated streptavidin (Pierce).

Focal cerebral ischemia and reperfusion. The filament model of middle cerebral artery occlusion (MCAO)/reperfusion was used as described (Gu et al., Science 297:1186-1190, 2002; see *Supporting Methods in Supporting Text*).

Statistical analysis. Experiments presented were repeated at least three times with four samples. The data are presented as mean±standard deviation (SD) (for in vitro experiments) or SEM (for in vivo experiments).

Results

Thiols as targets of electrophilic NEPPs. We generated NEPP-related compounds based on the chemical structures of cyclopentenone prostaglandins and found that NEPP6 and -11 protected neurons against oxidative stress (Satoh et al., Eur. J. Neurosci. 17:2249-2255, 2003; Satoh et al., J. Neurochem. 77:50-62, 2001) and that induction of HO-1 played an essential role in these neuroprotective effects (Satoh et al., Eur. J. Neurosci. 17:2249-2255, 2003). NEPP11 afforded more potent neuroprotection than did NEPP6, probably because NEPP11 is more lipophilic, allowing for better CNS permeability (Satoh et al., J. Neurochem. 77:50-62, 2001). The cross-conjugated dienone structure of NEPPs is critical for their biological effects (Satoh et al., J. Neurochem. 77:50-62, 2001) and underlies the electrophilicity of carbon #11 and thus its high chemical reactivity with thiols (Satoh et al., J. Neurochem. 77:50-62, 2001).

Through its single free thiol group (on cysteine residue #34), BSA has been used as an in vitro example for adduct formation by electrophilic compounds. We tested whether the free cysteine of bovine serum albumin (BSA) could form an adduct with NEPP compounds. If carbon #11 on the NEPP compounds binds to this free cysteine of BSA, then pretreatment with N-ethylmaleimide (NEM), in irreversible thiol alkylating agent, would abolish this binding. In an experiment to test this idea, we synthesized NEPP6-biotin (Satoh et al., J. Neurochem. 77:50-62, 2001). Biotin was conjugated to the C1 carbonic acid site on NEPP6 by using a chemical linker. With streptavidin as a probe, we could then detect proteins bound to NEPP6-biotin. In order to study thiols as targets of NEPP binding, BSA (1 µg per lane) was incubated with various concentrations (0-1000 µM) of N-ethylmaleimide (NEM) for 30 minutes at room temperature. Vehicle or NEPP6-biotin (10 µM) in phosphate-buffered saline (PBS) was added and the mixture was incubated at room temperature for 5 h, subjected to sodium dodecyl sulfate polyacrylamide gel electrophoresis (SDS-PAGE), and probed with peroxidase-conjugated streptavidin. The gel was also stained with Coomassie brilliant blue. After exposure to NEPP6-biotin, a single band (68 kDa) corresponding to BSA/NEPP6-biotin was detected. Pretreatment with N-ethylmaleimide (NEM) depressed this signal in a dose-dependent manner, although levels of protein were virtually the same as judged from Coomassie brilliant blue staining of the gel. NEM also abolished the binding of NEPP6-biotin to lysates of HT22 cells or brain. These results suggest that cysteine thiols are the target of NEPP compounds binding to cellular proteins.

NEPPs activate HO-1 transcription through the ARE. We next studied activation of the HO-1 promoter and ARE by NEPP. In order to examine the induction of HO-1 protein by NEPP11, various concentrations of NEPP11 were added to HT22 cells for 24 h. Thereafter, cell lysates (10 µg per lane) were subjected to SDS-PAGE and probed with anti-HO-1 or anti-β-actin. We found that NEPP11 induced HO-1 protein levels approximately five-fold over baseline conditions at the same NEPP concentration that prevented neuronal cell death (Satoh et al., Eur. J. Neurosci. 17:2249-2255, 2003). Next, we studied transcriptional activation of the HO-1 gene by NEPP11 in HT22 cells, a differentiated neuronal cell line, transfected with pHO15luc, a luciferase reporter construct under the control of a 15-kb mouse HO-1 promoter fragment. HT22 cells were transfected with reporter cDNAs (1 µg per well), and various concentrations of NEPP11 were added to the cultures. After a 24-h incubation, cell lysates were subjected to luciferase reporter assays. Based on luciferase activity, NEPP11 stimulated the expression of HO-1 transcription more than five-fold in a dose-dependent manner. Similar responses were obtained with NEPP6. Gong et al. (Antioxid. Redox Signal. 4:249-257, 2002) had identified two enhancer regions, E1 and E2, located upstream of the transcriptin initiation site by approximately 4 and 10 kb that contained the elements responsible for activation by 15-deoxy-$\Delta^{12,14}$-PGJ$_2$ (Gong et al., Antioxid. Redox Signal. 4:249-257, 2002). To determine the role of the E1 and E2 enhancers, we expressed a mutant promoter construct lacking both enhancer sites [pHO15lucΔ(E1+E2)]. The mutant was only minimally responsive to NEPP11 (1.8-fold induction). Similar results were obtained with NEPP6.

The E1 and E2 enhancer sites in the H0-1 promoter each contain an ARE. Recent evidence has suggested that electrophiles can activate the ARE via the Keap1/Nrf2 pathway Itoh et al., Mol. Cell. Biol. 24:36-45, 2004; Gong et al., Antioxid. Redox Signal. 4:249-257, 2002). Because NEPP compounds have an electrophilic carbon at position #11 and can bind cysteine residues of cellular proteins, we studied this pathway of ARE activation. To provide direct evidence that NEPP11 could activate the H0-1 enhancer through an ARE, we studied transcriptional activation of a wild-type ARE core element (pAREluc) and a mutated form (pGC-AREluc) (Lee et al., Biochem, Biophys. Res. Commun. 280:286-292, 2001). cDNA constructs represented wild-type

```
pAREluc    (5'-CTCAGCCTTCCAAATCGCAGTCACAGTGACTCAG CAGAATC-3'       (SEQ ID NO: 1))
and mutant pGC-AREluc (5'-CTCAGCCTTCCAAATCGCAGTCACAGTGACTCAATAGAATC-3' (SEQ ID NO: 2))
```

(Kraft et al., J. Neurosci. 24:1101-1112, 2004). NEPP11 stimulated the wild-type transcriptional activity up to seven-fold in a dose-dependent manner, whereas the mutant was unaffected. Similar responses were obtained with NEPP6. These results strongly support the notion that NEPP compounds activate the H0-1 enhancer by activating an ARE.

Because the E1 and E2 regions also contain other enhancer elements, we tested the effects of NEPP11 (2 µM) on the expression of luciferase activity derived from these elements, including the cAMP-responsive element (CRE; p3xCREluc), AP-1 binding site (p3xAP1luc), NF-κB binding site (p3xNF-κBluc), NFAT-binding site (p3xNFATluc), ETS-binding site (p3xETSluc), and MEF2-binding site (p3xMEF2luc). The plasmid pHO15luc, used for comparison, showed greater than five-fold induction of reporter activity. In contrast, NEPP11 (2 μM) had no effect on the activity of p3xMEF2luc, slightly depressed the activities of the p3xCREluc, p3xAP1luc, p3xNFATluc, p3xETSluc constructs, and minimally activated p3xNF-κBluc expression. These results suggest that activation of these transcriptional elements plays a minor role in the activation of the HO-1 promoter by NEPP11.

To confirm that NEPP11 leads to an increase in transcription factors, including Nrf2, that bind to the ARE, we performed EMSAs. HT22 cells were incubated for 8 h with vehicle or NEPP11 (1 μM). EMSAs were performed by using 10 μg of nuclear lysates per lane and a biotin-labeled ARE probe. In one lane, anti-Nrf2 antibody (100×) was added to supershift Nrf2 protein binding to ARE probe. In another lane, an excess amount of non-labeled probe was added to the sample to compete out the labeled ARE probe from binding to proteins in the nuclear lysates. The band representing the labeled ARE probe was shifted in the presence of control cell lysates. The band representing the labeled ARE probe was shifted in the presence of control lysates, indicating binding of endogenous transcription factors to the ARE. Lysates prepared after exposure to NEPP11 (1 μM) manifest a significant increase in the intensity of this band. In contrast, the band was totally abrogated in the presence of excess unlabeled probe. Importantly, addition of anti-Nrf2 antibody produced a supershifted band, consistent with the notion that one of the transcription factors binding to the ARE under these conditions represented Nrf2.

Activation of the Keap1/Nrf2 pathway by NEPP compounds in a neuronal cell line. Next, we examined the localization of an Nrf2-Green Fluorescent Protein (GFP) fusion protein (Numazawa et al., Am. J. Physiol. 285:C334-C342, 2003) in transfected HT22 cells. HT22 cells transfected with pNrf2-GFP were treated with vehicle or NEPP11 (2 μM) for 24 h and observed under epifluorescence microscopy. Under basal conditions, the Nrf2-GFP fusion protein was predominantly localized in the cytoplasm but translocated into the nucleus upon exposure to 2 μM NEPP11. In general, Nrf2 is rapidly ubiquitinated and degraded by the proteasome pathway in the cytoplasm but becomes stable when translocated into the nucleus (Itoh et al., Mol. Cell. Biol. 24:36-45, 2004; Gong et al., Antioxid. Redox Signal 4:249-257, 2002). Thus we hypothesized that nuclear levels of Nrf2 protein should increase when cells are exposed to an electrophile such as NEPP, which promotes nuclear translocation. To test this hypothesis, cytosolic and nuclear fractions (200 μg protein) from cells that had been treated with vehicle or 2 μM NEPP11 for 24 h were precipitated and probed with anti-Nrf2 antibody and with anti-NeuN, a neuronal-specific nuclear protein. Indeed, we confirmed this hypothesis.

To elucidate the mechanism of electrophile action in this regard, we examined whether NEPP compounds bind Keap1. To examine induction of HO-1 protein by NEPP6-biotin, lysates (10 μg per lane) of HT22 cells treated with various concentrations of NEPP5-biotin were probed with anti-HO-1 or with anti-β-actin. Similar to NEPP6 and -11, we found that the conjugated product of NEPP6 and biotin (NEPP6-biotin) is neuroprotective (Satoh et al., J. Neurochem. 77:50-62, 2001). Additionally, at concentrations of 1-10 μM, NEPP6-biotin induced the expression of HO-1 protein, confirming that NEPP6-biotin retains its biological effect. We then performed immunoprecipitation experiments to provide direct evidence for adduct formation between NEPP compounds and Keap1. HT22 cells were treated with vehicle or 10 μM NEPP6-biotin, incubated for 24 h. Subsequently, lysates were prepared and subjected to precipitation with either anti-Keap1 or streptavidin. The precipitates were electrophoresed and probed. A 73-kDa protein, corresponding to Keap1 that had bound to NEPP6-biotin, was observed in cells treated with NEPP6-biotin but not with vehicle. The precipitates were also probed with anti-Keap1 to confirm that the amount of precipitated Keap1 was the same between vehicle- and NEPP6-biotin-treated cells. Next, the lysates were treated in reverse fashion, i.e., precipitated with streptavidin and then probed with anti-Keap1 antibody. Again, precipitated protein, corresponding to Keap1 that had bound to NEPP6-biotin, was detected only in the cells treated with NEPP6-biotin, but not with vehicle. Taken together, these results are consistent with the notion that NEPP compounds bind to Keap1 in cells.

To demonstrate that binding of NEPP compounds to Keap1 protein is involved in the biological actions of NEPPs, we examined the effects of a Keap1 cysteine mutant (C151S, in which cysteine residue #151 has been reported to be essential for activation of Nrf2-mediated transcription by electrophiles (Zhang and Hannink, Mol. Cell. Biol. 23:8137-8151, 2003). Overexpression of this mutant should abolish the functional link between Keap1 and Nrf2 proteins and, thus, reduce sensitivity to electrophiles, such as NEPP11. Along these lines, we found that activation of the HO-1 promoter (pHO15luc) by NEPP11 was significantly depressed by co-transfection of pKeap1(C151S), but not wild-type pKeap1.

Activation of the Keap1/Nrf2 pathway in Primary Cortical Cultures. To begin to test the effects of NEPP compounds on primary cerebrocortical neurons, we treated mixed neuronal/glial cortical cultures with NEPP6-biotin and then fixed and stained with rhodamine conjugated to streptavidin to determine the site of NEPP accumulation. Cortical cultures treated with NEPP6-biotin (10 μM) were stained with anti-MAP-2 monoclonal and rhodamine-conjugated streptavidin antibodies and with Hoechst 33,258 dye. We found that MAP-2-positive neurons stained strongly for NEPP6-biotin-streptavidin, suggesting that NEPP compounds accumulate in neurons. Incubation in biotin by itself did not result in neuronal accumulation of biotin-streptavidin, and incubation in NEPP6-biotin plus excess free biotin (4 mM) did not affect the degree of neuronal accumulation, indicating that NEPP6-biotin accumulation was not facilitated by the presence of biotin but rather by NEPP itself.

We reasoned that if, unlike other electrophiles (Kraft et al., J. Neurosci. 24:1101-1112, 2004), NEPPs accumulate predominantly in neurons, then HO-1 might be induced preferentially in this cell type. To check this possibility, we performed immunofluorescence studies with anti-HO-1 antibody after exposure to a potent NEPP compound. Cortical cultures (E17 and DIV14-21) treated with vehicle or NEPP11 (0.7 μM) were stained with anti-MAP-2 and anti-HO-1 and with Hoechst dye. In control cultures, non-neuronal cells expressed relatively more HO-1 at baseline than did neurons. After addition of NEPP11, HO-1 immunofluorescence increased mainly in neurons, in both the cytosol and nucleus. To examine induction of HO-1 protein after exposure to NEPP, lysates (10 μg per lane) of primary cortical cultures treated with vehicle or NEPP11 for 24 h were probed with anti-HO-1 or anti-β-actin in immunoblots. NEPP11 also increased total HO-1 protein in the cultures. The fold induction of HO-1 by NEPP11 was 2.2±0.25 (for 0.5 μM NEPP11) and 3.5±0.25 (for 1.0 μM NEPP11 as assessed by densitometry.

Next, transcriptional activation of the HO-1 promoter by NEPP was examined by reporter gene assays in primary neurons. Cortical cultures were transfected with reporter cDNAs (1 μg per well), and 0.7 μM NEPP11 was added to the cultures. After a 24 h incubation, cell lysates were subjected to luciferase reporter assays. In these transfected cortical cultures, NEPP11 (0.7 µM) significantly increased activity of the HO-1 promoter and ARE core element, an effect that was abrogated my mutation of the HO-1 enhancer sites or the ARE site, respectively. These results suggest that NEPP11 induced HO-1 protein in primary cortical neurons through activation of the ARE elements in the HO-1 promoter. If the Keap1/Nrf2 pathway, indeed, mediates activation of the HO-1 promoter by NEPP11, mutant Nrf2 protein should inhibit this activation. For this purpose, we used the mutated construct pNrf2 (S40A)-GFP (in which the serine residue at position #40 is replaced by an alanine); the encoded protein does not activate the ARE, because it cannot translocated into the nucleus (Numazawa et al., Am. J. Physiol. 285:C334-C342, 2003). NEPP11 significantly activated the HO-1 promoter, and cotransfection with pNrf-GFP did not affect activation. In contrast, cotransfection with pNr12(S40A)-GFP almost completely knocked down activation by NEPP11 (additionally, the basal level of HO-1 promoter activity was reduced). Taken together, our results suggest that NEPP11 activated the Keap1/Nrf2 pathway selectively in neurons. Moreover, the selective activation in neurons may explain the relatively small amplitude of total HO-1 activation seen in the mixed neuronal/glial culture system in which glia predominate.

Neuroprotection by NEPP11. Neuron-selective activation of the Keap1/Nrf2/Ho-1 pathway by NEPP compounds should provide neuroprotection. Hence, we examined the action of NEPP11 both in vitro and in vivo in excitotoxic paradigms, first in culture as a protectant from NMDA-receptor-mediated insults and then after middle cerebral artery occlusion (MCAO) by using the intraluminal filament model of transient focal ischemia/reperfusion in mice.

Exposure of primary cortical cultures to relatively mild insults, such as low concentrations of NMDA (50 µM) for short durations (15 min) is known to cause delayed and predominantly apoptotic neuronal cell death (Bonfoco et al., Proc. Natl. Acad. Sci. USA 92:7162-7166, 1995). We stained the cultures with both anti-MAP-2 and anti-NeuN monoclonal antibodies to label neuronal dendrites and nuclei, respectively. Vehicle or NEPP11 (0.7 µM) was added to cerebrocortical cultures (E17 and DIV14-21) 60 min before treatment with NMDA (50 µM) for 15 min. The cultures were then incubated for 20 h and subsequently stained with anti-MAP-2 and anti-NeuN and with Hoechst dye. Apoptotic nuclei were identified by morphological changes seen with Hoechst staining. In this system, NEPP11 significantly decreased the number of apoptotic neurons, suggesting that NEPP11 protected neurons against excitotoxicity in vitro. We also added zinc protoporphyrin (ZnPP, 10 µM), a relatively specific HO-1 antagonist, simultaneously with NEPP11. The number of apoptotic neurons was assessed by determining the apoptotic index [(number of condensed nuclei in MAP-2 or NeuN-positive cells)/(number of total MAP-2 or NeuN-positive cells)×100%], as reported by Bonfoco et al. (Proc. Natl. Acad. Sci. USA 92:7162-7166, 1995). ZnPP abrogated the neuroprotective effect of NEPP11 in these cerebrocortical cultures. This result is consistent with the notion that NEPP11 protects primary cortical neurons against excitotoxicity, at least in part, through induction of HO-1. If this antioxidant pathway is important for NEPP action, then downstream events should also be affected. Along these lines, we found that NEPP11 (1 µM) inhibited NMDA-induced caspase-3 activation. In contrast, if this is the predominant pathway, then other known anti-apoptotic genes, e.g., bcl-xL and bcl-2, might not be induced by NEPP compounds. Indeed, we found this to be the case.

One caveat to the mechanism of NEPP and other electrophilic compounds acting at the level of Keap1 to induce HO-1 transcription is that NEPP could potentially react indiscriminately with other thiol-containing compounds in cells. To approach this question, we assessed cellular glutathione (GSH) levels to determine whether NEPP11 would affect this abundant antioxidant thiol. Nepp11 or N-ethylmaleimide (NEM) was added at t=0 and levels of total GSH were measured at the indicated times. GSH content of control cortical cultures (set arbitrarily at 100%) was 46.8±4.5 nmol/mg protein. Unlike NEPP11, NEM did not produce neuroprotection in these cultures and, in fact, resulted in neuronal death after 24 h. NEPP11 did not deplete GSH levels in cortical cultures, unlike many other electrophiles that have this effect (e.g., NEM). In fact, GSH levels transiently increased after exposure to NEPP11. This increase in GSH may have occurred by induction of γ-GCL (Sagara et al., J. Biol. Chem. 277:36204-36215, 2002), the rate-limiting enzyme in GSH biosynthesis, and could also contribute to cytoprotection. In fact, this scenario seems likely, because the Keap1/Nrf2 pathway regulates the expression of γ-GCL in addition to HO-1 (Itoh et al., Mol. Cell. Biol. 24:36-45, 2004). Besides GSH, cells have another major reduction pathway representing the thioredoxin-glutaredoxin system. However, we found that NEPP11 (1 µM) did not significantly affect the expression of thioredoxin or glutaredoxin under our conditions (Example 2).

Next, we tested whether NEPP11 could decrease the size of brain infarcts after MCAO/reperfusion injury. NEPP11 or vehicle was injected intraperitoneally (i.p.) 1 h before and 4 h after MCAO. The area of brain infarction (corrected for possible edema) was assessed on coronal sections from vehicle- and NEPP11-treated mice stained with 2.5% 2,3,5-triphenyltetrazolium chloride 24 h after the onset of reperfusion. We monitored physiological variables, including arterial pressure, blood gases and glucose, core body temperature, and regional cerebral blood flow; these parameters did not differ between the control and NEPP11-treated groups. NEPP11 significantly reduced the infarct area in coronal sections, suggesting that NEPP11 is neuroprotective in vivo. We did not examine the effects of NEPP11 administered post-infarct in this study, because the drug requires several hours to exert its neuroprotective effect by transcriptional activation and therefore requires pre-treatment (Satoh et al., Eur. J. Neurosci. 17:2249-2255, 2003; Satoh et al., J. Neurochem. 77:50-62, 2001).

To test the hypothesis that NEPP protection against brain ischemia is associated with HO-1 expression, we examined HO-1 induction by Western blotting and immunostaining. NEPP11 or vehicle was injected intraperitoneally (i.p.) 12 h before the animals were killed. Brain lysates (10 µg per lane) were extracted and subjected to Western blotting with anti-HO-1 and anti-β-actin antibody. For immunostaining, coronal sections of mouse brain were stained with anti-MAP-2 and anti-HO-1 antibodies. We found that the same concentration of NEPP11 that prevented neuronal cell death during brain ischemia increased the level of HO-1 protein in the brain. Induction of HO-1 protein was observed in neuronal soma and dendrites.

Discussion. This study provides evidence that electrophilic drugs can afford neuroprotection through activation of the Keap1/Nrf2 pathway and consequent up-regulation of HO-1 and possibly other class II enzymes. It was known that up-regulation of HO-1 decreased stroke size, as assessed in HO-1 transgenic mice (Maines and Panahian, in *Hypoxia: From Genes to the Bedside*, eds. Roach et al. (New York: Kluwer), 2001, pp. 249-272). Here, we develop and characterize a set of small-molecule electrophiles that activate HO-1 transcription in neurons, showing that this pathway represents a druggable target in the brain. Successful neuroprotection by NEPP compounds involves activation of the Keap1/Nrf2 pathway at nontoxic concentrations. Many other electrophilic molecules cause systemic side effects and are not neuroprotective, probably because they also deplete critical reducing substances in the cell, such as GSH, but this is not the case with the NEPP drugs.

NEPP compounds are lipophilic, an important characteristic for their accumulation in neurons, as demonstrated in this study with labeled NEPP (NEPP-biotin). Kraft et al. (J. Neurosci. 24:1101-1112, 2004), however, reported that another electrophile, tert-butylhydroquinone (TBHQ), activates the ARE in astrocytes, a fact that may appear inconsistent with our observations. Nevertheless, it should be noted that the chemical structures of electrophiles such as NEPP and TBHQ vary widely and may affect their cellular uptake (Kraft et al., J. Neurosci. 24:1101-1112, 2004). Hence, one electrophile may very well localize to astrocytes, whereas another predominates in neurons, as observed here for NEPP compounds. NEPP compounds ($\Delta^7$-prostaglandinA$_1$ analogues) have been molecularly designed based on the chemical structure of $\Delta^{12}$-prostaglandinJ$_2$, and these molecules share many chemical and biological properties (Fukushima, Eicosanoids 3:189-199, 1990). $\Delta^{12}$-prostaglandinJ$_2$ is reportedly transported into cells by active transport through the cell membrane (Narumiya et al., J. Pharmacol. Exp. Ther. 239: 506-511, 1986). Therefore, neurons may have a more active transport system for NEPP compounds than do glia, because we observed that NEPP compounds accumulate preferentially in neurons. In contrast, the electrophile TBHQ may simply diffuse into cells and, thus, affect glia, which greatly outnumber neurons.

Our findings suggest the neuroprotective mechanism of NEPP action. Within cells, these drugs bind to the cytosolic regulator protein Keap1, which, in turn, liberates Nrf2. Nrf2 is then translocated into the nucleus, where it activates AREs on the HO-1 promoter (Itoh et al., Mol. Cell. Biol. 24:36-45, 2004; Gong et al., Antioxid. Redox Signal. 4:249-257, 2002). Transcription of HO-1 is thus activated in neurons, and an increase in HO-1 protein leads to degradation of heme molecules, producing biliverdin and bilirubin (Itoh et al., Mol. Cell. Biol. 24:36-45, 2004; Gong et al., Antioxid. Redox Signal. 4:249-257, 2002). The accumulation of bilirubin, a potent antioxidant molecule, is responsible, at least in part, for the neuroprotective effects of HO-1, and thus of NEPP compounds (Satoh et al., Eur. J. Neurosci. 17:2249-2255, 2003; Sagara et al., J. Biol. Chem. 277:36204-36215, 2002). Additionally, we found that inhibition of HO-1 by zinc protoporphyrin prevented the protective effect of NEPP, consistent with the notion that the therapeutic action of these drugs is mediated predominantly by this pathway.

Recently, decreased Nrf2 transcriptionally activity was also reported to cause age-related loss of GSH synthesis (Suh et al., Proc. Natl. Acad. Sci. USA 101:3381-3386, 2004). Low molecular-weight compounds can induce $\gamma$-GCL through activation of the ARE to increase GSH levels. Thus, compounds that regulate the Keap1/Nrf2 pathway may be promising candidates for neuroprotection against free radical stress through induction of $\gamma$-GCL as well as HO-1, both of which help prevent accumulation of reactive oxygen species.

In summary, we found that modulation of the Keap1-Nrf2 pathway by NEPP compounds leads to activation of the HO-1 promoter by Nrf2. Induction of HO-1 protein is known to play an important neuroprotective role against excitotoxicity and brain ischemia (Maines and Panahian, in *Hypoxia: From Genes to the Bedside*, eds. Roach et al. (New York: Kluwer), 2001, pp. 249-272; Stocker et al., Science 235:1043-1046, 1987; Dore et al., Proc. Natl. Acad. Sci. USA 96:2445-2450, 1999; Poss and Tanegawa, Proc. Natl. Acad. Sci. USA 94:10925-10930, 1997; Satoh et al., Eur. J. Neurosci. 17:2249-2255, 2003; Satoh et al., J. Neurochem. 77:50-62, 2001). How can clinically useful drugs be developed based on the chemical structures of cyclopentenone prostaglandins like the NEPPs? One approach is to synthesize neuroprotective electrophilic drugs like the NEPPs that spare essential redox elements. Strongly electrophilic compounds are known to deplete the cell of critical thiol-containing compounds like GSH and, hence, contribute to cell death. In contrast, NEPP compounds and their congeners interact with Keap1 without depleting GSH. Selective activators of the Keap1/Nrf2 pathway are neuroprotective agents that act through induction of phase 2 genes, including HO-1.

EXAMPLE 2

Methods and Materials

Focal Cerebral Ischemia and Reperfusion. NEPP11 was injected at 100 mg/ml in a 7.5% solution of DMSO in PBS; controls received the diluent alone. The investigator was blinded as to the treatment group. The injected volume was 10 ml/g of body weight, corresponding to 1 mg/kg. The intraluminal-filament model of middle cerebral artery occlusion (MCAO)/reperfusion was used (Gu et al., Science 297:1186-1190, 2000). Male mice (C57BL/6) at age 6-8 weeks and weighing 20-30 g were housed in a 12 hr light/12 hr dark cycle and permitted food and water intake ad libitum. The animals were anesthetized with an isoflurane and 70% nitrous oxide/ 30% oxygen mixture delivered through a nose cone. Core temperature was maintained at 37±1° C. Other physiological parameters were monitored, including systemic blood pressure, glucose, and arterial blood gasses and pH. The mice underwent a 2 hr MCAO followed by a 24 hr reperfusion period. Occlusion and reperfusion of blood flow were monitored by laser Doppler flowmetry. Anesthesia was maintained for the duration of the surgical procedure, which typically lasted 10 min in our hands.

After the reperfusion period, the animals were killed. The brains were then sliced into sections of 2 mm thickness. Each slice was incubated for 10 min in a 2.5% solution of 2,3,5-triphenyltetrazolium chloride at 37° C. and fixed in 4% buffered formaldehyde solution. Areas of infarction occurred in the right middle cerebral artery territory of each brain slice and were quantified with a computerized image analysis system (NIH image 1.62) as described (Gu et al., Science 297: 1186-1190, 2000).

Cell Cultures, Transfection, and Glutathione (GSH) Measurement. HT22 cells were cultured as described (Satoh et al., Eur. J. Neurosci. 17:2249-2255, 2003; Satoh et al., J. Neurochem. 77:50-62, 2001; Sagara et al., J. Biol. Chem. 277: 36204-36215, 2002). Cerebrocortical cultures were prepared from embryonic day-17 Sprague-Dawley rats and used at day 14-21 in vitro (DIV14-21), as described (Bonfoco et al., Proc. Natl. Acad. Sci. USA 92:7162-7166, 1995). To induce predominantly neuronal apoptosis (rather than necrosis), we exposed cortical cultures to 50 mM NMDA plus 5 mM glycine/1.8 mM CaCl$_2$ in nominally Mg$^{2+}$-free Earle's balanced salt solution for 15 min (Bonfoco et al., Proc. Natl. Acad. Sci. USA 92:7162-7166, 1995). After exposure to NMDA, the cultures were returned to normal medium containing vehicle or NEPP11 and incubated for 20 hr before analyzing cell survival. To assess the ability of NEPP compounds to block NMDA-induced neuronal apoptosis, we identified apoptotic neurons by double immunofluorescence with anti-NeuN and anti-MAP-2 to specifically label neurons and with Hoechst staining for nuclear morphology to detect apoptosis. The percentage of neurons and non-neuronal cells in our cultures was 33.6±4.9% and 66.4±4.4% (n=4), respectively.

Transfections were performed with Lipofectamine 2000 (Invitrogen), and firefly luciferase activity in cell lysates was measured with a luminometer in the reporter gene assays (Promega). Total GSH (reduced and oxidized) was determined as described (Sagara et al., J. Biol. Chem. 277:36204-36215, 2002).

Results

Lack of Effect of NEPP Compounds on Expression of Trx and Grx Genes. The expression of Trx1/2 and Grx112 was examined in cortical cultures incubated with NEPP11(1 mM) for 24 hr by using RT-PCR with the following primers (Jurado et al., J. Bioi. Chem. 278:45546-45554, 2003): Trx1, forward: 5'-CGT GGT GGA CTT CTC TGC TAC GTG GTG-3' (SEQ ID NO: 3); reverse: 5'-GGT CGG CAT GCA TTT GAC TTC ACA GTC-3' (SEQ ID NO: 4); Trx2m, forward: 5'-GCT AGA GAA GAT GGT CGC CAA GCA GCA-3' (SEQ ID NO: 5); reverse: 5'-TCC TCG TCC TTG ATC CCC ACA AAC TTG-3' (SEQ ID NO: 6); Grx-1, forward: 5'-TGC AGA AAG ACC CAA GAA ATC CTC AGT CA-3' (SEQ ID NO: 7); reverse: 5'-TGG AGA TTA GAT CAC TGC ATC CGC CTA TG-3' (SEQ ID NO: 8); Grx-2, forward: 5'-CAT CCT GCT CTT ACT GTT CCA TGG CCA A-3' (SEQ ID NO: 9); reverse: 5'-TCA TCT TGT GAA GCG CAT CTT GAA ACT GG-3' (SEQ ID NO: 10). We found that NEPP11 (1 mM) did not significantly affect expression of the Trx and Grx genes under the conditions of our assay.

EXAMPLE 3

Glutamate, the major excitatory amino acid in the brain, exerts various actions on neurons, affecting development, plasticity, and survival (Nakanishi, Trends Neurosci. 28:93-100, 2005; Barco et al., J. Neurochem. 97:1520-1533, 2006). Under physiological conditions, glutamate plays a major role in learning and memory in part via NMDA receptor-mediated pathways (Nakanishi, Trends Neurosci. 28:93-100, 2005; Barco et al., J. Neurochem. 97:1520-1533, 2006). However, under pathological conditions, glutamate can induce neuronal cell death, termed "excitotoxicity," predominantly by excessive activation of the NMDA receptor (Choi, J. Neurosci. 23:1261-1276, 1992; Ankarcrona et al., Neuron 15:961-973, 1995; Hara and Snyder, Annu. Rev. Pharmacol. Toxicol. 47:117-141, 2007) and in part owing to the subsequent generation of free radicals such as nitric oxide (NO) and reactive oxygen species (ROS). In immature neurons, which have not yet expressed functional NMDA receptors, high concentrations of glutamate induce a novel type of neuronal death mediated by depletion of reduced glutathione (GSH), termed "oxidative glutamate toxicity" (Murphy et al., Neuron 2:1547-1558, 1989; Murphy et al., FASEB J. 4:1624-1633, 1990; Dargusch and Schubert, J. Neurochem. 81:1394-1400, 2002). Although these two types of neuronal death induced by glutamate are distinct from each other, oxidative stress is involved in both types (Murphy et al., Neuron 2:1547-1558, 1989; Coyle and Puttfarcken, Science 262:689-695, 1993; Dugan et al., J. Neurosci. 15:6377-6388, 1995). For this reason, several antioxidant molecules have been reported to protect neurons against both excitotoxicity and oxidative glutamate toxicity (Murphy et al., FASEB J. 4:1624-1633, 1990; Ankarcrona et al., Neuron 15:961-973, 1995; Dargusch and Schubert, J. Neurochem. 81:1394-1400, 2002). Thus, one strategy for the development of neuroprotective drugs is to search for low-molecular-weight compounds that can regulate redox state and thereby counter oxidative damage (Satoh and Lipton, J. Neurochem. 75:1092-1102, 2007).

Recently, our group, in addition to those of Johnson and Murphy, reported that a series of compounds not necessarily possessing antioxidative activity themselves could nonetheless transcriptionally induce antioxidative enzymes to afford neuroprotection (Satoh et al., Proc. Nat. Acad. Sci. USA 103:768-773, 2006; Kraft et al., J. Neurosci. 24:1101-1112, 2004; Shih et al., J. Neurosci. 25:10321-10335, 2005). Such electrophilic compounds have an advantage over antioxidant molecules because their action is more sustained and amplified by transcription-mediated signaling pathways (Satoh and Lipton, Trends Neurosci. 30:38-45, 2007). Electrophiles induce the expression of a set of antioxidant enzymes, called "phase 2 enzymes," including heme oxygenase-1 (HO-1), NADPH quinone oxidoreductase 1 (NQO1), and γ-glutamyl cysteine ligase (γ-GCL), all of which provide efficient cytoprotection by regulating the intracellular redox state (Talalay, Biofactors 12:5-11, 2000; Padmanabhan et al., Mol. Cell 21:689-700, 2006; Itoh et al., Free Radic. Biol. Med. 36:1208-1213, 2004). Representing a specific transcriptional element located in the 5' upstream promoter region of genes that encode phase 2 enzymes, the antioxidant-responsive element (ARE) plays a central role in the induction of such enzymes (Talalay, Biofactors 12:5-11, 2000; Padmanabhan et al., Mol. Cell 21:689-700, 2006; Itoh et al., Free Radic. Biol. Med. 36:1208-1213, 2004). A key cascade involved is termed the Keap1/Nrf2 pathway, which is comprised of Keap1, a regulator protein, and Nrf2, a transcription factor that binds to the ARE. Keap1 is an adapter protein that facilitates ubiquitination of Nrf2 and thus drives constitutive degradation of this transcription factor. When electrophiles react with critical cysteine residues on the Keap1 protein to form an adduct, they perturb this system, thereby stabilizing Nrf2 and allowing it to be translocated from the cytoplasm into the nucleus, where it binds to AREs and stimulates the transcription of phase 2 genes (Talalay, Biofactors 12:5-11, 2000; Padmanabhan et al., Mol. Cell 21:689-700, 2006; Itoh et al., Free Radic. Biol. Med. 36:1208-1213, 2004).

Figure 2:
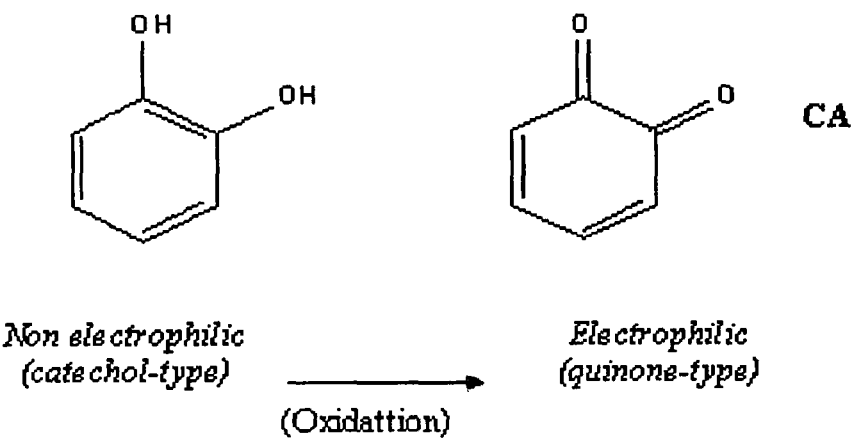
FIG. 2 shows core chemical structures of neuroprotective electrophilic compounds of the catechol and enone types.
Figure 2:
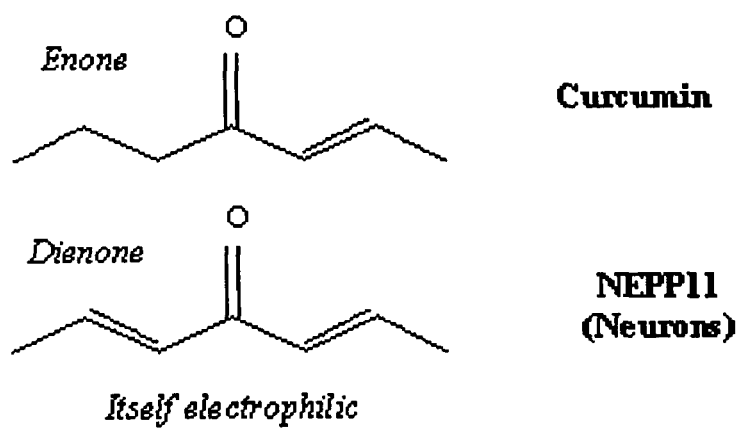

Neuroprotective electrophilic compounds reported previously may be divided into two major groups, catechol- and enone-types, as shown in FIG. 2 (Kraft et al., J. Neurosci. 24:1101-1112, 2004; Satoh et al., Proc. Nat. Acad. Sci. USA 103:768-773, 2006; Satoh and Lipton, Trends Neurosci. 30:38-45, 2007). These two types of compounds manifest distinctive features. One difference lies in their degree of electrophilicity. Enone-type electrophilic compounds, including the enone-type curcumin (Yazawa et al., FEBS Lett. 580:6623-6628, 2006) and dienone-type NEPP11 (Satoh et al., Proc. Nat. Acad. Sci. USA 103:768-773, 2006), are themselves electrophilic. In contrast, catechol-type compounds are not themselves electrophilic but become electrophilic by oxidative conversion to a quinone (Nakamura et al., Biochem. 15:4300-4309, 2003). Thus, these catechol-type compounds function as prodrugs, which require conversion from catechol to quinone to exert their neuroprotective effect (Satoh and Lipton, Trends Neurosci. 30:38-45, 2007). Another distinctive difference between the catechol-type and quinone-type is their distribution in neuronal cultures. Tert-butyl hydroquinone (TBHQ), a catechol-type neuroprotective electrophilic compound, reportedly acts preferentially in astrocytes and protects neurons by a paracrine mechanism (Ahlgren-Beckendorf et al., Glia 15:131-142, 1999; Lee et al., J. Biol. Chem. 278:12029-12038, 2003; Kraft et al., J. Neurosci. 24:1101-1112, 2004). In contrast, NEPP11, an enone-type neuroprotective electrophilic compound, accumulates in neurons to induce HO-1, thereby exerting a direct protective action on neurons (Satoh et al., Proc. Nat. Acad. Sci. USA 103:768-773, 2006).

Since plants produce a variety of electrophilic compounds, we looked for naturally-occurring electrophilic compounds in plants of the catechol-type that might protect neurons through transcriptional activation. Carnosic acid is a naturally-occurring catechol-type poly-phenolic diterpene obtained from *Rosmarinus officinalis* (rosemary) and comprises about 5% of the dry weight of rosemary leaves (Kosaka and Yokoi, Bio. Pharm. Bull. 26:1620-1622, 2003). CA reportedly has various biological actions, possibly effected through phosphatidylinositol 3-kinase (Martin et al., J. Biol. Chem. 279:8919-8929, 2004), peroxisome proliferator-activated receptor (PPAR). (Rau et al., Planta Med. 72:881-887, 2006), cyclin A/B1 (Visanji et al., Cancer Lett. 237:130-136, 2006), and free radical-scavenging activity (Aruoma et al., Xenobiotica 22:257-268, 1992).

Electrophilic compounds are a newly-recognized class of redox-active neuroprotective compounds with electron deficient, electrophilic carbon centers that react with specific cysteine residues on targeted proteins via thiol (S-) alkylation. Although plants produce a variety of physiologically-active electrophilic compounds, the detailed mechanism of action of these compounds remains unknown. Catechol ring-containing compounds have attracted attention because they become electrophilic quinones upon oxidation, although they are not themselves electrophilic. We found that CA activates the Keap1/Nrf2 transcriptional pathway by binding to specific Keap1 cysteine residues, thus protecting neurons from oxidative stress and excitotoxicity. In cerebrocortical cultures, CA-biotin accumulates in non-neuronal cells at low concentrations and in neurons at higher concentrations. Both the neuronal and non-neuronal distribution of CA may contribute to its neuroprotective effect. Furthermore, CA translocates into the brain, increases the level of reduced glutathione in vivo, and protects the brain against middle cerebral artery ischemia/reperfusion.

Materials and Methods

Chemicals. Fraction V bovine serum albumin (BSA), 4',6-diamino-2-phenylindole (DAPI), dimethyl sulfoxide (DMSO), fluorescein diacetate (FDA), glutamate, Hoechst 33,258, reduced glutathione (GSH), GSSG, oxidized glutathione (GSSG), 3-(4,5-dimethylthiazol-2-yl)-2,5-diphenyl tetrazolium bromide (MTT), N-ethylmaleimide (NEM), N-methyl-D-aspartate (NMDA), propidium iodide (PI), and rotenone, 2,3,5-triphenyltetrazolium chloride (TTC) were purchased from WAKO Chemicals Inc. (Tokyo, Japan) or Sigma (St. Louis, Mo.).

CA and CA-biotin (CAB). CA was extracted from rosemary leaves as previously described (Kosaka and Yokoi, Biol. Pharm. Bull. 26:1620-1622, 2003). CA-biotin (CAB) was synthesized according to Kosaka and Yokoi (Biol. Pharm. Bull. 26:1620-1622, 2003) by the following method: Carnosic acid (90 mg), acetonitrile (2 ml), and dicyclohexylcarbodiimide (67 mg; Tokyo Kasei Kyogyo Co., Tokyo, Japan) were mixed for three min on ice. Then, 5-(biotinamido)pentylamine (41 mg; Pierce, Rockford, Ill.), dissolved in 80% acetonitrile, was added to the mixture, which was subsequently incubated for 10 min on ice. Thereafter, hydrochloric acid was added to terminate the reaction. The reaction product was separated by preparative liquid chromatography (ODS column consisting of ODS-S-50c (Maruzen Co., Tokyo, Japan) with acetonitrile and hydrochloric acid as solvent. Both CA and CAB were prepared as 10 mM stock solutions in DMSO.

Western blotting for CAB. BSA with or without CAB was separated by 10% SDS-polyacrylamide gel electrophoresis and then electrophoretically transferred to a nitrocellulose membrane (Amersham Life Science, Piscataway, N.J.). Next, the membrane was blocked for 1 h at room temperature in $Ca^{2+}$, $Mg^{2+}$(-)-phosphate-buffered saline containing 0.1% Tween 20 (PBS-T) and 5% non-fat dry milk and then incubated for 1 h with horseradish peroxidase-conjugated streptavidin. After the membrane had been washed 3 times with PBS-T, signals were detected using ECL Western blotting detection reagents (Amersham Pharmacia Biotech, Piscataway, N.J.).

Antibodies. Anti-Nrf2 and anti-Keap1 monoclonal mouse IgGs were generated by Ken Itoh (Hirosaki University). Other antibodies used were FITC-conjugated anti-mouse IgG, rhodamine-conjugated anti-mouse IgG, rhodamine-conjugated anti-rabbit IgG, peroxidase-conjugated anti-rabbit IgG, rhodamine-conjugated streptavidin (Jackson Immuno Research Laboratories, Westgrove, Pa.), anti-S100β monoclonal antibody, peroxidase-conjugated streptavidin, streptavidin immobilized on 4%-beaded agarose (Pierce, Rockford, Ill.), anti-HA monoclonal antibody, and anti-MAP-2, and anti-NeuN monoclonal mouse IgGs, and protein A immobilized on Sepharose CL-4B (Sigma, St Louis, Mo.).

Plasmid constructs.

(1) pGL3-GSTYa ARE core-luciferase vector. We used single-stranded oligonucleotide containing the GSTYa ARE core sequence (Wasserman and Fahl, Proc. Nat. Acad. Sci. USA 94:5361-5366, 1997): sense, 5'-CGC GTT AGC TTG GAA ATG ACA TTG CTA ATG GTG ACA AAG CAA CTT TA-3' (SEQ ID NO: 11), and antisense, 5'-GAT CTA AAG TTG CTT TGT CAC CAT TAG CAA TGT CAT TTC CAA GCT AA-3' (SEQ ID NO: 12). The dsDNA thus obtained was inserted into the Mlu 1 and Bglll sites of the pGL3-promoter vector (Promega Co., Madison, Wis.).

(2) pEF6-Nrf2 [wild-type (Nrf2WT)], pEF6-Nrf2 [dominant-negative (Nrf2DN)]. and pEF6-Keap1 vectors. Nrf2WT, and Nrf2DN were generated by polymerase chain reaction (PCR) amplification of mouse eDNA with the following oligonucleotides: sense for Nrf2WT 5'-GCC ATG ATG GAC TTG GAG TTG CCA CCG CCA-3' (SEQ ID NO: 13), sense for Nrf2DN 5'-GCC ATG GGT GAA TCC CAA TGT GAA AAT ACA-3' (SEQ ID NO: 14), and common antisense 5'-GTT TTT CTT TGT ATC TGG CIT CIT GCT TTT-3' (SEQ ID NO: 15) (Aiam et al., J. Bioi. Chern. 274:26071-26077, 1999). To obtain a Keap1 expression vector, we generated Keap1 cDNA using sense 5'-CCA CCA TGC AGC CCG AAC CCA AGC TTA GC-3' (SEQ ID NO: 16) and antisense 5'-AAG CAA AIT GAT CAA CAA AAC TGT ACC TGC-3' (SEQ ID NO: 17). The amplification products were cloned into the pEF6 vector (Invitrogen, Carlsbad, Calif.).

(3) Expression vectors for HA-tagged Keap1 and Keap1 deletion mutants. These constructs were obtained from Dr. Akira Kobayashi of Tohoku University (Hosoya et al., J. Biol. Chem. 29:27244-27250, 2006; Kobayashi et al., Mol. Cell. Biol. 26:221-229, 2006).

PC12h and COST cell cultures. Cell lines were cultured and analyzed for cell death assays as previously described (Satoh et al., J. Neurochem. 75:1092-1102, 2000; Satoh et al., J. Neurochem. 77:50-62, 2001; Satoh et al., Eur. J. Neurosci. 17:2249-2255, 2003). For generation of stable transformants, PC12h cells were seeded onto 100-mm petri dishes in Dulbecco's Modified Eagle medium supplemented with 8% fetal calf serum and 8% horse serum (Invitrogen, Carlsbad, Calif.). The cells were then transfected with pEF6-Nrf2WT or pEF6-Nrf2DN using TransFast (Promega Co., Madison, Wis.). The following day, the medium was replaced with fresh medium containing 30 µg/ml blastcidine. After two weeks, five colonies of each type of transfectant were isolated. We screened for high (PC12hW1B) and low (PC12hD5D)-expressing γ-GCL clones by RT-PCR. We found that ARE activity was high in PC12hW1B and low in PC12hD5D cells, suggesting that the levels of γ-GCL and ARE activity were well correlated. Expression of the Nrf2WT and Nrf2DN constructs was confirmed by RT-PCR RT-PCR. In order to examine phase 2 gene induction by CA in PC12h cells and brain lysates, RT-PCR of total RNA from cortical cultures was performed using the following primer pairs (Hosoya et al., J. Bioi. Chern. 29:27244-27250, 2005; Kobayashi et al., Mol. Cell. Biol. 26:221-229, 2006): CypA (89 bp), 5'-ACA GGT CCT GGC ATC TTG TC-3' (SEQ ID NO: 18)(sense) and 5'-AGCCACTCAGTCTTG-GCAGT -3' (SEQ ID NO: 19)(antisense); H0-1 (284 bp), 5'-CAG TCG CCT CCA GAG TTT CC -3' (SEQ ID NO: 20)(sense) and 5'- TAC AAG GAG GCC ATC ACC AGC-3' (SEQ ID NO: 21)(antisense); GCL-M (280 bp), 5'- CTG CTA AAC TGT TCA TTG TAG G-3' (SEQ ID NO: 22)(sense) and 5'- CTA TTG GGT TIT ACC TGT G-3' (SEQ ID NO: 23) (antisense); GCL-C (213 bp), 5'- GTC TIC AGG TGA ACA TIC CAA GC-3' (SEQ ID NO: 24)(sense) and 5'- TGT TCT TCA GGG GCT CCA GTC-3' (SEQ 10 NO: 25)(antisense); and NQO1 (212 bp), 5'- GTG TAC AGC ATI GGC CAC AC-3' (SEQ 10 NO: 26)(sense) and 5'AAA TGA TGG CCC ACA GAA AG-3' (SEQ ID NO: 27)(antisense).

Primary cortical cultures and assays for two types of glutamate toxicity. Cerebrocortical neurons have been used as an in vitro system in order to investigate the cellular mechanism of neuronal death caused by glutamate. The level of expression of functional NMDA receptors is key for determining whether excitotoxicity or oxidative glutamate toxicity predominates. With increasing days in vitro (DIV), the expression level of these receptors in cortical cultures increases. In these immature cortical cultures, which do not yet express functional NMDA receptors, oxidative glutamate toxicity is dominant; and high concentrations of glutamate (2 mM) induce cell death via oxidative stress (Murphy et al., FASEB J. 4:1624-1633, 1990; Lee et al., J. Biol. Chem. 278:37948-37956, 2003). In light of this background information, in the present study, we prepared cerebrocortical cultures from embryonic day 17 (E17) Sprague-Dawley rats and examined them at DIV2 as an experimental system for oxidative glutamate toxicity (Murphy et al., FASEB J. 4:1624-1633, 1990; Lee et al., J. Biol. Chem. 278:37948-37956, 2003). Rotenone, a complex I inhibitor of the mitochondrial electron-transport chain, also induces oxidative stress in immature cortical cultures (Murphy et al., FASEB J. 4:1624-1633, 1990; Lee et al., J. Biol. Chem. 278:37948-37956, 2003).

In addition, we used mature cortical cultures (E17, DIV21) to assess excitotoxicity because functional NMDA receptors are expressed on these neurons. Exposure of mature cortical cultures to relatively mild insults, such as low concentrations of NMDA (50 µM) for short durations (15 min) has been shown to cause delayed and predominantly apoptotic neuronal cell death in this system; in contrast, higher concentrations of NMDA for longer exposure times result in necrosis (Bonfoco et al., Proc. Nat. Acad. Sci. USA 92:7162-7166, 1995; Budd et al., Proc. Nat. Acad. Sci. USA 97:6161-6166, 2000). To induce predominantly neuronal apoptosis (rather than necrosis), we exposed cortical cultures to 50 µM NMDA for 15 min (plus co-agonist 5 µM glycine in 1.8 mM $CaCl_2$, nominally $Mg^{2+}$-free Earle's balanced salt solution (EBSS) to prevent magnesium-mediated block of NMDA receptor-operated channels) (Bonfoco et al., Proc. Nat. Acad. Sci. USA 92:7162-7166, 1995). After exposure to NMDA, the cultures were returned to normal medium containing vehicle or CA, and then incubated for 20 h prior to analyzing them for cell survival. CA or vehicle was present 1 h before the addition of NMDA and remained throughout the experiments. To assess the ability of CA to block NMDA-induced neuronal apoptosis, we identified apoptotic neurons by double immunofluorescence labeling with anti-NeuN and anti-MAP-2 to specifically label neurons, and with Hoechst staining for nuclear morphology to detect apoptosis. The percentage of neurons and non-neuronal cells in these mature cortical cultures (E17, DIV21) was 33.6±4.9% and 66.4±4.4%, respectively, as determined by use of specific markers (Satoh et al., Proc. Nat. Acad. Sci. USA 103:768-773, 2006). In the immature cortical cultures (E17, DIV2), the percentage of neuronal cells was over 90% (Satoh et al., J. Neurochem. 77:50-62, 2001).

Immunocytochemistry. Cultures were fixed with 3% paraformaldehyde at room temperature for 20 min. After three washes in PBS, the cells were permeabilized with 0.3% Triton X-100 for 5 min. After three additional washes in PBS, the cells were incubated at 4° C. overnight with primary antibodies. They were then washed three times in PBS containing 0.2% Tween 20 (PBS-T), and next incubated with secondary antibodies for 1 h at room temperature. Thereafter, the cells were again washed, and their nuclei stained with Hoechst 33,258 (5 µg/ml) or with DAPI (1 µg/ml) for 5 min. Stained preparations were mounted and examined by epifluorescence microscopy. The following primary antibodies were used: anti-Nrf2 antibody, anti-MAP2 and anti-NeuN antibodies to identify neurons (dendrites and nuclei, respectively), and anti-S100β antibody to identify astrocytes. As secondary antibodies, we used FITC-conjugated anti-mouse IgG, rhodamine-conjugated anti-mouse IgG, or rhodamine-conjugated streptavidin.

Transient transfection and measurement of luciferase activity. PC12h cells or cerebrocortical cultures (E17, DIV21) were incubated for 5 h in EBSS containing 1 µg of a plasmid DNA plus Lipofectamine 2000 (Invitrogen, Carlsbad, Calif.). Transfection efficiency was normalized to β-galactosidase activity expressed by co-transfection with pSV-β-gal (Promega). For reporter gene assays, cells were transfected with 1 µg of the reporter construct [ARE (GSTYa)-luciferase] and 0.2 µg pSV-β-gal for 1 hour. The cells were then washed in PBS alone and incubated in the culture medium for another 24 h with or without CA. Firefly luciferase activity and β-galactosidase activity in cell lysates were measured using a Luciferase System and β-Galactosidase Enzyme Assay System, respectively (Promega, Madison, Wis.).

Immunoprecipitation with agarose-immobilized streptavidin or antibody. PC12h cells (CAB- or vehicle-treated) were lysed in RIPA buffer supplemented with protease inhibitor cocktail. The lysates were centrifuged at 15,000 rpm for 10 min at 4° C., after which the supernatants were incubated with agarose-immobilized streptavidin at 4° C. for 1 h. Alternatively, for immunoprecipitation with anti-Keap1, the cell lysates were incubated with the antibody at 4° C. overnight, after which protein A immobilized on Sepharose CL-4B was added and incubation continued at 4° C. for 1 h. Then, the complexes were washed three times with rinse buffer (150 mM NaCl, 50 mM Tris-HCl [pH 7.5], 0.1% NP-40, 1 mM EDTA, and 0.02% NaN3). SDS sample buffer was added, the mixture was boiled for 5 min, and the supernatants were subjected to SDS-PAGE. Immunoblotting was then performed as described above.

Translocation of CA into the brain detected by high-performance liquid chromatography (HPLC). For experiments testing penetration of drug into the CNS, we used adult male C57BL/6 mice (Charles River) weighing 22-26 g. The mice were kept in cages with ad libitum access to food and water under standardized housing conditions (natural light-dark cycle, temperature of 23±3° C., relative humidity of 50±10%). After a seven-day adaptation to laboratory conditions, the animals were randomly assigned to each experimental group (n=10 mice each). Four C57 BL/6 mice, fastened for 18 h, were each orally administered 3 mg of CA in 0.3 ml olive oil. One and three h after the injection, under ether anesthesia, serum and brain were isolated for chemical analysis. CA was extracted from tissue with acetonitrile and ethanol. CA levels were obtained by HPLC (column, µBondasphere C18; temperature, 40 C; HPLC system, Shimadzu [Kyoto, Japan] LC10Avp; detector, UV 230 nm; running solvent 2% acetic acid or acetonitrile, 30% B isocratic at 1 ml/min).

Measurement of brain GSH. After exsanguination via heart puncture under ether anesthesia, mouse brains were removed and quickly frozen in liquid nitrogen. We ruled out GSH as a contaminant from blood vessels by HPLC analysis of blood components in the brain lysates. Along these lines, we observed a major unknown peak (retention time 12.5 min, probably representing a degradation product of CA) in the serum of CA-injected mice; however, this peak was not detected in the brain lysates, indicating that contamination from the blood did not occur under our conditions.

The frozen brains were lysed with 1% sulfosalicylic acid on ice for 10 min, and total glutathione (reduced and oxidized) was determined as described previously (Sagara et al., 2002). Briefly, after the lysates had been incubated on ice for 10 min, the supernatants were collected after centrifugation in Eppendorf microfuge tubes. Upon neutralization of each supernatant with triethanolamine, the total glutathione (reduced and oxidized) concentration was determined. Pure GSH was used to obtain the standard curve. For the determination of oxidized GSH, the method of Griffith using 2-vinylpyridine was used to deplete the reduced GSH.

Focal cerebral ischemia and reperfusion. CA (1 mg/kg) was injected intraperitoneally in a vehicle of 10% DMSO in PBS (10 µl/g body weight); controls received vehicle alone. The investigator was blinded to the treatment group. The intraluminal filament model of middle cerebral artery occlusion (MCAO)/reperfusion was utilized, as previously described (Wang et al., Nat. Med. 4:228-231, 1998; Gu et al., Science 297:1186-1190, 2002; Gu et al., J. Neurosci. 25:6401-6408, 2005; Satoh et al., Proc. Nat. Acad. Sci. USA 103:768-773, 2006). Male C57/BL/6 mice, aged 6-8 weeks and weighing 20-30 g, were housed in a 12-h light/12-h dark cycle and permitted food and water intake ad libitum. After an overnight fast, the animals were anesthetized with an isoflurane and 70% nitrous oxide/30% oxygen mixture delivered through a nose cone. Anesthesia was maintained for the duration of the surgical procedure, which typically lasted 10 min in our hands. To ensure successful placement of the intraluminal suture for occlusion and subsequent reperfusion, we monitored regional cerebral blood flow (rCBF) in the area of the right middle cerebral artery in all animals. A laser Doppler flowmeter (Perimed, North Royalton, Ohio) with the probe fixed on the skull surface (3 mm lateral to midline and 2 mm posterior to the bregma), located at the distal arterial supply of the middle cerebral artery, measured rCBF, as described previously (Wang et al., Nat. Med. 4:228-231, 1998; Gu et al., Science 297:1186-1190, 2002; Gu et al., J. Neurosci. 25:6401-6408, 2005). All mice subjected to a 2-h right MCAO met the criteria that the rCBF was reduced to <25% of the baseline during ischemia and recovered to >50% of the baseline within 2 h after the onset of reperfusion. Core temperature was maintained at 37±1° C. with a servo-controlled heating blanket. We monitored other physiological variables, including arterial blood pressure, blood gases and glucose, and these parameters did not differ significantly between vehicle- and CA-treated mice. The right femoral artery was cannulated to monitor blood pressure and sample arterial blood gases and glucose. Blood pressure was continually recorded before ischemia, during ischemia, and at reperfusion with a blood-pressure transducer, a bridge amplifier, and a computerized data acquisition system (MacLabs 8s; ADInstruments, Castle Hill, New South Wales, Australia). Arterial blood gases and glucose were measured before ischemia and 15 min after reperfusion with a blood gas and glucose analyzer (Stat Profile Ultra C; Nova Biomedical, Waltham, Mass.).

After mice underwent 2-h MCAO followed by 24-h reperfusion, they were sacrificed and their brains sliced into 1-mm thick sections. Each slice was incubated for 10 min in a 2.5% solution of TTC at 37° C. and then fixed in 4% buffered formaldehyde solution for storage. To minimize the effect of brain edema, infarct volume was determined by subtracting the volume of the contralateral noninfarcted hemisphere (left) from the ipsilateral hemisphere (right). Infarction occurred in the right MCA territory and was quantified with a computerized image analysis system (NIH image, Version 1.62), as described previously (Wang et al., Nat. Med. 4:228-231, 1998; Gu et al., Science 297:1186-1190, 2002; Gu et al., J. Neurosci. 25:6401-6408, 2005).

Statistical analysis. Each experiment was repeated at least three times in quadruplicate. Data are presented as mean±SEM. Statistical significance was determined by an analysis of variance (ANOVA) followed by a post hoc Schéffe's test.

Results

CA binds to gsh and protein thiol. CA has been proposed to donate protons and electrons to oxygen and other oxygen radicals, as suggested in the case of TBHQ (Nakamura et al., Biochem. 15:4300-4309, 2003). Simultaneously, CA is oxidized to a quinone. Using nuclear magnetic resonance (NMR), we concluded that carbon (14) of CA is the single target of nucleophilic attack by GSH thiol. Facile oxidation of the catechol ring of CA results in conversion to its quinone derivative. Thiol-containing compounds such as GSH can induce a nucleophilic attack on the electrophilic carbon and thus form a GS-CA adduct.

Next, we assessed the rate of GS-CA adduct formation. Since the GS-CA adduct is highly stable, oxidation from catechol to quinone has been proposed to be the rate-limiting step of these chemical reactions. Although the reaction solution contained a molar excess of CA and GSH, the GS-CA adduct appeared very slowly. Even after an 18-h incubation, only 17.5% of the CA had reacted to form the adduct. This result suggests that the conversion (oxidation) of the catechol to the quinone form of CA is a very slow process in the cell-free system.

Next, we assessed the binding of CA to other thiols, in this case to bovine serum albumin (BSA). Because of its single free thiol group on cysteine 34, BSA has been used for in vitro demonstration of adduct formation with electrophilic compounds (Satoh et al., Proc. Nat. Acad. Sci. USA 103:768-773, 2006). In order to monitor this reaction, we synthesized CA-biotin (CAB), in which biotin is conjugated at the carbonic acid site of CA with a chemical linker. With peroxidase-conjugated streptavidin as a probe, we could detect adduct formation of BSA with CAB. For this purpose, BSA was mixed with vehicle or CAB in PBS at room temperature for 5 h, electrophoresed, and then probed with streptavidin. After exposure to CAB, a single band (68 kDa) corresponding to the complex of BSA and CAB was detected. In this manner, we demonstrated that CAB could form an adduct with BSA in a dose-dependent manner.

Additionally, we examined whether cysteine thiol was essential for formation of the complex. We reasoned that if carbon #14 of CA binds to the free cysteine of BSA, then pretreatment with NEM, an irreversible thiol alkylating agent, should abolish this binding. We found that pretreatment with NEM depressed the streptavidin signal in a dose-dependent manner, while the total protein remained virtually the same, as judged from Coomassie brilliant blue-staining of the gel. These results suggest that cysteine thiols are a target of CA.

CA activates the Keap1/Nrf2/ARE pathway. Neuroprotective effects of electrophilic compounds are often manifest via activation of the Keap1/Nrf2 pathway (Satoh et al., Proc. Nat. Acad. Sci. USA 103:768-773, 2006; Kraft et al., J. Neurosci. 24:1101-1112, 2004; Shih et al., J. Neurosci. 10321-10335, 2005). The initial reaction in this activation cascade is the binding of an electrophilic compound to specific cysteines on Keap1 protein (Hong et al., Chem. Res. Toxicol. 18: 1917-1926, 2005; Eggler et al., Proc. Nat. Acad. Sci. USA 102: 10070-10075, 2005; Zhang et al., Mol. Cell. Biol. 10941-10953, 2004). Such binding initiates a cellular transcription pathway leading to induction of phase 2 enzymes (Talalay, Biofactors 12:5-11, 2000; Padmanabham et al., Mol. Cell 21:689-700, 2006; Itoh et al., Free Radic. Biol. Med. 36:1208-1213, 2004). Therefore, we examined the domains of Keap1 (designated BTB, IVR, and DGR) to determine those essential for binding to CA. Accordingly, for co-immunoprecipitation experiments, we transfected COS7 cells with DNA expressing either HA-tagged wild type Keap1 protein (HA-WT Keap1) or various deletion mutants of tagged Keap1 protein (HA-ΔBTB Keap1, HA-ΔIVR Keap1, and HA-ΔDGR Keap1). The transfected COS7 cells were then treated with vehicle or 10 μM CAB and lysed. We quantified the expression level of Keap1 protein in total cell lysates with anti-HA antibody. Each Keap1 mutant protein was expressed at a similar level of the predicted molecular weight (57 kDa for HA-ΔBTB Keap1, 53 kDa for HA-ΔIVR Keap1, and 37 kDa for HA-ΔDGR Keap1). Next, in order to detect Keap1/CAB complexes, we immunoprecipitated cell lysates with streptavidin and probed with anti-HA antibody. A 73-kDa protein, corresponding to Keap1-WT bound to CAB, was observed in cells treated with CAB. ΔDGRKeap1 also manifested strong binding to CAB. In contrast, IVR Keap1 showed very little binding to CAB, whereas ΔBTB Keap1 displayed no binding at all. Taken together, these results are consistent with the notion that maximal CA binding requires the BTB and IVR domains of Keap1 protein (Hosoya et al., J. Biol. Chem. 29:27244-27250, 2005; Kobayashi et al., Mol. Cell. Biol. 26:221-229, 2006). The requirement of the BTB domain for CA binding is in accord with prior results (Hong et al., Chem. Res. Toxicol. 18:1917-1926, 2005; Eggler et al., Proc. Nat. Acad. Sci. USA 102:10070-10075, 2005; Zhang et al., Mol. Cell. Biol. 24:10941-10953, 2004).

After binding of the electrophilic quinone-form of CA to Keap1 protein, activation of the Keap1/Nrf2 pathway requires nuclear translocation of Nrf2 (Talalay, Biofactors 12:5-11, 2000; Padmanabham et al., Mol. Cell 21:689-700, 2006; Itoh et al., Free Radic. Biol. Med. 36:1208-1213, 2004). Thus, we next examined the intracellular distribution of Nrf2 protein in COS7 cells by immunofluorescence. Under basal conditions, Nrf2 protein was predominantly localized in the cytoplasm, but was translocated into the nucleus upon exposure to 10 μM CA, suggesting that Nrf2 was translocated in response to the binding of CA to Keap1 protein. Similar to COS7 cells, neural PC12h cells transfected with Keap1 (non-HA-tagged) expression vector and exposed to CA formed CA/Keap1 complexes.

Phase 2 enzymes represent an important effector activated by electrophilic-induction of the Keap1/Nrf2 pathway. In order to detect induction of the phase 2 enzymes γ-GCL light chain (GCL-L), γ-GCL heavy chain (GCL-H), HO-1, and NQO1, we performed RT-PCR using mRNA of PC12h cells pretreated with 10 μM CA. The cyclophilin A (CYPA) gene was used as an internal positive control. All of the phase 2 genes were induced by CA after a 6-24 h incubation. These results are consistent with the notion that CA induced a set of phase 2 genes, possibly through activation of the Keap1/Nrf2 pathway, as previously shown for other electrophiles.

Next, we examined the involvement of the Keap1/Nrf2 pathway more precisely by studying activation of the ARE. This transcription element responds to the Keap1/Nrf2 pathway; we monitored activation of the ARE by performing luciferase reporter gene assays using PC12h cells transfected with ARE(GSTYa)-luciferase (Alam et al., J. Biol. Chem. 274:26071-26077, 1999) in the presence or absence of an Nrf2 dominant-negative (DN) or Keap1 expression vector. Based on luciferase activity, CA (10 μM) stimulated expression of ARE-based transcription >10-fold. In contrast, CA-stimulated activation of the ARE was significantly repressed by co-transfection with Nrf2-DN or Keap1. This series of experiments suggests that CA activates the ARE via the Keap1/Nrf2 pathway.

CAB also significantly activated the ARE, but its potency was substantially lower than that of CA. For example, 20 μM CAB activated the ARE to a much lesser extent than 10 μM CA. Similarly, a greater level of CAB than CA was required to protect PC12h cells against oxidative glutamate toxicity. Thus, it appears that several times the dose of CAB than CA is required to activate the Keap1/Nrf2 pathway. CA protects PC12h cells by activating the Keap1/Nrf2 pathway.

Figure 4A:
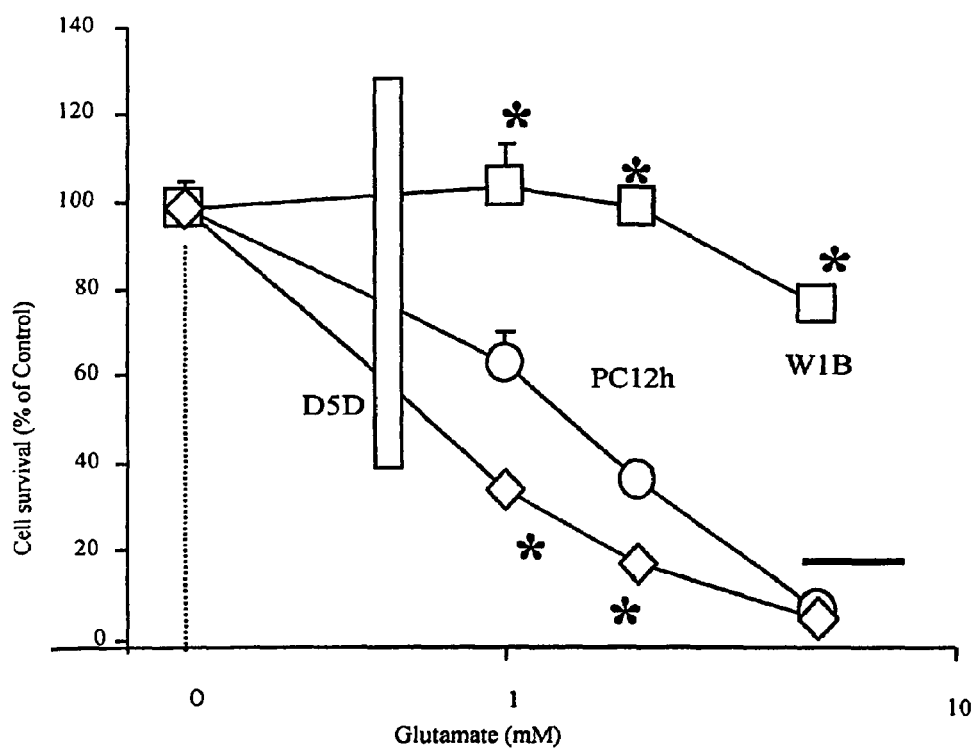
FIG. 4 shows that CA protects PC12h cells via Nrf2. (a) Nrf2DN increases cell death. PC12h cells, PC12hW1B cells, and PC12hD5D cells (expressing Nrf2DN) were incubated with various concentrations of glutamate for 20 h. Cell survival was assessed using the MTT assay. *Significantly different (p<0.01) from PC12h cells by ANOVA. (b) Dose-dependent activation of the ARE by CA and sulforaphane. PC12h cells were transfected with an ARE-luciferase reporter gene plasmid, and then incubated for 20 h with various concentrations of CA or sulforaphane. *Significantly different (p<0.01) between CA and sulforaphane by ANOVA. (c) CA protects PC12h cells in an Nrf2-dependent manner. Various concentrations of CA were added to PC12, PC or PC12hD5D cells 1 h prior to exposure to 5 mM glutamate for 20 h. Viability was then assessed by the MTT assay. *Significantly different (p<0.01) from PC12h cells by ANOVA.

Since many phase 2 enzymes are involved in the redox regulation of cells, induction of these enzymes often affords resistance to oxidative stress (Talalay, Biofactors 12:5-11, 2000; Padmanabham et al., Mol. Cell 21:689-700, 2006; Itoh et al., Free Rad. Biol. Med. 36:1208-1213, 2004). Thus, we examined whether CA could protect PC12h cells from such insults. We prepared naïve PC12h cells, Nrf2WT-expressing PC12h cells (PC12hW1B), and Nrf2DN-expressing PC12h cells (PC12hD5D). In order to examine the effects of the Keap1/Nrf2 pathway on cell survival in the face of oxidative stress, we exposed the cells to a high concentration of glutamate. In PC12h cells, high (millimolar) concentrations of glutamate induce oxidative cell death primarily by depleting intracellular GSH because of inhibition of cystine influx (Pereira and Oliveira, Free Rad. Biol. Med. 23:637-647, 1997). To visualize surviving and dead cells, we stained cultures with fluorescein diacetate (FDA) and propidium iodide (PI), respectively. Additionally, cell survival was quantified by the 3-(4,5-dimethylthiazol-2-yl)-2,5-diphenyl tetrazolium bromide (MTT) assay (FIG. 4A). We found that glutamate (1-10 mM) induced death of PC12h cells within 20 h whereas PC12hW1B cells, overexpressing Nrf2WT, were highly resistant to this form of oxidative stress. PC12hD5D cells, expressing Nrf2DN, exhibited increased susceptibility to cell death. These results suggest not only that Nrf2 protein can protect cells but that endogenous Nrf2 is involved in the cytoprotective response against oxidative stress.

Figure 4B:
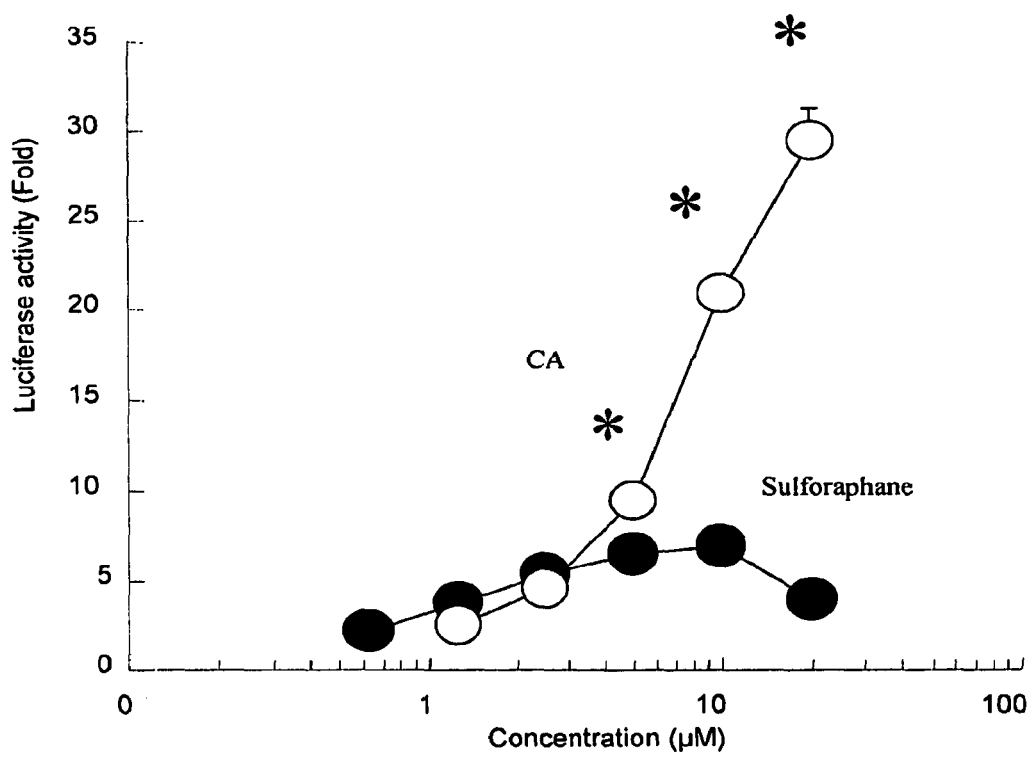

Next, we examined activation of the ARE by CA compared to sulforaphane, an electrophilic compound produced by plants and previously shown to potently activate the Keap1/NRf2 pathway (Kraft et al., J. Neurosci. 24:1101-1112, 2004; Hong et al., Chem. Res. Toxicol. 18:1917-1926, 2005). Surprisingly, on an equimolar basis CA activated the ARE to a much greater extent than sulforaphane (FIG. 4B). This difference in ARE activation appears to be critical for cell survival because sulforaphane did not protect PC12h cells against oxidative glutamate toxicity in our assays. This result is also consistent with the notion that the ability of CA to activate the ARE coincides with its neuroprotective effect, as observed below.

Figure 4C:
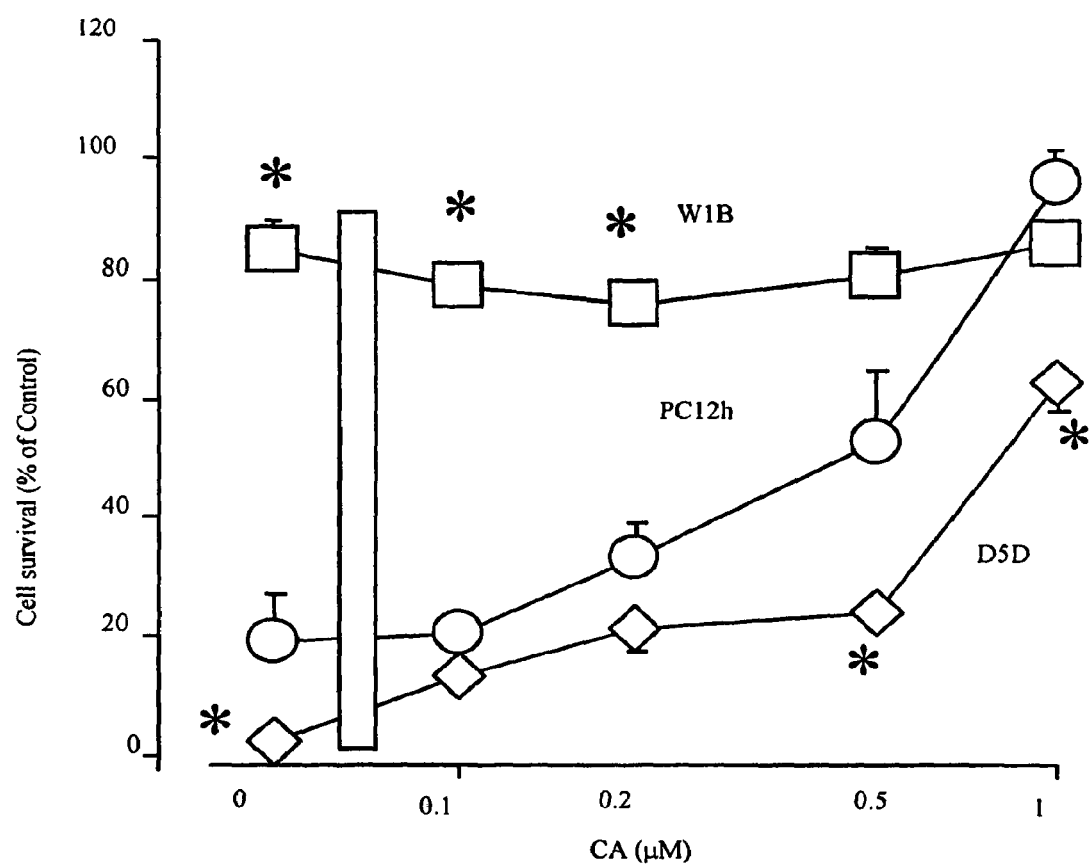

We next tested the hypothesis that CA-induced neuroprotection is mediated by the Keap1/NRf2 pathway. We found that 0.1-1 μM CA dose-dependently protected PC12h cells against oxidative glutamate toxicity (FIG. 4C). However, the protective effects afforded by CA were significantly suppressed in PC12hD5D (FIG. 4C). In contrast, PC12hWIB manifested less cell death after an oxidative glutamate insult. These results suggest that CA protected PC12h cells against oxidative stress in an Nrf2-dependent manner.

CA protects cortical neurons via activation of the Keap1/Nrf2 pathway. We also assessed whether CA could protect immature cortical neurons in primary culture from an oxidative glutamate insult; these cells do not yet express functional glutamate/NMDA receptors and consequently succumb to non-receptor-mediated oxidative cell death due to inhibition of cystine influx, similar to PC12h cells. We found that CA protected these cortical neurons from exposure to glutamate or rotenone. Glutamate (2 mM) and rotenone (300 nM) decreased the number of MAP2 and NeuN-positive cells to 30.8±2.5% and 25.8±1.9% of the control value, respectively. In contrast, CA (3 μM) increased cell survival in the face of these insults to 73.8±3.7% and 80.4±3.4%, respectively. These results suggest that CA protects primary CNS neurons against oxidative stress.

Next, we examined the actions of CA on excitotoxic (NMDA receptor-mediated) neuronal cell death. In this case, we used more mature cerebrocortical neurons in primary culture that expressed NMDA receptors. NMDA reduced the number of viable cells to 15±1.6%, whereas 3 µM CA increased the survival to 36±2.3%. Taken together, these results suggest that CA protected cultured primary neurons from NMDA receptor-mediated excitotoxicity as well as against non-receptor mediated oxidative stress.

Figure 5:
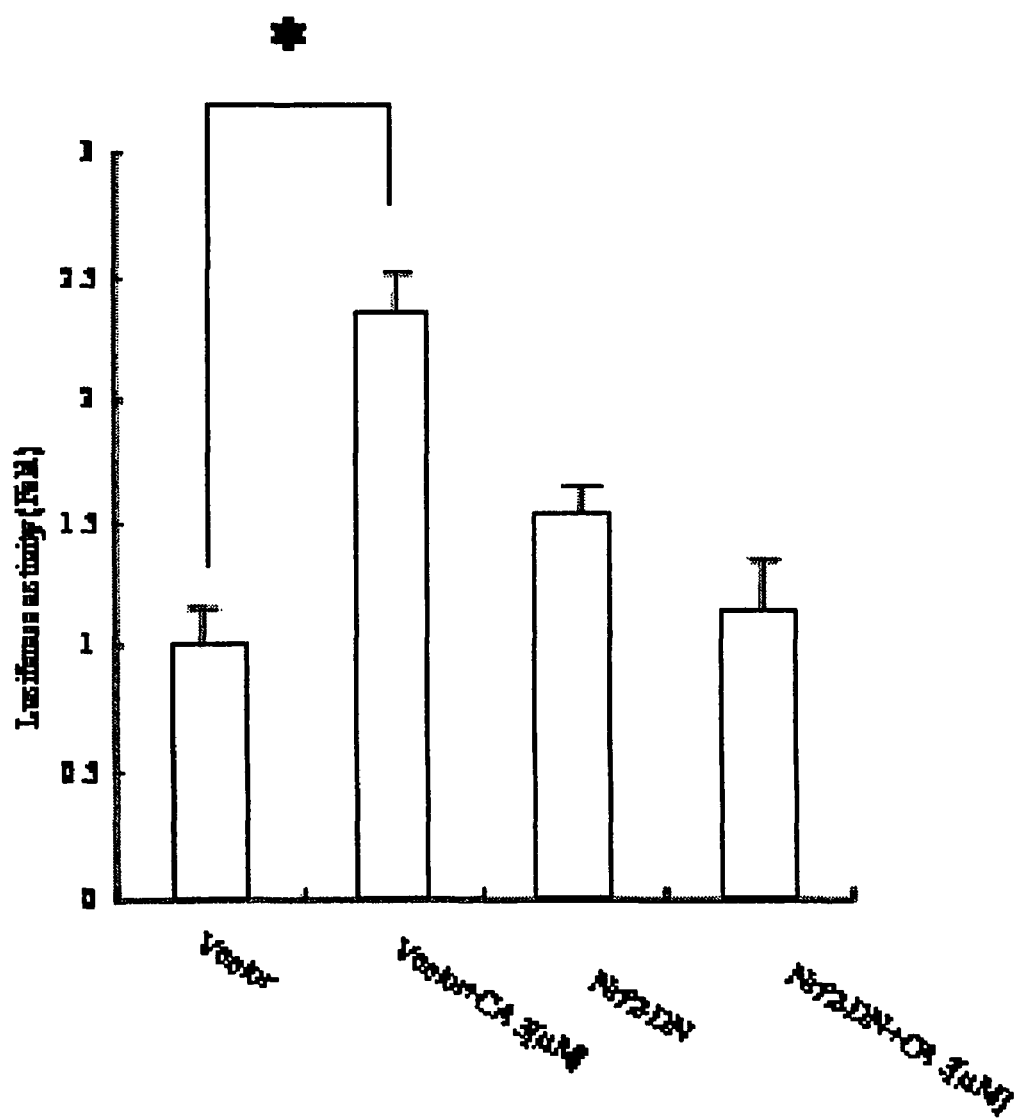
FIG. 5 shows that CA activates the ARE and protects cortical neurons in an Nrf2-dependent manner. Cortical cultures (E17, DIV21) were transfected with ARE-luciferase reporter gene DNA (1 μg/well) and co-transfected with pEF6 or pEFNrf2DN. CA (3 μM) or vehicle was then added to the cultures. After a 24-h incubation, cell lysates were used for luciferase reporter gene assays. Values are mean±SEM; *p<0.01 by ANOVA.

To confirm that CA activated the ARE in these cortical cultures, we performed luciferase reporter gene assays. ARE-mediated transcription increased 2.3-fold in the presence of 3 µM CA, and this effect was abrogated by Nrf2-DN, suggesting that CA activated the ARE in an Nrf2-dependent manner. CA accumulates both in neurons and in non-neuronal cells (FIG. 5).

In order to determine the site(s) of action of CA, we treated mixed neuronal/glial cortical cultures (E17, DIV21) with CAB, and then stained them with rhodamine-conjugated streptavidin after fixation. Concurrently, the cultures were stained with antibody against the neuronal marker MAP2 or the non-neuronal cell marker S100β. At low concentrations of CAB (e.g., 3 µM), neurons were not strongly labeled, whereas non-neuronal cells were strongly positive for CAB-streptavidin, indicating that CAB had accumulated in non-neuronal cells rather than in neurons. At higher concentrations of CAB (e.g., 10 µM), neurons were also labeled. These results suggest that CA accumulated in non-neuronal cells at low concentrations but also in neurons at higher concentrations.

CA accumulation in the brain. For the development of CA as a protective agent against neurodegenerative diseases, penetration into the brain is an essential requirement. To examine this aspect, we administered CA orally to mice (3 mg per 25 g mouse) and measured the level of CA (catechol-form) in serum and brain parenchyma by HPLC. Within 1 h, CA reached significant levels in the brain, suggesting that CA was able to penetrate the blood-brain barrier.

Figure 6:
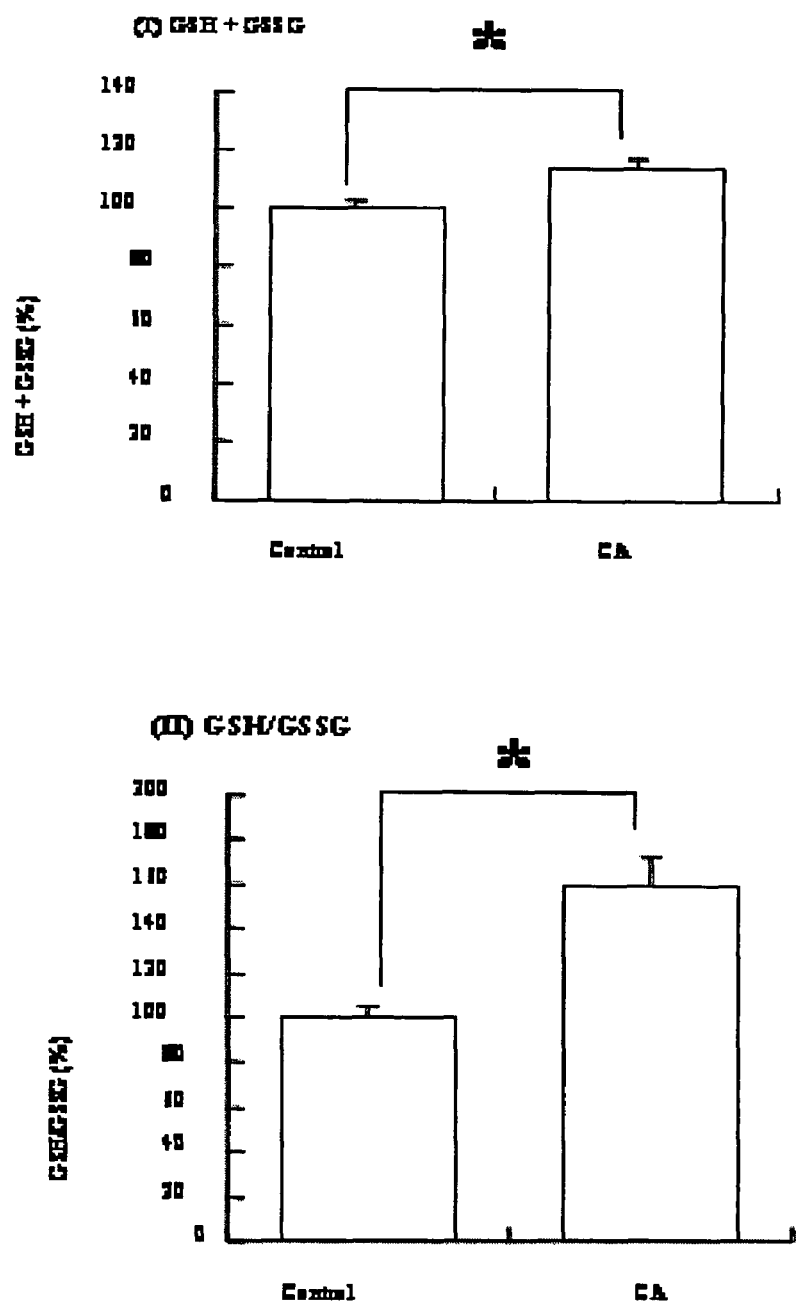
FIG. 6 shows CA increased reducing equivalents of GSH in the brain. Mice were fed 0.03% CA for 1 week, and their brains were then removed, lysed and subjected to GSH and GSSG measurement.

Next, we examined whether CA exhibited activity in the brain. Mice were allowed free access to food containing 0.03% CA for a week. Their brains were then removed, and extracts were prepared and measured for GSH and GSSG levels. Under these conditions, CA increased both total GSH+GSSG and the ratio of GSH/GSSG (FIG. 6). During these experiments, total RNA was also extracted from the brain and subjected to RT-PCR; we found significant induction of the phase 2 enzymes HO-1 and γ-GCS, consistent with the notion that CA activates the ARE, thus inducing phase 2 enzymes and increasing GSH levels. Therefore, we concluded that orally-administered CA could not only reach the brain but was also effective in activating potentially neuroprotective pathways. These experiments also suggest that chemical reactions occur in vivo that convert CA, which is normally not an electrophile in its catechol or "pro-drug" form," to an electrophilic (quinone) compound, because CA administration resulted in induction of phase 2 enzymes in the brain.

Most importantly, the elucidation of this mechanism set the stage for work with this electrophilic precursor compound to test its neuroprotective efficacy in vivo.

Figure 7:
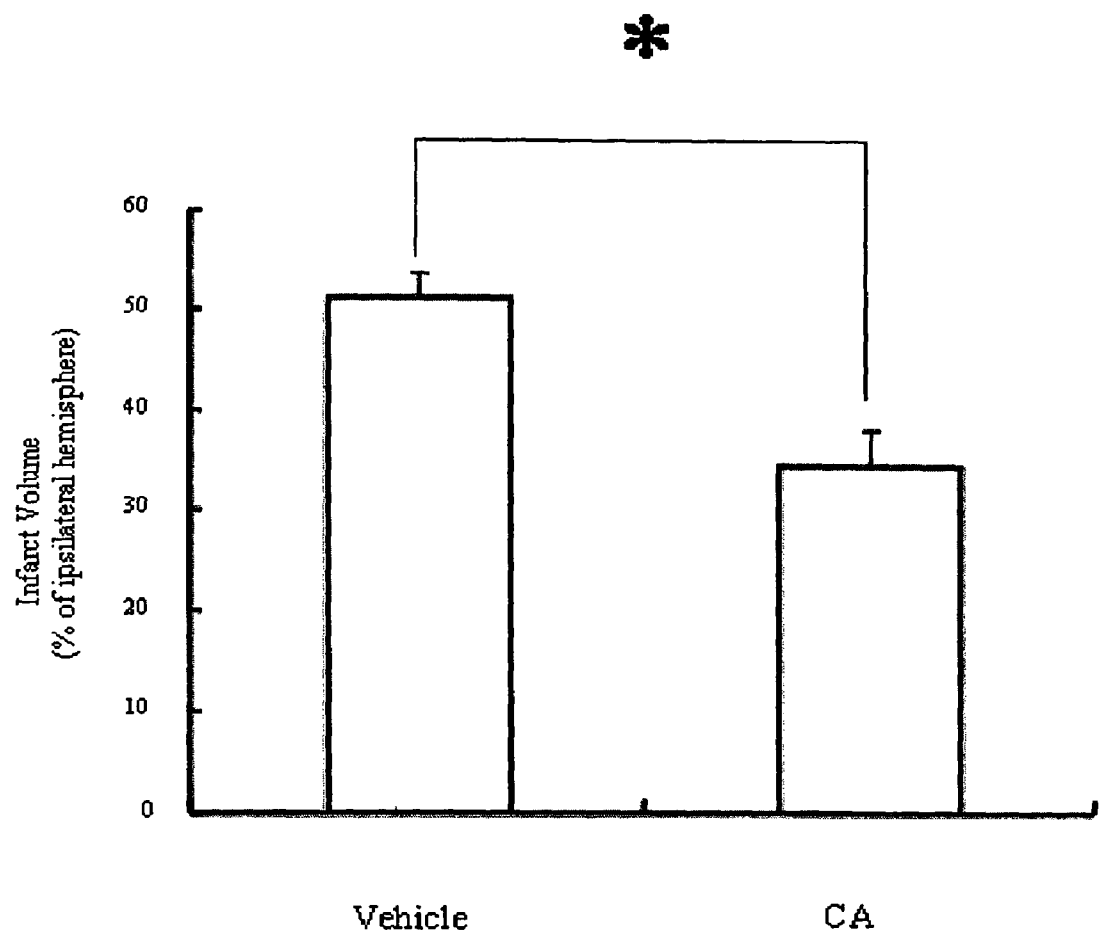
FIG. 7 shows that CA protects against cerebral ischemia induced by 2-h MCAO/24-h reperfusion and a quantification of infarct volume by TTC staining. CA decreased infarct volume compared to vehicle-treated mice. Data represent mean±SEM (vehicle-treated, n=9; CA-treated, n=9; *p<0.05 by ANOVA).

CA protects the brain from MCAO/reperfusion injury in vivo. Next, we tested whether CA could decrease the volume of cerebral infarcts after MCAO/reperfusion injury. CA or vehicle (10% DMSO in PBS) was injected intraperitoneally 1 h prior to MCAO. The volume of brain infarction (corrected for possible edema) was assessed by TTC staining of coronal sections 24 h after the onset of reperfusion. MCAO induced severe brain damage in vehicle-injected mice; the infarct volume was 51.2±2.4% of the ipsilateral hemisphere, similar to prior reports (Gu et al., Science 297:1186-1190, 2002; Gu et al., J. Neurosci. 25:6401-6408, 2005; Satoh et al., Proc. Nat. Acad. Sci. USA 103:768-773, 2006). In contrast, CA significantly reduced the infarct volume (to 34.5±3.6%) (FIG. 7), consistent with the notion that CA was neuroprotective in vivo.

Discussion

In the present experiments, we found that CA is neuroprotective both in vitro and in vivo from glutamate/oxidative stress and cerebral ischemia. Concerning the chemical entity that affords this protection, the question arises if the real effector is the catechol- or quinone-type of CA? If the catechol-type CA is the effector, it must protect neurons through its antioxidant activity. In contrast, if the quinone-type is the effector, it would protect neurons by activating the Keap1/Nrf2 pathway. In the present study, we found that the effector is the quinone-type and not the catechol-type molecule. This conclusion is based on the following results: (1) Quinone-type CA, but not catechol-type, activated the Keap1/Nrf2 pathway; (2) Activation of the Keap1/Nrf2 pathway by stable expression of WT Nrf2 protected PC12h cells against oxidative stress; (3) Inhibition of the Keap1/Nrf2 pathway by stable expression of DN Nrf2 increased oxidative stress-induced cell death and reduced protection by CA. Thus, although catechol-type CA could potentially exert antioxidant activity by donating a pair of electrons to oxygen radicals, this mechanism appears to play a limited role in the neuroprotection observed here.

The time course of conversion from catechol to quinone CA was rather slow in the cell-free system that we used. Then, how can the quinone form of CA be neuroprotective? One plausible explanation lies in the difference between the cell-free and cell-culture experiments employed here. Since cells have many thiols, for example, on GSH and cysteine-bearing proteins, quinones react rapidly with these thiols to form an adduct; removal of the quinone-type of CA by adduct formation shifts the equilibrium between free catechol and free quinone towards the quinone. Thus, conversion should be much faster in cell-based than in cell-free systems. Additionally, there are differences in thiol reactivity between GSH and various cysteine residues in proteins. For example, some proteins have potentially reactive cysteines, which can be easily converted to the thiolate anion if they are located in a motif of basic amino acids. Cysteine (151) of Keap1 is a typical example of such an active cysteine. This cysteine appears to be a sensor for electrophilic compounds. Thus, cysteine (151) of Keap1 should be more reactive with electrophilic compounds than GSH. Thus, the sustained presence of low concentrations of quinone-type CA may preferentially react with Keap1 rather than with GSH, and may thereby contribute to activation of the cell defense system. We speculate that this may be one of the reasons that CA is much less toxic than NEPP11, which itself is an electrophilic compound.

Figure 8:
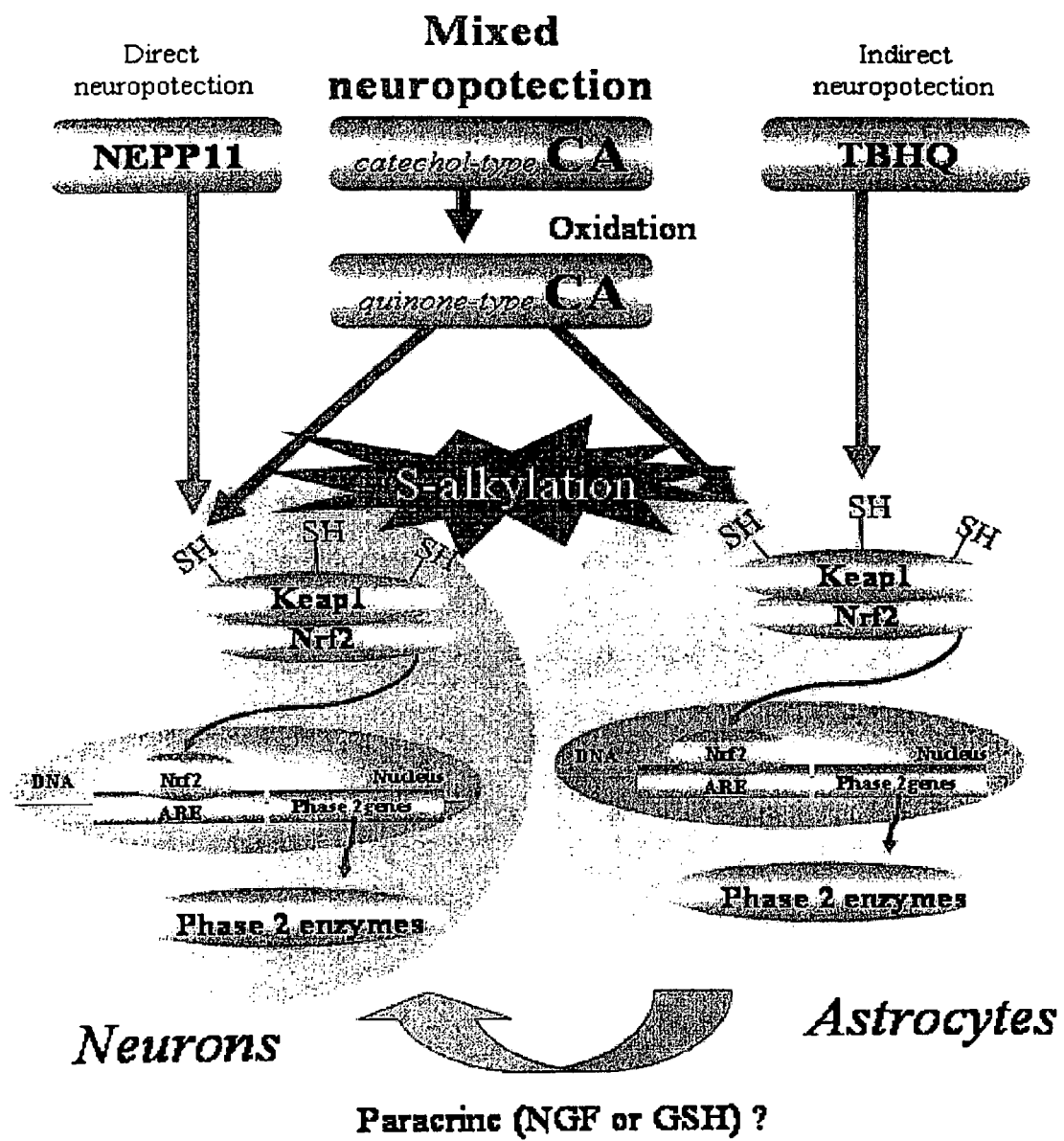
FIG. 8 shows a proposed mechanism of neuroprotective action of CA, NEPP11 and TBHQ. NEPP11 appears to protect neurons directly, TBHQ via effects on astrocytes, which in turn may release survival or neurotrophic factors (Ahlgren-Beckendorf et al., Glia 15:131-142, 1999; Kosaka and Yokoi, Biol. Pharm. Bull. 26:1620-1622, 2003), and CA by a "mixed" type of protection mediated by actions on both neurons and astrocytes.

In the present series of in vitro experiments, we showed the chemical and molecular mechanisms whereby CA protected neurons against oxidative stress. CA is converted from an electrophilic precursor (or pro-electrophilic) compound to an electrophilic form, thereby activating the neuroprotective Keap1/Nrf2 pathway (FIG. 8). The chemical mechanism involves a catechol-type CA that is oxidized to a quinone-type, with the carbon at position 14 [C(14)] becoming electrophilic. This quinone-type CA is subject to nucleophilic attack by the cysteine thiol of GSH or various other proteins to form an adduct. Importantly, via this chemical reaction, the cysteine thiol of Keap1 protein forms a Keap1-CA adduct, resulting in release of Nrf2 protein from the Keap1/Nrf2 complex. Nrf2 can then be translocated into the nucleus, where it activates transcription of phase 2 enzymes via ARE transcriptional elements. These phase 2 enzymes improve the redox state of neurons, contributing to the anti-oxidant defense system.

Although electrophilic compounds can possess a variety of chemical structures, the enone-type (e.g., NEPP11) and catechol-type (e.g., CA and TBHQ) represent major groups. From our prior findings and those of other groups (Satoh et al., Proc. Nat. Acad. Sci. USA 103:768-773, 2006; Kraft et al., J. Neurosci. 24:1101-1112, 2004; Shih et al., J. Neurosci. 25:10321-10335, 2005), we have proposed that the cellular distribution in the brain of enone- and quinine-type electrophilic compounds may be different. Enone-type electrophiles, including dienones such as NEPP11, appear to act preferentially in neurons based on our earlier findings that NEPP11 accumulates in neurons as opposed to astrocytes, and consequently induces neuronal HO-1 (Satoh et al., Proc. Nat. Acad. Sci. USA 103:768-773, 2006). In contrast, catechol-type electrophiles, including TBHQ, preferentially act on astrocytes, as evidenced by the fact that TBHQ activates the ARE in astrocytes and not in neurons (Kraft et al., J. Neurosci. 24:1101-1112, 2004; Shih et al., J. Neurosci. 25:10321-10335, 2005). In light of these findings, we proposed that the enone-type electrophile NEPP11 exerts a direct neuroprotective effect while the catechol-type TBHQ exerts a paracrine-type of neuroprotective action (Satoh and Lipton, Trends Neurosci. 30:38-45, 2007). Interestingly, CA appears to afford both direct and paracrine (hence, "mixed") neuroprotective effects, as discussed below.

In the immunohistochemical experiments we conducted using CAB, this labeled form of CA accumulated in non-neuronal cells at low concentrations (3 μM) and in neurons at higher concentrations (10 μM). However, ARE activation and consequent neuroprotection afforded by CAB were much weaker than by CA. This difference may have been due to lower permeability of cell membranes to CAB or lower binding affinity of CAB for Keap1 protein. In light of this difference, we estimate that <10 μM CA accumulates in both non-neuronal and neuronal cells. Thus, it is reasonable to propose that CA exerts actions on both cell types, similar to the astrocyte-mediated neuroprotective action previously seen for TBHQ and the neuronal-mediated neuroprotection previously observed for NEPP1.

An important advantage of electrophiles such as NEPP11 and CA as neuroprotective compounds is their transcriptional activation of antioxidant phase 2 enzymes. This type of neuroprotection could be of potential benefit in chronic neurodegenerative diseases such as Parkinson's and Alzheimer's diseases. Previously, NEPP11 was shown to protect neurons via electrophilic chemical reaction (Satoh et al., Proc. Nat. Acad. Sci. USA 103:768-773, 2006; Satoh and Lipton, Trends Neurosci. 30:38-45, 2007). However, NEPP11 has a serious problem as a potential therapeutic agent because systemic administration can result in reaction with thiol substrates prior to reaching the intended target in the brain. It would be far better to have a pro-electrophilic compound that remains non-reactive until it is converted to an electrophile by the oxidative insult at the pathological site of its intended action. Such as drug would represent what has been termed a "pathologically-activated therapeutic" (Lipton, Nature 428:473, 2004), and we believe that CA may constitute such an agent. We feel that CA has two clear-cut advantages over NEPP11 and similar compounds: (i) low potential toxicity due to conversion of the pro-drug to an electrophile by the oxidative insult at the pathological site, and (ii) effective penetrance into brain tissue. These characteristics emanate from the chemical structure of CA. Accordingly, when the catechol is oxidized to a quinone, it becomes more hydrophobic and will tend to stay in the injured tissue.

Moreover, CA is less toxic than NEPP11 in vitro. CA manifests a large therapeutic index; i.e., 100 μM CA is not toxic to neural cells, whereas as little as 1-3 is neuroprotective. The lower toxicity of CA may also be accounted for by the fact that, unlike NEP11, CA only becomes electrophilic at or near the site of injury. Oxidative stress plays a critical role in the progression of neurodegenerative disorders (Coyle and Puttfarcken, Science 262:689-695, 1993). We demonstrate here that this pathological level of oxidation can be used to activate pro-electrophilic compounds at the target site to provide neuroprotection where it is needed. Thus, this approach represents a novel strategy against neurodegenerative disorders by activating neuroprotective pro-electrophilic drugs via the very pathological activity that they are meant to combat. Moreover, to our knowledge, this study is the first demonstration of a natural product protecting neurons by thiol (S-) alkylation, resulting in activation of the Keap1/Nrf2 pathway. Thus, naturally-occurring pro-electrophilic compounds produced by plants are candidate neuroprotective agents for the treatment of neurodegenerative diseases.

References

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A compound, or pharmaceutically acceptable salt thereof, of Formula IV:

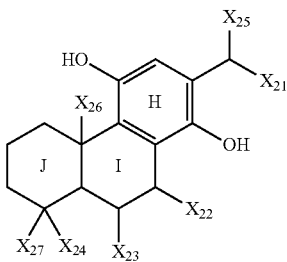

Formula IV wherein:
$X_{24}$, and $X_{27}$ are each independently H, OH, oxo, or Y; and $X_{21}$, $X_{22}$, $X_{23}$, and $X_{25}$ are each null;
Y is B—C-D or C—B-D or C—B—C-D, any of which may be attached to a ring carbon to form a fused ring;
B is selected from the group consisting of null, carbonyl, carboxy, ether, sulfanyl, amino, —NHC(O)— and —C(O)NH—, any of which is optionally substituted;
C is selected from the group consisting of null, alkyl, cycloalkyl, alkenyl, cycloalkenyl, aryl, arylalkyl, and arylalkenyl, any of which is optionally substituted, and which may be attached to a ring carbon so as to form a fused ring; and
D is selected from the group consisting of null, carboxy, benzoic acid, hydroxybenzoic acid, $SO_3H$, $PO_3$, $NO_3$, $NO_2$, NO, amino, hydroxyl;
wherein $X_{26}$ is methyl; and
wherein B, and C are optionally substituted with one or more substituents independently selected from lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea.

2. The compound of claim 1 wherein C is an alkyl.

3. The compound of claim 1 wherein $X_{27}$ and $X_{24}$ are each independently methyl.

* * * * *